(12) United States Patent
Bru Roig et al.

(10) Patent No.: US 12,421,203 B2
(45) Date of Patent: Sep. 23, 2025

(54) SUBSTITUTED 4-METHYLENE-TETRAHYDROPYRANS, 4-METHYL-DIHYDROPYRANS AND 4-METHYL-TETRAHYDROPYRANS AND USE THEREOF AS AROMA CHEMICALS

(71) Applicant: BASF SE, Ludwigshafen am Rhein (DE)

(72) Inventors: Miriam Bru Roig, Lampertheim (DE); Florian Garlichs, Lampertheim (DE); Manuel Danz, Ludwigshafen am Rhein (DE); Ralf Pelzer, Lampertheim (DE); Helmut Kronemayer, Ludwigshafen am Rhein (DE); Volker Hickmann, Ludwigshafen am Rhein (DE); Melanie Weingarten, Ludwigshafen am Rhein (DE)

(73) Assignee: BASF SE, Ludwigshafen am Rhein (DE)

( * ) Notice: Subject to any disclaimer, the term of this patent is extended or adjusted under 35 U.S.C. 154(b) by 601 days.

(21) Appl. No.: 17/783,670

(22) PCT Filed: Dec. 15, 2020

(86) PCT No.: PCT/EP2020/086164
§ 371 (c)(1),
(2) Date: Jun. 9, 2022

(87) PCT Pub. No.: WO2021/122558
PCT Pub. Date: Jun. 24, 2021

(65) Prior Publication Data
US 2023/0074079 A1    Mar. 9, 2023

(30) Foreign Application Priority Data

Dec. 16, 2019   (EP) .................... 19216608

(51) Int. Cl.
*C07D 309/06*   (2006.01)
*C07D 319/06*   (2006.01)
(52) U.S. Cl.
CPC ......... *C07D 309/06* (2013.01); *C07D 319/06* (2013.01)
(58) Field of Classification Search
CPC .................................. C07D 309/06
See application file for complete search history.

(56) References Cited

U.S. PATENT DOCUMENTS

| 8,779,169 B2 * | 7/2014 | Gralla | ......... C07D 309/10 549/423 |
| 9,428,481 B2 * | 8/2016 | Gralla | ......... C07D 309/10 |
| 2014/0107352 A1 | 4/2014 | Stork et al. | |

FOREIGN PATENT DOCUMENTS

EP   1493737 A1   1/2005

OTHER PUBLICATIONS

International Search Report and Written Opinion received for PCT Patent Application No. PCT/EP2020/086164, mailed on Mar. 16, 2021, 6 pages.

* cited by examiner

*Primary Examiner* — Golam M Shameem
(74) *Attorney, Agent, or Firm* — Faegre Drinker Biddle & Reath LLP

(57) ABSTRACT

The present invention relates to substituted 4-methylene-tetrahydropyrans, 4-methyl-dihydropyrans and 4-methyl-tetrahydropyrans of formula (I), where the variables are as defined in the claims and description, to a stereoisomer thereof, to a mixture of stereoisomers thereof, to a mixture of different di- and tetrahydropyrans (I) and to a mixture containing at least one di- or tetrahydropyran (I) and at least one cyclic acetal which is a 1,3-dioxan carrying in 2-position an isobutanol-2-yl-(derived) substituent and in 4,4- or 5,5-position two methyl substituents. The invention also relates to the use of such compounds as an aroma chemical and/or for modifying and/or enhancing the aroma of a composition, to compositions comprising such compounds, to methods for preparing such compounds and to a product obtainable by these methods.

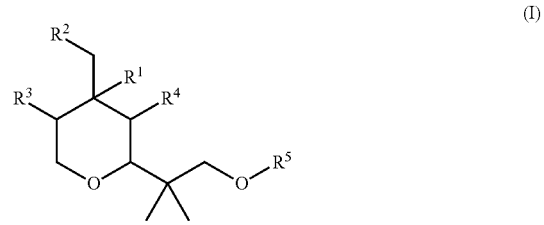

14 Claims, No Drawings

SUBSTITUTED 4-METHYLENE-TETRAHYDROPYRANS, 4-METHYL-DIHYDROPYRANS AND 4-METHYL-TETRAHYDROPYRANS AND USE THEREOF AS AROMA CHEMICALS

CROSS-REFERENCE TO RELATED APPLICATIONS

This application is a national stage application (under 35 U.S.C. § 371) of PCT/EP2020/086164, filed Dec. 15, 2020, which claims benefit of European Application No. 19216608.0, filed Dec. 16, 2019, both of which are incorporated herein by reference in their entirety.

The present invention relates to substituted 4-methylene-tetrahydropyrans, 4-methyldihydropyrans and 4-methyl-tetrahydropyrans of formula (I) as defined below carrying in ortho-position to the ring oxygen atom an isobutanol-2-yl-(derived) substituent, to a stereoisomer thereof, to a mixture of stereoisomers thereof, to a mixture of different di- and tetrahydropyrans (I) and to a mixture containing at least one di- or tetrahydropyran (I) and at least one cyclic acetal which is a 1,3-dioxan carrying in 2-position an isobutanol-2-yl-(derived) substituent and in 4,4- or 5,5-position two methyl substituents. The invention also relates to the use of such compounds as an aroma chemical and/or for modifying and/or enhancing the aroma of a composition, to compositions comprising such compounds, to methods for preparing such compounds and to a product obtainable by these methods.

BACKGROUND OF THE INVENTION

Aroma chemicals, especially fragrances, are of great interest especially in the field of cosmetics and cleaning and laundry compositions. Fragrances of natural origin are mostly expensive, often limited in their available amount and, on account of fluctuations in environmental conditions, are also subject to variations in their content, purity etc. To circumvent these undesirable factors, it is therefore of great interest to create synthetic substances which have sensory properties that resemble more expensive natural fragrances or which have novel and interesting sensory profiles.

Despite a large number of already existing aroma chemicals, there is a constant need for new components in order to be able to satisfy the multitude of properties desired for extremely diverse areas of application. These include, firstly, the sensory properties, i.e. the compounds should have advantageous odiferous (olfactory) or gustatory properties. Furthermore, aroma chemicals should also have additional positive secondary properties, such as e.g. an efficient preparation method, the possibility of providing better sensory profiles as a result of synergistic effects with other aroma chemicals, a higher stability in a wide range of compositions as well as under certain application conditions, a higher extendability and/or a better staying power.

However, since even small changes in chemical structure bring about massive changes in the sensory properties such as odor and also taste, the targeted search for substances with certain sensory properties such as a certain odor is extremely difficult. The search for new fragrances and flavorings is therefore in most cases difficult and laborious without knowing whether a substance with the desired odor and/or taste will even actually be found.

EP-A-1493737 describes the preparation of 4-methylenetetrahydropyrans or their double bond isomers 4-methyldihydropyrans which are said to be useful synthetic intermediates of perfumes, pharmaceutical preparations or agrochemicals. The compounds carry in ortho-position to the ring oxygen atom an alkyl, alkenyl, optionally substituted cycloalkyl or optionally substituted aryl group.

US 2014/0107352 describes such compounds as intermediates in the synthesis of 4-methyltetrahydropyrans.

It was the object of the present invention to provide new aroma chemicals. Furthermore, odor-intensive substances are sought, which can be used as aroma compositions. Besides, these substances should be combinable with other aroma chemicals, allowing the creation of novel advantageous sensory profiles. In addition, the process for the preparation of these new aroma chemicals should be easy and efficient to allow their fast, economic and environmentally friendly manufacturing.

These and further objects are achieved by the compound of formula (I) or mixtures thereof [i.e. mixtures of different compounds (I), to be more precise of two or more different compounds (I)] or stereoisomers thereof or mixtures with the corresponding cyclic acetals (1,3-dioxans), as shown below.

SUMMARY OF THE INVENTION

The invention relates to a compound of the general formula (I)

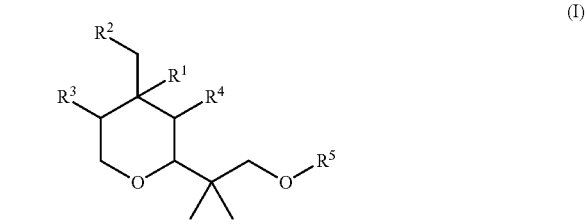

wherein
$R^1$, $R^2$, $R^3$ and $R^4$ are hydrogen; or
one of $R^2$, $R^3$ or $R^4$ together with $R^1$ represents a double bond; and the others of $R^2$, $R^3$ or $R^4$ are hydrogen; and
$R^5$ is selected from the group consisting of hydrogen, $C_1$-$C_4$-alkyl and —C(=O)—$R^6$; where
$R^6$ is selected from the group consisting of hydrogen and $C_1$-$C_4$-alkyl;
or a stereoisomer thereof or a mixture of stereoisomers thereof or a mixture of different compounds (I);
or a mixture of at least one compound of the formula (I) with one or both of the compounds of the formula (II.1) and/or (II.2)

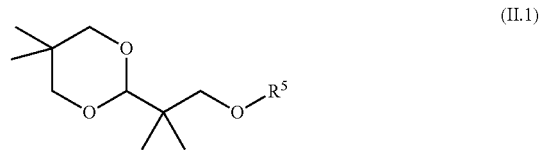

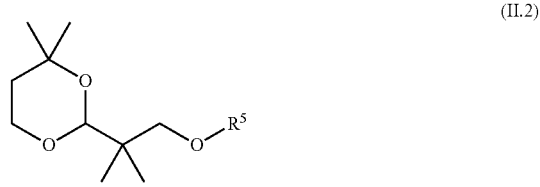

wherein $R^5$ is as defined above.

Another aspect of the invention relates to the use of a compound of formula (I), of a stereoisomer thereof, of a mixture of stereoisomers thereof, of a mixture of different compounds (I) or of a mixture of at least one compound of the formula (I) with one or both of the compounds of the formula (II.1) and/or (II.2) as an aroma chemical.

The invention also relates to the use of a compound of formula (I), a stereoisomer thereof, a mixture of stereoisomers thereof, a mixture of different compounds (I) or a mixture of at least one compound of the formula (I) with one or both of the compounds of the formula (II.1) and/or (II.2), as defined above, for modifying and/or enhancing the aroma of a composition; in particular for modifying and/or enhancing the fragrance impression of a composition; specifically for modifying the scent character of a fragranced ready-to-use composition.

The invention further relates to a method of preparing an aroma chemical composition, in particular a fragranced composition, specifically a fragranced ready-to-use composition, comprising incorporating at least one compound of formula (I), optionally in admixture with one or both of the compounds of the formula (II.1) and/or (II.2), a stereoisomer thereof or a mixture of stereoisomers thereof, into a composition, in particular into a ready-to-use composition.

The invention moreover relates to a method of modifying and/or enhancing the aroma of a composition; preferably for modifying and/or enhancing the fragrance impression of a composition; in particular for modifying the scent character of an aroma composition, in particular of a fragranced composition, specifically of a fragranced ready-to-use composition, comprising incorporating at least one compound of formula (I), optionally in admixture with one or both of the compounds of the formula (II.1) and/or (II.2), a stereoisomer thereof or a mixture of stereoisomers thereof, into a composition, in particular into a ready-to-use composition.

In another aspect, the invention relates to a composition comprising a compound of formula (I) or a stereoisomer thereof or a mixture of two or more stereoisomers thereof or a mixture of two or more different compounds of the formula (I) or a mixture of at least one compound of the formula (I) with one or both of the compounds of the formula (II.1) and/or (II.2), and at least one further component selected from the group consisting of aroma chemicals, non-aroma chemical carriers, anti-oxidants and deodorant-active agents.

Another aspect of the invention relates to a method for preparing a compound of formula (I), a stereoisomer thereof, a mixture of stereoisomers thereof, a mixture of different compounds (I) or a mixture of at least one compound of the formula (I) with one or both of the compounds of the formula (II.1) and/or (II.2), which comprises reacting isoprenol with hydroxypivalinaldehyde in acidic medium to obtain a reaction mixture containing a compound (I) in which $R^5$ is H and one of $R^2$, $R^3$ or $R^4$ together with $R^1$ represents a double bond while the others of $R^2$, $R^3$ or $R^4$ are hydrogen; and if desired etherifying or esterifying this compound to give a compound (I) in which $R^5$ is different from H. To obtain compounds in which $R^1$, $R^2$, $R^3$ and $R^4$ are hydrogen, the compound wherein one of $R^2$, $R^3$ or $R^4$ together with $R^1$ represents a double bond while the others of $R^2$, $R^3$ or $R^4$ are hydrogen is subjected to a hydrogenation reaction, either before or after the etherification or esterification reaction.

Yet another aspect of the invention relates to a method for preparing a compound of formula (I) wherein $R^5$ is different from hydrogen, a stereoisomer thereof, a mixture of stereoisomers thereof or a mixture of different compounds (I), which comprises subjecting hydroxypivalinaldehyde to an etherification or esterification reaction and reacting the etherification or esterification product with isoprenol under $BF_3$ catalysis to obtain a product in which $R^5$ is $C_1$-$C_4$-alkyl or —C(=O)—$R^6$ and one of $R^2$, $R^3$ or $R^4$ together with $R^1$ represents a double bond while the others of $R^2$, $R^3$ or $R^4$ are hydrogen. To obtain compounds in which $R^1$, $R^2$, $R^3$ and $R^4$ are hydrogen, the compound wherein one of $R^2$, $R^3$ or $R^4$ together with $R^1$ represents a double bond while the others of $R^2$, $R^3$ or $R^4$ are hydrogen is subjected to a hydrogenation reaction.

Finally, the invention relates to a product obtainable by said preparation methods.

DETAILED DESCRIPTION OF THE INVENTION

Definitions

In the context of the present invention, the term "aroma" refers to a sensory property and comprises an odor and/or a flavor.

The term "aroma chemical" denotes a substance which is used to obtain an aroma impression (the term "aroma impression" is used interchangeably herein with the term "note") and comprises its use to obtain an olfactory and/or a flavor impression. The term "olfactory impression" or "odor impression" denotes an odor impression without any positive or negative judgement, while the term "scent impression" or "fragrance impression" (used interchangeably herein) as used herein is connected to an odor impression which is generally felt as pleasant. Thus a "fragrance" or "scent" denotes an aroma chemical which predominately induces a pleasant odor impression. A flavor denotes an aroma chemical which induces a taste impression.

The term "aroma profile" denotes the overall aroma impression of an aroma chemical and is composed of the individual aroma impressions of an aroma chemical.

The term "aroma composition", as used herein, refers to a composition which induces an aroma. The term aroma composition comprises "odor composition" and/or "flavor composition". An odor composition is a composition which predominately induces an odor impression, whereas a flavor composition is a composition which predominantly induces a taste impression.

The term "odor composition" comprises "fragrance composition" or "scent composition" (used interchangeably herein), which predominately induce an odor impression which is generally felt as pleasant.

"Pleasant odor", "pleasant odor impression", "pleasant odiferous properties", "odor impression felt as pleasant" and similar terms are hedonistic expressions which describe the niceness and conciseness of an odor impression conveyed by an aroma chemical. The more general hedonistic expressions "advantageous sensory properties" or "advantageous organoleptic properties" describe the niceness and conciseness of an organoleptic impression conveyed by an aroma chemical. In terms of the present invention, the terms "organoleptic" and "sensory" relate to olfactory or flavor properties. "Niceness" and "conciseness" are terms which are familiar to the person skilled in the art, a perfumer. Niceness generally refers to a spontaneously brought about, positively perceived, pleasant sensory impression. However, "nice" does not have to be synonymous with "sweet". "Nice" can also be the odor of musk or sandalwood. "Conciseness" generally refers to a spontaneously brought about sensory impression which—for the same test panel—brings about a reproducibly identical reminder of something specific. For example, a substance can have an odor which is spontaneously reminiscent of that of an "apple": the odor would then be concisely of "apples". If this apple odor were very pleasant because the odor is reminiscent, for example, of a sweet, fully ripe apple, the odor would be termed "nice". However, the odor of a typical apple tart can also be concise. If both reactions arise upon smelling the substance, in the example thus a nice and concise apple odor, then this substance has particularly advantageous sensory properties.

The term "odor-intensive substances" refers to substances or aroma chemicals exhibiting intense odor impressions. Intense odor impressions are to be understood as meaning those properties of aroma chemicals which permit a striking perception even in very low gas space concentrations.

The intensity can be determined via a threshold value determination. A threshold value is the concentration of a substance in the relevant gas space at which an odor impression can just still be perceived by a representative test panel, although it no longer has to be defined. A substance class which probably belongs to the most odor-intensive known substance classes, i.e. has very low odor threshold values, are thiols, whose threshold value is often in the ppb/m$^3$ range.

The term "tenacity" describes the evaporation behavior over time of an aroma chemical. The tenacity can for example be determined by applying the aroma chemical to a test strip, and by subsequent olfactory evaluation of the odor impression of the test strip. For aroma chemicals with high tenacity the time span after which the panel can still identify an aroma impression is long.

The term "substantivity" describes the interaction of an aroma chemical with a surface, such as for example the skin or a textile, especially after subsequent treatment of the surface, such as for example washing. The substantivity can for example be determined by washing a textile with a textile detergent composition comprising the aroma chemical and subsequent olfactory evaluation of the textile directly after washing (wet textile) as well as evaluation of the dry textile after prolonged storage.

The term "stability" describes the behavior of an aroma chemical upon contact with oxygen, light and/or other substances. An aroma chemical with high stability maintains its aroma profile over a long period in time, preferably in a large variety of compositions and under various storage conditions.

In order to impart a long-lasting aroma impression to a composition or to a surface treated with a composition, the tenacity, the substantivity as well as the stability of the aroma chemical in the compositions should preferably be high.

The term "booster", "boosting" or "boost" is used herein to describe the effect of enhancing and/or modifying the aroma of an aroma chemical or of a composition. The term "enhancing" comprises an improvement of the niceness and/or conciseness of an aroma and/or an improvement of the intensity. The term "modifying" comprises the change of an aroma profile.

Booster effects are particularly desired in fragrance composition when top-note-characterized applications are required, in which the odor is to be conveyed particularly quickly and intensively, for example in deodorants, air fresheners or in the taste sector in chewing gums.

The terms "compound" and "substance" are used synonymously throughout the invention.

In the context of the present invention, the expression "$C_1$-$C_4$-alkyl" refers to methyl, ethyl, n-propyl, isopropyl, n-butyl, sec-butyl, isobutyl and tert-butyl. Preferably, the expression "$C_1$-$C_4$-alkyl" refers to $C_1$-$C_3$-alkyl, i.e. to methyl, ethyl, n-propyl and isopropyl, and in particular to $C_1$-$C_2$-alkyl, i.e. to methyl and ethyl.

In one alternative of the definition of $R^1$, $R^2$, $R^3$ and $R^4$ in compounds (I), one of $R^2$, $R^3$ or $R^4$ together with $R^1$ represents a double bond; and the others of $R^2$, $R^3$ or $R^4$ are hydrogen This means of course that the double bond is formed by the bond present between the carbon atoms to which $R^2$, $R^3$ or $R^4$ and $R^1$ are bound and a bond formed by $R^2$, $R^3$ or $R^4$ together with $R^1$. Thus, if $R^2$ together with $R^1$ represents a double bond and $R^3$ and $R^4$ are hydrogen, this results in a compound of formula (I-1). If $R^3$ together with $R^1$ represents a double bond and $R^2$ and $R^4$ are hydrogen, this results in a compound of formula (I-2). If $R^4$ together with $R^1$ represents a double bond and $R^2$ and $R^3$ are hydrogen, this results in a compound of formula (I-3).

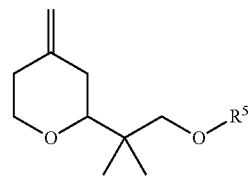

(I-1)

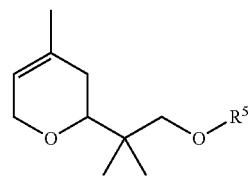

(I-2)

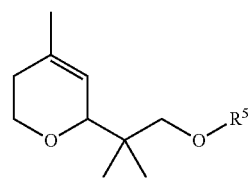

(I-3)

If $R^5$ has the same meaning in all three compounds (I-1), (I-2) and (I-3), these compounds can be regarded as double bond isomers of each other.

The term "stereoisomers" as used in context with the present invention relates specifically to optical isomers, such as enantiomers or diastereomers, the latter existing due to more than one stereogenic center in the molecule. The compounds of the formula (I) have at least one stereogenic center, namely the carbon atom of the di- or tetrahydropyran ring adjacent to the oxygen ring atom carrying the isobutanol-2-yl- or isobutanol-2-yl-derived substituent. Another stereogenic center may be present in the radical $R^5$, e.g. if this is sec-butyl or if this is —C(=O)—$R^6$, where $R^6$ is sec-butyl; the carbon atom marked with an asterisk in the sec-butyl group —*CH(CH$_3$)CH$_2$CH$_3$ being in each case the stereogenic center. Yet another stereogenic center present in compounds (I) in which $R^1$, $R^2$, $R^3$ and $R^4$ are hydrogen is the carbon atom in 4-position of the tetrahydropyran ring carrying the methyl group.

In terms of the present invention, the term "pure enantiomer" is understood as a nonracemic mixture of a specific compound, where the desired enantiomer is present in an enantiomeric excess of >90% ee.

In terms of the present invention, the term "pure diastereomer" is understood as a mixture of the diastereomers of a specific compound, where the desired diastereomer is present in an amount of >90%, based on the total amount of diastereomers of said compound.

In the present context, the term "compound I", "compound (I)" or "compound of formula (I)", when not defined as a specific stereoisomer or a specific mixture of stereoisomers, refers to the form of the compound as it is obtained in a non-stereoselective method used for its production. The term is however also used if it is not necessary or not possible to specify in more detail the stereochemistry of the compound (I).

If in the following the compound of formula (I) is defined to be a specific, defined compound (and not to be a mixture of different compounds I), this means that the compound contains less than 5% by weight, preferably less than 3% by weight and in particular less than 1% by weight of other compounds I, relative to the overall weight of the specific, defined compound I and the optionally present other compound(s) I.

In mixtures containing different compounds (I), these differ in the definition of the radicals $R^1$ to $R^4$ and/or in the definition of $R^5$. Preferably, the compounds in the mixture differ only in the definition of the radicals $R^1$ to $R^4$; especially for the case that one of $R^2$, $R^3$ or $R^4$ together with $R^1$ represents a double bond; and the others of $R^2$, $R^3$ or $R^4$ are hydrogen; meaning in this case that the mixture contains two or three of the compounds (I-1), (I-2) and (I-3), where in these compounds $R^5$ has the same meaning. However, due to the preparation method in which compounds (I) in which $R^5$ is not H are prepared from compounds (I) in which $R^5$ is H or from other alcohol precursors which have to be converted into ether or ester precursors, such compounds may also contain compounds (I) in which $R^5$ is H if the reaction is not complete and/or if no isolation/purification step is carried out or not to a sufficient extent. In such mixtures, compounds (I) in which $R^5$ is H are generally contained in only minor amounts, such as at most 10% by weight, preferably at most 5% by weight, in particular at most 2% by weight, based on the total weight of all compounds (I) present in the mixture.

The remarks made below concerning preferred definitions of the variables are valid on their own as well as preferably in combination with each other concerning the compounds of formula (I), as defined herein, where applicable, as well as concerning the compositions, uses and methods of the invention as defined herein.

Embodiments (E.x) of the Invention

General and preferred embodiments E.x are summarized in the following, non-exhaustive list. Further preferred embodiments become apparent from the paragraphs following this list.

E.1. A compound of the formula (I)

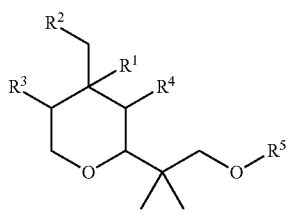

(I)

wherein
$R^1$, $R^2$, $R^3$ and $R^4$ are hydrogen; or
one of $R^2$, $R^3$ or $R^4$ together with $R^1$ represents a double bond; and the others of $R^2$, $R^3$ or $R^4$ are hydrogen; and
$R^5$ is selected from the group consisting of hydrogen, $C_1$-$C_4$-alkyl and —C(=O)—$R^6$; where
$R^6$ is selected from the group consisting of hydrogen and $C_1$-$C_4$-alkyl;
or a mixture thereof [i.e. a mixture of different compounds of the formula (I)], a stereoisomer thereof or a mixture of stereoisomers thereof;
or a mixture of at least one compound of the formula (I) with one or both of the compounds of the formula (II.1) and/or (II.2)

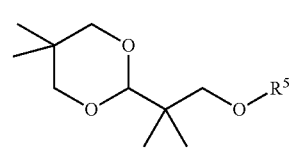

(II.1)

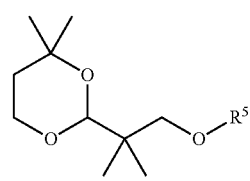

(II.2)

wherein $R^5$ is as defined above.

E.2. The compound as defined in embodiment E.1, wherein one of $R^2$, $R^3$ or $R^4$ together with $R^1$ represents a double bond; and the others of $R^2$, $R^3$ or $R^4$ are hydrogen.

E.3. The compound as defined in embodiment E.2, which is a compound (I-1)

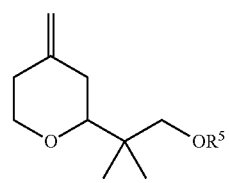

(I-1)

i.e. a compound of the formula (I) in which $R^2$ together with $R^1$ represents a double bond and $R^3$ and $R^4$ are hydrogen.

E.4. The compound as defined in embodiment E.2, which is a compound (I-2)

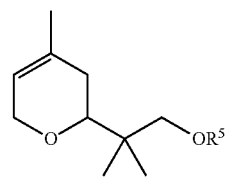

(I-2)

i.e. a compound of the formula (I) in which $R^3$ together with $R^1$ represents a double bond and $R^2$ and $R^4$ are hydrogen.

E.5. The compound as defined in embodiment E.2, which is a compound (I-3)

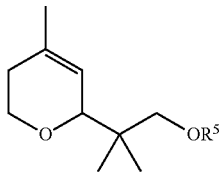

(I-3)

i.e. a compound of the formula (I) in which $R^4$ together with $R^1$ represents a double bond and $R^2$ and $R^3$ are hydrogen.

E.6. The compound as defined in embodiment E.2, which is a mixture containing at least two of compounds (I-1), (I-2) and (I-3)

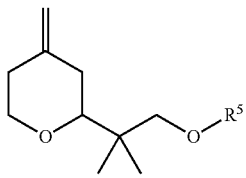

(I-1)

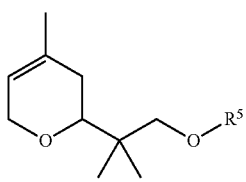

(I-2)

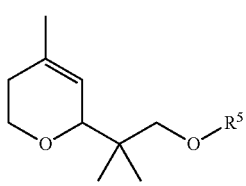

(I-3)

where the compound (I-1) is a compound of the formula (I) in which $R^2$ together with $R^1$ represents a double bond and $R^3$ and $R^4$ are hydrogen; the compound (I-2) is a compound of the formula (I) in which $R^3$ together with $R^1$ represents a double bond and $R^2$ and $R^4$ are hydrogen; and the compound (I-3) is a compound of the formula (I) in which $R^4$ together with $R^1$ represents a double bond and $R^2$ and $R^3$ are hydrogen.

E.7. The compound as defined in embodiment E.6, which is a mixture containing the compound (I-1), the compound (I-3) and optionally also the compound (I-2).

E.8. The compound as defined in embodiment E.6, which is a mixture containing the compound (I-2), the compound (I-3) and optionally also the compound (I-1).

E.9. The compound as defined in any of embodiment E.6 to E.8, and which is a mixture containing all three compounds (I-1), (I-2) and (I-3).

E.10. The compound as defined in any of embodiments E.6, E.7 or E.9, which is a mixture in which compound (I-1) predominates and is present in an amount of at least 35% by weight, where each of the compounds (I-2) and (I-3) are present in an amount of less than 35% by weight, relative to the total weight of compounds (I-1), (I-2) and (I-3).

E.11. The compound as defined in embodiment E.10, where compound (I-1) is present in an amount of at least 40% by weight, where each of the compounds (I-2) and (I-3) are present in an amount of less than 40% by weight, relative to the total weight of compounds (I-1), (I-2) and (I-3).

E.12. The compound as defined in any of embodiments E.6, E.8 or E.9, which is a mixture in which compound (I-2) predominates and is present in an amount of at least 40% by weight, where each of the compounds (I-1) and (I-3) are present in an amount of less than 40% by weight, relative to the total weight of compounds (I-1), (I-2) and (I-3).

E.13. The compound as defined in embodiment E.12, where compound (I-2) is present in an amount of at least 45% by weight, where each of the compounds (I-1) and (I-3) are present in an amount of less than 45% by weight, relative to the total weight of compounds (I-1), (I-2) and (I-3).

E.14. The compound as defined in any of embodiments E.6 to E.13, where in all compounds (I-1), (I-2) and (I-3) present in the mixture $R^5$ has the same meaning.

E.15. The compound as defined in embodiment E.1, wherein $R^1$, $R^2$, $R^3$ and $R^4$ are hydrogen.

E.16. The compound as defined in any of the preceding embodiments, which is a mixture containing at least one compound (I) and one or both of the compounds of the formula (II.1) and/or (II.2).

E.17. The compound as defined in embodiment E.16, which is a mixture containing at least one of the compounds (I-1), (I-2) and/or (I-3), and further containing one or both of the compounds of the formula (II.1) and/or (II.2).

E.18. The compound as defined in embodiment E.17, where the mixture contains compound (I-1), compound (I-3) and optionally also compound (I-2) as compounds (I), and further contains one or both of the compounds of the formula (II.1) and/or (II.2).

E.19. The compound as defined in any of embodiments E.16 to E.18, where in the mixture, the compound(s) (I) predominate.

E.20. The compound as defined in embodiment E.19, where in the mixture the one or more compounds (I) are present in an overall amount of at least 60% by weight, relative to the total weight of all compounds (I), (II.1) and (II.2).

E.21. The compound as defined in embodiment E.20, where the one or more compounds (I) are present in an overall amount of at least 65% by weight, relative to the total weight of all compounds (I), (II.1) and (II.2).

E.22. The compound as defined in any of the preceding embodiments, where in case that the compound (I) is a mixture of different compounds (I) which optionally also contains one or both of compounds (II.1) and/or (II.2), or is a mixture of a compound (I) with one or both of compounds (II.1) and/or (II.2), in all compounds (I), (II.1) and (II.2) present in the mixture $R^5$ has the same meaning.

E.23. The compound as defined in any of embodiments E.16 to E.21, where in all compounds (I), (II.1) and (II.2) present in the mixture $R^5$ has the same meaning.

E.24. The compound as defined in any of the preceding embodiments, where $R^5$ is $C_1$-$C_4$-alkyl.

E.25. The compound as defined in embodiment E.24, where $R^5$ is methyl or ethyl.

E.26. The compound as defined in embodiment E.25, where $R^5$ is methyl.

E.27. The compound as defined in any of embodiments E.1 to E.23, where $R^5$ is hydrogen.

E.28. The compound as defined in any of embodiments E.1 to E.23, where $R^5$ is —C(=O)—$R^6$; where $R^6$ is hydrogen or $C_1$-$C_4$-alkyl.

E.29. The compound as defined in embodiment E.28, where $R^6$ is methyl or ethyl.

E.30. The compound as defined in embodiment E.29, where $R^6$ is methyl.

E.31. Composition comprising a compound of formula (I), a mixture thereof [i.e. a mixture of different compounds of the formula (I)], a stereoisomer thereof, a mixture of stereoisomers thereof or a mixture of at least one compound of the formula (I) with one or both of the compounds of the formula (II.1) and/or (II.2) as defined in any of embodiments E.1 to E.30, and at least one further component selected from the group consisting of aroma chemicals different from compounds (I), (II.1) and (II.2), non-aroma chemical carriers, anti-oxidants and deodorant-active agents.

E.32. The composition according to embodiment E.31, where the at least one further component is selected from the group consisting of aroma chemicals different from compounds (I), (II.1) and (II.2), surfactants, oil components, solvents, anti-oxidants and deodorant-active agents.

E.33. The composition according to any of embodiments E.31 or E.32, comprising at least one further aroma chemical selected from the group consisting of geranyl acetate (3,7-dimethyl-2,6 octadien-1yl acetate), alpha-hexylcinnamaldehyde, 2-phenoxyethyl isobutyrate (Phenirat[1]), dihydromyrcenol (2,6-dimethyl-7-octen-2-ol), methyl dihydrojasmonate (preferably with a content of cis isomer of more than 60 wt. %) (Hedione[9], Hedione HC[9]), 4,6,6,7,8,8-hexamethyl-1,3,4,6,7,8-hexahydrocyclopenta[g]benzopyran (Galaxolid[3]), tetrahydrolinalool (3,7-dimethyloctan-3-ol), ethyllinalool, benzyl salicylate, 2-methyl-3-(4-tert-butylphenyl)propanal (Lysmeral[2]), cinnamyl alcohol, 4,7-methano-3a,4,5,6,7,7a-hexahydro-5-indenyl acetate and/or 4,7-methano-3a,4,5,6,7,7a-hexahydro-6-indenyl acetate (Herbaflorat[1]), citronellol, citronellyl acetate, tetrahydrogeraniol, vanillin, linalyl acetate, styrolyl acetate (1-phenylethyl acetate), octahydro-2,3,8,8-tetramethyl-2-acetonaphthone and/or 2-acetyl-1,2,3,4,6,7,8-octahydro-2,3,8,8-tetramethylnaphthalene (Iso E Super[3]), hexyl salicylate, 4-tert-butylcyclohexyl acetate (Oryclone[1]), 2-tert-butylcyclohexyl acetate (Agrumex HC[1]), alpha-ionone (4-(2,2,6-trimethyl-2-cyclohexen-1-yl)-3-buten-2-one), n-alpha-methylionone, alpha-isomethylionone, coumarin, terpinyl acetate, 2-phenylethyl alcohol, 4-(4-hydroxy-4-methylpentyl)-3-cyclohexene-carboxaldehyde (Lyral[3]), alpha-amyl-cinnamaldehyde, ethylene brassylate, (E)- and/or (Z)-3-methylcyclopentadec-5-enone (Muscenon[9]), 15-pentadec-11-enolide and/or 15-pentadec-12-enolide (Globalide[1]), 15-cyclo-pentadecanolide (Macrolide[1]), 1-(5,6,7,8-tetrahydro-3,5,5,6,8,8-hexamethyl-2-naphthalenyl)ethanone (Tonalid[10]), 2-isobutyl-4-methyltetrahydro-2H-pyran-4-ol (Florol[9]), 2-ethyl-4-(2,2,3-trimethyl-3-cyclopenten-1-yl)-2-buten-1-ol (Sandolen[1]), cis-3-hexenyl acetate, trans-3-hexenyl acetate, trans-2/cis-6-nonadienol, 2,4-dimethyl-3-cyclohexenecarboxaldehyde (Vertocitral[1]), 2,4,4,7-tetramethyloct-6-en-3-one (Claritone[1]), 2,6-dimethyl-5-hepten-1-al (Melonal[2]), borneol, 3-(3-isopropylphenyl) butanal (Florhydral[2]), 2-methyl-3-(3,4-methylenedioxyphenyl)propanal (Helional[3]), 3-(4-ethylphenyl)-2,2-dimethylpropanal (Florazon[1]), 7-methyl-2H-1,5-benzodioxepin-3(4H)-one (Calone), 3,3,5-trimethylcyclohexyl acetate (preferably with a content of cis isomers of 70 wt. %) or more, 2,5,5-trimethyl-1,2,3,4,4a,5,6,7-octahydronaphthalen-2-ol (Ambrinol S[1]), 3-(4-tert-butylphenyl)-propanal (Bourgeonal[4]), ethyl 2-methylpentanoate (Manzanate[4]), ethoxymethoxycyclododecane (Amberwood[1]), 2,4-dimethyl-4,4a,5,9b-tetrahydroindeno[1,2-d][1,3]dioxine (Magnolan[1]), (2-tert-butylcyclohexyl) acetate (Verdox[3]) and 3-[5,5,6-trimethylbicyclo[2.2.1]hept-2-yl]cyclohexan-1-ol (Sandela[4]).

E.34. The composition according to any of embodiments E.31 or E.32, comprising at least one further aroma chemical selected from the group consisting of methyl benzoate, benzyl acetate, geranyl acetate, 2-isobutyl-4-methyltetrahydro-2H-pyran-4-ol and linalool.

E.35. The composition according to any of embodiments E.31 or E.32, comprising at least one further aroma chemical selected from the group consisting of ethylvanillin, vanillin, 2,5-dimethyl-4-hydroxy-2H-furan-3-one (furaneol) or 3-hydroxy-2-methyl-4H-pyran-4-one (maltol).

E.36. The composition according to any of embodiments E.31 to E.35, comprising at least one solvent selected from the group consisting of ethanol, isopropanol, diethylene glycol monoethyl ether, glycerol, propylene glycol, 1,2-butylene glycol, dipropylene glycol, triethyl citrate and isopropyl myristate.

E.37. The composition according to any of embodiments E.31 to E.36, comprising at least one deodorant-active agent selected from the groups consisting of anti-perspirants, esterase inhibitors and antibacterial agents.

E.38. The composition according to embodiment E.37, wherein the anti-perspirant is selected from selected from the group consisting of aluminium chloride, aluminium chlorohydrate, aluminium dichlorohydrate, aluminium sesquichlorohydrate, aluminium hydroxyallantoinate, aluminium chloride tartrate, aluminium zirconium trichlorohydrate, aluminium zirconium tetrachlorohydrate and aluminium zirconium pentachlorohydrate.

E.39. The composition according to any of embodiments E.37 or E.38, wherein the esterase inhibitor is selected from the group consisting of trimethyl citrate, tripropyl citrate, triisopropyl citrate, tributyl citrate triethyl citrate, lanosterol, cholesterol, campesterol, stigmasterol, sitosterol sulfate, sitosterol phosphate, glutaric acid, glutaric acid monoethyl ester, glutaric acid diethyl ester, adipic acid, adipic acid monoethyl ester, adipic acid diethyl ester, malonic acid, malonic acid diethyl ester, citric acid, malic acid, tartaric acid, tartaric acid diethyl ester and zinc glycinate.

E.40. The composition according to any of embodiments E.37 to E.39, wherein the antibacterial agent is selected from the group consisting of chitosan, phenoxyethanol, 5-Chloro-2-(2,4-dichlorophenoxy)-phenol, 4-hydroxybenzoic acid and salts and esters thereof, N-(4-chlorophenyl)-N'-(3,4-dichlorophenyl)-urea, 2,4,4'-trichloro-2'-hydroxydiphenylether (triclosan), 4-chloro-3,5-dimethylphenol, 2,2'-methylene-bis-(6-bromo-4-chlorophenol), 3-methyl-4-(1-methylethyl)-phenol, 2-benzyl-4-chlorophenol, 3-(4-chlorophenoxy)-propane-1,2-diol, 3-iodo-2-propinyl butyl carbamate, chlorhexidine, 3,4,4'-trichlorocarbanilide (TTC), phenoxyethanol, glycerol monocaprate, glycerol monocaprylate, glycerol monolaurate (GML), diglycerol monocaprate (DMC), salicylic acid-N-alkylamides.

E.41. The composition according to any of embodiments E.31 to E.40, comprising at least one surfactant selected from the group consisting of anionic, non-ionic, cationic, amphoteric and zwitterionic surfactants.

E.42. The composition according to embodiments E.41, wherein the at least one surfactant is an anionic surfactant.

E.43. The composition according to any of embodiments E.31 to E.42, comprising at least one anti-oxidant selected from the group consisting of pentaerythrityl, tetra-di-t-butyl hydroxyhydrocinnamate, nordihydroguaiaretic acid, ferulic acid, resveratrol, propyl gallate, butylhydroxytoluene (BHT), butylhydroxyanisole (BHA), ascorbyl palmitate and tocopherol.

E.44. The composition according to any of embodiments E.31 to E.43, comprising at least one oil component selected from the group consisting of Guerbet alcohols based on fatty alcohols containing 6 to 18 carbon atoms, myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate, erucyl erucate, esters of $C_{18}$-$C_{38}$ alkyl-hydroxycarboxylic acids with linear or branched $C_6$-$C_{22}$ fatty alcohols, esters of linear and/or branched fatty acids with polyhydric alcohols, esters of $C_6$-$C_{22}$ fatty alcohols or Guerbet alcohols with aromatic carboxylic acids, esters of dicarboxylic acids with polyols containing 2 to 10 carbon atoms and 2 to 6 hydroxyl groups, vegetable oils, branched primary alcohols, substituted cyclohexanes, linear and branched $C_6$-$C_{22}$ fatty alcohol carbonates, Guerbet carbonates based on fatty alcohols containing 6 to 18 carbon atoms, esters of benzoic acid with linear and/or branched $C_6$ to $C_{22}$ alcohols, linear or branched, symmetrical or nonsymmetrical dialkyl ethers containing 6 to 22 carbon atoms per alkyl group, ring opening products of epoxidized fatty acid esters with polyols, hydrocarbons and mixtures thereof.

E.45. The composition according to any of embodiment E.31 to E.44, which is selected from the group consisting of perfume compositions, body care compositions, products for oral or dental hygiene, hygiene articles, cleaning compositions, textile detergent compositions, compositions for scent dispensers, foods, food supplements, pharmaceutical compositions and crop protection compositions.

E.46. The use of a compound of the formula (I), of a mixture thereof [i.e. of a mixture of different compounds of the formula (I)], a stereoisomer thereof, a mixture of stereoisomers thereof or a mixture of at least one compound of the formula (I) with one or both of the compounds of the formula (II.1) and/or (II.2) as defined in any of embodiments E.1 to E.30, as an aroma chemical.

E.47. The use as defined in embodiment 46, for imparting an olfactory impression.

E.48. The use as defined in embodiment 47, as a fragrance.

E.49. The use of a compound of the formula (I), a mixture thereof [i.e. of a mixture of different compounds of the formula (I)], a stereoisomer thereof, a mixture of stereoisomers thereof or a mixture of at least one compound of the formula (I) with one or both of the compounds of the formula (II.1) and/or (II.2) as defined in any one of embodiments E.1 to E.30, for modifying and/or enhancing the aroma of a composition.

E.50. The use as defined in embodiment 49, for modifying and/or enhancing the fragrance impression of a composition.

E.51. The use as defined in embodiment 50, for modifying and/or enhancing the fragrance impression of a fragranced composition.

E.52. The use as defined in embodiment 51, for modifying the fragrance impression/scent character of a fragranced ready-to-use composition.

E.53. The use according to any of embodiments E.46 to E.52, in a composition selected from perfume compositions, body care compositions, products for oral or dental hygiene, hygiene articles, cleaning compositions, textile detergent compositions, compositions for scent dispensers, foods, food supplements, pharmaceutical compositions and crop protection compositions.

E.54. A method of preparing an aroma chemical composition, comprising incorporating at least one compound of formula (I), a stereoisomer thereof, a mixture of stereoisomers thereof or a mixture of at least one compound of the formula (I) with one or both of the compounds of the formula (II.1) and/or (II.2) as defined in any of embodiments E.1 to E.30 into the target composition, resulting in an aroma chemical composition.

E.55. The method as defined in embodiment E.53, for preparing a fragranced composition.

E.56. The method as defined in embodiment E.54, for preparing a fragranced ready-to-use composition, comprising incorporating at least one compound of formula (I), a stereoisomer thereof, a mixture of stereoisomers thereof or a mixture of at least one compound of the formula (I) with one or both of the compounds of the formula (II.1) and/or (II.2) as defined in any of embodiments E.1 to E.30 into a ready-to-use composition.

E.57. A method of preparing an aroma chemical composition, comprising mixing at least one compound of formula (I), a stereoisomer thereof, a mixture of stereoisomers thereof or a mixture of at least one compound of the formula (I) with one or both of the compounds of the formula (II.1) and/or (II.2) as defined in any of embodiments E.1 to E.30 with at least one aroma chemical different from compounds (I), (II.1) and (II.2) and/or with at least one non-aroma chemical carrier and/or with at least one antioxidant and/or with at least one deodorant-active agent.

E.58. The method as defined in embodiment E.56, where the at least one aroma chemical different from compounds (I), (II.1) and (II.2), the at least one non-aroma chemical carrier, the at least one antioxidant and the at least one deodorant-active agent are as defined in embodiments E.31 to E.44.

E.59. A method of modifying and/or enhancing the aroma of a composition, comprising incorporating at least one compound of formula (I), optionally in admixture with one or both of the compounds of the formula (II.1) and/or (II.2), a stereoisomer thereof or a mixture of stereoisomers thereof, into said composition.

E.60. The method of embodiment E.58, for modifying and/or enhancing the fragrance impression of an aroma composition.

E.61. The method of embodiment E.59, for modifying and/or enhancing the fragrance impression of a fragranced composition.

E.62. The method of embodiment E.60, for modifying and/or enhancing the fragrance impression of a fragranced ready-to-use composition, comprising incorporating at least one compound of formula (I), optionally in admixture with one or both of the compounds of the formula (II.1) and/or (II.2), a stereoisomer thereof or a mixture of stereoisomers thereof, into a ready-to-use composition.

E.63. The method as defined in any of embodiments E.54 to E.62, where the composition is selected from the group consisting of perfume compositions, body care compositions, products for oral or dental hygiene, hygiene articles, cleaning compositions, textile detergent compositions, compositions for scent dispensers, foods, food supplements, pharmaceutical compositions and crop protection compositions.

E.64. A method for preparing a compound of the formula (I), a mixture thereof [i.e. a mixture of different compounds of the formula (I)], a stereoisomer thereof, a mixture of stereoisomers thereof or a mixture of at least one compound of the formula (I) with one or both of the compounds of the formula (II.1) and/or (II.2) as defined in any of embodiments E.1 to E.30, which method comprises (a) reacting 3-methylbut-3-en-1-ol (isoprenol) with 3-hydroxy-2,2-dimethyl-propanal (hydroxypivalinaldehyde) in acidic medium to obtain a reaction mixture containing a compound of the formula (I') and optionally also one or both of the compounds of the formula (II'.1) and/or (II'.2)

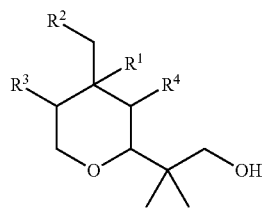
(I')

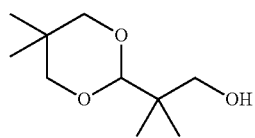
(II'.1)

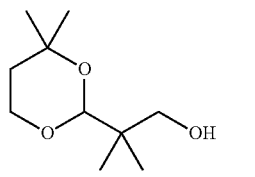
(II'.2)

wherein one of $R^2$, $R^3$ or $R^4$ together with $R^1$ represents a double bond; and the others of $R^2$, $R^3$ or $R^4$ are hydrogen;

(b) optionally isolating the compound of the formula (I') and, if present, the compounds (II'-1) and (II'-2) from the reaction mixture obtained in step (a) or enriching it in the reaction mixture obtained in step (a);

(c) if a compound of the formula (I) or a compound of the formula (I'), wherein $R^1$, $R^2$, $R^3$ and $R^4$ are hydrogen, is to be prepared: subjecting the reaction mixture obtained in step (a) or the product obtained in step (b) to a hydrogenation reaction to obtain a compound of the formula (I') wherein $R^1$, $R^2$, $R^3$ and $R^4$ are hydrogen;

(d) if a compound of the formula (I) is to be prepared in which $R^5$ is not hydrogen: subjecting the reaction mixture obtained in step (a) or the product obtained in step (b) or the product obtained in step (c) to an etherification or esterification reaction;

(e) if a compound of the formula (I), wherein $R^1$, $R^2$, $R^3$ and $R^4$ are hydrogen and $R^5$ is not hydrogen, is to be prepared and step (c) has not been carried out: subjecting the product obtained in step (d) to a hydrogenation reaction; and (f) optionally subjecting the product obtained in step (b) or step (c) or step (d) or step (e) to a purification step.

E.65. A method for preparing a compound of the formula (I) wherein $R^5$ is selected from the group consisting of $C_1$-$C_4$-alkyl and —C(=O)—$R^6$; a mixture thereof [i.e. a mixture of different compounds of the formula (I)], a stereoisomer thereof or a mixture of stereoisomers thereof as defined in any of embodiments E.1 to E.30, which method comprises (i) subjecting 3-hydroxy-2,2-dimethyl-propanal (hydroxypivalinaldehyde) to an etherification or esterification reaction to obtain a reaction mixture containing a compound of the formula 3

3 wherein $R^{5a}$ is selected from the group consisting of $C_1$-$C_4$-alkyl and —C(=O)—$R^6$;

(ii) optionally isolating the compound of the formula 3 from the reaction mixture obtained in step (i) or enriching it in the reaction mixture obtained in step (i);

(iii) reacting the reaction mixture obtained in step (i) or the product obtained in step (ii) with 3-methylbut-3-en-1-ol (isoprenol) in the presence of a $BF_3$ source to obtain a reaction mixture containing a compound of the formula (I) wherein $R^5$ is selected from the group consisting of $C_1$-$C_4$-alkyl and —C(=O)—$R^6$;

(iv) if a compound of the formula (I), wherein $R^1$, $R^2$, $R^3$ and $R^4$ are hydrogen and $R^5$ is selected from the group consisting of $C_1$-$C_4$-alkyl and —C(=O)—$R^6$, is to be prepared: subjecting the product obtained in step (iii) to a hydrogenation reaction;

(v) optionally subjecting the product obtained in step (iii) or step (iv) to a purification step.

E.66. The product obtainable with the method of any of embodiments E.63 to E.65.

Compounds (I)

In one embodiment, in compounds (I) one of $R^2$, $R^3$ or $R^4$ together with $R^1$ represents a double bond and the others of $R^2$, $R^3$ or $R^4$ are hydrogen. In another embodiment, in compounds (I) $R^1$, $R^2$, $R^3$ and $R^4$ are hydrogen.

Preferably, however, in compounds (I) one of $R^2$, $R^3$ or $R^4$ together with $R^1$ represents a double bond and the others of $R^2$, $R^3$ or $R^4$ are hydrogen.

In a more preferred embodiment, the compound (I) is a compound (I-1).

In another more preferred embodiment, the compound (I) is a compound (I-2).

In yet another more preferred embodiment, the compound (I) is a compound (I-3).

Among compounds (I-1), (I-2) and (I-3), even more preference is given to compounds (I-1) and (I-2), and specifically to compounds (I-1).

In another more preferred embodiment, the compound (I) is a mixture of two or more, specifically two or three, different compounds (I).

Compounds (I) wherein one of $R^2$, $R^3$ or $R^4$ together with $R^1$ represents a double bond and the others of $R^2$, $R^3$ or $R^4$ are hydrogen are available by synthetic methods which may yield a mixture containing at least two of compounds (I-1), (I-2) and (I-3). It is possible to separate this mixture into the single compounds. However, as it turned out, the mixtures, too, have very advantageous olfactory properties. It is therefore not necessary to separate the mixture into the different compounds (I). Accordingly, in a particular embodiment, the invention relates to a mixture containing at least two of compounds (I-1), (I-2) and (I-3). In a more particular embodiment, the invention relates to a mixture containing the compound (I-1), the compound (I-3) and optionally also the compound (I-2). Specifically, the invention relates to a mixture containing all three compounds (I-1), (I-2) and (I-3). In such mixtures containing at least two of the compounds (I-1), (I-2) and (I-3) as formed in the production process, as a matter of course $R^5$ has the same meaning in all compounds (I) present in the mixture; i.e. compounds (I-1), (I-2) and (I-3) are double bond isomers of each other.

In mixtures containing all three compounds (I-1), (I-2) and (I-3), generally either compound (I-1) or compound (I-2) predominates; i.e. is present in a higher amount than either of the two other compounds (but not necessarily higher than the sum of the two other compounds). In a particular embodiment, compound (I-1) predominates and is present in an amount of at least 35% by weight (where of course each of the compounds (I-2) and (I-3) are present in an amount of less than 35% by weight), preferably of at least 40% by weight (where of course each of the compounds (I-2) and (I-3) are present in an amount of less than 40% by weight), relative to the total weight of compounds (I-1), (I-2) and (I-3). In another particular embodiment, compound (I-2) predominates and is present in an amount of at least 40% by weight (where of course each of the compounds (I-1) and (I-3) are present in an amount of less than 40% by weight), preferably of at least 45% by weight (where of course each of the compounds (I-1) and (I-3) are present in an amount of less than 45% by weight), relative to the total weight of compounds (I-1), (I-2) and (I-3). Mixtures in which compound (I-1) predominates generally have a more intensive odor than mixtures in which compound (I-2) predominates. However, in some applications a less intensive odor profile may be advantageous, so that the latter mixtures are also interesting.

Compounds (I) are i.a. available by the Prins reaction of isoprenol with hydroxypivalinaldehyde (for details see below description of the process). Depending on the reaction conditions, the desired formation of the dihydro- or tetrahydropyran ring competes with the formation of the corresponding cyclic acetal(s) (1,3-dioxans carrying in 2-position the isobutyl-derived group —C(CH$_3$)$_2$—CH$_2$—OR$^5$). Consequently, this method may yield a mixture containing at least one compound (I) [the at least one compound (I) most often being a mixture containing at least two of the compounds (I-1), (I-2) and (I-3)] and at least one of the corresponding cyclic acetals (II.1) and (II.2). "Corresponding" acetals means that $R^5$ in the acetal(s) (II.1) and/or (II.2) has the same meaning as in the one or more compounds (I) present in the mixture. Seeing that the product of the Prins reaction may be further subjected to an etherification or esterification reaction, due to incomplete reaction the obtained mixture may also contain some alcohol where $R^5$ in the compound(s) (I) and/or (II.1) and/or (II.2) remains hydrogen.

It is possible to separate the compound(s) (I) from the acetals (II.1) and (II.2). However, as it turned out, these mixtures, too, have very advantageous olfactory properties. It is therefore not necessary to carry out such a separation. In the mixture, the compound(s) (I) predominate. This means that in a mixture containing besides the one or more compounds (I) also one or both of the acetals (II.1) and (II.2), the one or more compounds (I) are present in an overall amount of more than 50% by weight, relative to the total weight of all compounds (I), (II.1) and (II.2). Preferably, the one or more compounds (I) are present in an overall amount of at least 60% by weight, in particular of at least 65% by weight, relative to the total weight of all compounds (I), (II.1) and (II.2).

In a preferred embodiment, in compounds (I), $R^5$ is $C_1$-$C_4$-alkyl. More preferably, $R^5$ is methyl or ethyl, in particular methyl.

In another preferred embodiment, in compounds (I), $R^5$ is hydrogen.

In yet another preferred embodiment, in compounds (I), $R^5$ is —C(=O)—R$^6$; where $R^6$ is hydrogen or $C_1$-$C_4$-alkyl. More preferably, $R^6$ is methyl or ethyl, in particular methyl.

In one particular embodiment (embodiment 1.1), the compound (I) is a compound (I-1) and $R^5$ is H.

In another particular embodiment (embodiment 1.2), the compound (I) is a compound (I-2) and $R^5$ is H.

In another particular embodiment (embodiment 1.3), the compound (I) is a compound (I-3) and $R^5$ is H.

In another particular embodiment (embodiment 1.4), the compound (I) is a mixture of at least two of the compounds (I-1), (I-2) and (I-3), where in each case $R^5$ is H.

In another particular embodiment (embodiment 1.5), the compound (I) is a mixture of the compound (I-1) and one or both of the compounds (I-2) and (I-3), where in each case $R^5$ is H.

In another particular embodiment (embodiment 1.6), the compound (I) is a mixture of the compound (I-2) and one or both of the compounds (I-1) and (I-3), where in each case $R^5$ is H.

In another particular embodiment (embodiment 1.7), the compound (I) is a mixture of the compound (I-3) and one or both of the compounds (I-1) and (I-2), where in each case $R^5$ is H.

In another particular embodiment (embodiment 1.8), the compound (I) is a mixture of the compound (I-1), one or both of the compounds (I-2) and (I-3) and one or both of the compounds (II.1) and (II.2), where in each case $R^5$ is H.

In another particular embodiment (embodiment 1.9), the compound (I) is a mixture of the compound (I-2), one or both of the compounds (I-1) and (I-3) and one or both of the compounds (II.1) and (II.2), where in each case $R^5$ is H.

In another particular embodiment (embodiment 1.10), the compound (I) is a mixture of the compound (I-3), one or both of the compounds (I-1) and (I-2) and one or both of the compounds (II.1) and (II.2), where in each case $R^5$ is H.

In another particular embodiment (embodiment 1.11), the compound (I) is a compound (I) in which $R^1$, $R^2$, $R^3$ and $R^4$ are hydrogen and $R^5$ is H.

In another particular embodiment (embodiment 1.12), the compound (I) is a mixture of the compound (I) in which $R^1$, $R^2$, $R^3$ and $R^4$ are hydrogen and one or both of the compounds (II.1) and (II.2), where in each case $R^5$ is H.

In another particular embodiment (embodiment 2.1), the compound (I) is a compound (I-1) and $R^5$ is methyl.

In another particular embodiment (embodiment 2.2), the compound (I) is a compound (I-2) and $R^5$ is methyl.

In another particular embodiment (embodiment 2.3), the compound (I) is a compound (I-3) and $R^5$ is methyl.

In another particular embodiment (embodiment 2.4), the compound (I) is a mixture of at least two of the compounds (I-1), (I-2) and (I-3), where in each case $R^5$ is methyl.

In another particular embodiment (embodiment 2.5), the compound (I) is a mixture of the compound (I-1) and one or both of the compounds (I-2) and (I-3), where in each case $R^5$ is methyl.

In another particular embodiment (embodiment 2.6), the compound (I) is a mixture of the compound (I-2) and one or both of the compounds (I-1) and (I-3), where in each case $R^5$ is methyl.

In another particular embodiment (embodiment 2.7), the compound (I) is a mixture of the compound (I-3) and one or both of the compounds (I-1) and (I-2), where in each case $R^5$ is methyl.

In another particular embodiment (embodiment 2.8), the compound (I) is a mixture of the compound (I-1), one or both of the compounds (I-2) and (I-3) and one or both of the compounds (II.1) and (II.2), where in each case $R^5$ is methyl.

In another particular embodiment (embodiment 2.9), the compound (I) is a mixture of the compound (I-2), one or both of the compounds (I-1) and (I-3) and one or both of the compounds (II.1) and (II.2), where in each case $R^5$ is methyl.

In another particular embodiment (embodiment 2.10), the compound (I) is a mixture of the compound (I-3), one or both of the compounds (I-1) and (I-2) and one or both of the compounds (II.1) and (II.2), where in each case $R^5$ is methyl.

In another particular embodiment (embodiment 2.11), the compound (I) is a compound (I) in which $R^1$, $R^2$, $R^3$ and $R^4$ are hydrogen and $R^5$ is methyl.

In another particular embodiment (embodiment 2.12), the compound (I) is a mixture of the compound (I) in which $R^1$, $R^2$, $R^3$ and $R^4$ are hydrogen and one or both of the compounds (II.1) and (II.2), where in each case $R^5$ is methyl.

In another particular embodiment (embodiment 3.1), the compound (I) is a compound (I-1) and $R^5$ is ethyl.

In another particular embodiment (embodiment 3.2), the compound (I) is a compound (I-2) and $R^5$ is ethyl.

In another particular embodiment (embodiment 3.3), the compound (I) is a compound (I-3) and $R^5$ is ethyl.

In another particular embodiment (embodiment 3.4), the compound (I) is a mixture of at least two of the compounds (I-1), (I-2) and (I-3), where in each case $R^5$ is ethyl.

In another particular embodiment (embodiment 3.5), the compound (I) is a mixture of the compound (I-1) and one or both of the compounds (I-2) and (I-3), where in each case $R^5$ is ethyl.

In another particular embodiment (embodiment 3.6), the compound (I) is a mixture of the compound (I-2) and one or both of the compounds (I-1) and (I-3), where in each case $R^5$ is ethyl.

In another particular embodiment (embodiment 3.7), the compound (I) is a mixture of the compound (I-3) and one or both of the compounds (I-1) and (I-2), where in each case $R^5$ is ethyl.

In another particular embodiment (embodiment 3.8), the compound (I) is a mixture of the compound (I-1), one or both of the compounds (I-2) and (I-3) and one or both of the compounds (II.1) and (II.2), where in each case $R^5$ is ethyl.

In another particular embodiment (embodiment 3.9), the compound (I) is a mixture of the compound (I-2), one or both of the compounds (I-1) and (I-3) and one or both of the compounds (II.1) and (II.2), where in each case $R^5$ is ethyl.

In another particular embodiment (embodiment 3.10), the compound (I) is a mixture of the compound (I-3), one or both of the compounds (I-1) and (I-2) and one or both of the compounds (II.1) and (II.2), where in each case $R^5$ is ethyl.

In another particular embodiment (embodiment 3.11), the compound (I) is a compound (I) in which $R^1$, $R^2$, $R^3$ and $R^4$ are hydrogen and $R^5$ is ethyl.

In another particular embodiment (embodiment 3.12), the compound (I) is a mixture of the compound (I) in which $R^1$, $R^2$, $R^3$ and $R^4$ are hydrogen and one or both of the compounds (II.1) and (II.2), where in each case $R^5$ is ethyl.

In another particular embodiment (embodiment 4.1), the compound (I) is a compound (I-1) and $R^5$ is —C(=O)—$CH_3$.

In another particular embodiment (embodiment 4.2), the compound (I) is a compound (I-2) and $R^5$ is —C(=O)—$CH_3$.

In another particular embodiment (embodiment 4.3), the compound (I) is a compound (I-3) and $R^5$ is —C(=O)—$CH_3$.

In another particular embodiment (embodiment 4.4), the compound (I) is a mixture of at least two of the compounds (I-1), (I-2) and (I-3), where in each case $R^5$ is —C(=O)—$CH_3$.

In another particular embodiment (embodiment 4.5), the compound (I) is a mixture of the compound (I-1) and one or both of the compounds (I-2) and (I-3), where in each case $R^5$ is —C(=O)—$CH_3$.

In another particular embodiment (embodiment 4.6), the compound (I) is a mixture of the compound (I-2) and one or both of the compounds (I-1) and (I-3), where in each case $R^5$ is —C(=O)—$CH_3$.

In another particular embodiment (embodiment 4.7), the compound (I) is a mixture of the compound (I-3) and one or both of the compounds (I-1) and (I-2), where in each case $R^5$ is —C(=O)—$CH_3$.

In another particular embodiment (embodiment 4.8), the compound (I) is a mixture of the compound (I-1), one or both of the compounds (I-2) and (I-3) and one or both of the compounds (II.1) and (II.2), where in each case $R^5$ is —C(=O)—$CH_3$.

In another particular embodiment (embodiment 4.9), the compound (I) is a mixture of the compound (I-2), one or both of the compounds (I-1) and (I-3) and one or both of the compounds (II.1) and (II.2), where in each case $R^5$ is —C(=O)—$CH_3$.

In another particular embodiment (embodiment 4.10), the compound (I) is a mixture of the compound (I-3), one or both of the compounds (I-1) and (I-2) and one or both of the compounds (II.1) and (II.2), where in each case $R^5$ is —C(=O)—$CH_3$.

In another particular embodiment (embodiment 4.11), the compound (I) is a compound (I) in which $R^1$, $R^2$, $R^3$ and $R^4$ are hydrogen and $R^5$ is —C(=O)—$CH_3$.

In another particular embodiment (embodiment 4.12), the compound (I) is a mixture of the compound (I) in which $R^1$, $R^2$, $R^3$ and $R^4$ are hydrogen and one or both of the compounds (II.1) and (II.2), where in each case $R^5$ is —C(=O)—$CH_3$.

In another particular embodiment (embodiment 5.1), the compound (I) is a compound (I-1) and $R^5$ is —C(=O)—$CH_2CH_3$.

In another particular embodiment (embodiment 5.2), the compound (I) is a compound (I-2) and $R^5$ is —C(=O)—$CH_2CH_3$.

In another particular embodiment (embodiment 5.3), the compound (I) is a compound (I-3) and $R^5$ is —C(=O)—$CH_2CH_3$.

In another particular embodiment (embodiment 5.4), the compound (I) is a mixture of at least two of the compounds (I-1), (I-2) and (I-3), where in each case $R^5$ is —C(=O)$CH_2CH_3$.

In another particular embodiment (embodiment 5.5), the compound (I) is a mixture of the compound (I-1) and one or both of the compounds (I-2) and (I-3), where in each case $R^5$ is —C(=O)—$CH_2CH_3$.

In another particular embodiment (embodiment 5.6), the compound (I) is a mixture of the compound (I-2) and one or both of the compounds (I-1) and (I-3), where in each case $R^5$ is —C(=O)—CH$_2$CH$_3$.

In another particular embodiment (embodiment 5.7), the compound (I) is a mixture of the compound (I-3) and one or both of the compounds (I-1) and (I-2), where in each case $R^5$ is —C(=O)—CH$_2$CH$_3$.

In another particular embodiment (embodiment 5.8), the compound (I) is a mixture of the compound (I-1), one or both of the compounds (I-2) and (I-3) and one or both of the compounds (II.1) and (II.2), where in each case $R^5$ is —C(=O)—CH$_2$CH$_3$.

In another particular embodiment (embodiment 5.9), the compound (I) is a mixture of the compound (I-2), one or both of the compounds (I-1) and (I-3) and one or both of the compounds (II.1) and (II.2), where in each case $R^5$ is —C(=O)—CH$_2$CH$_3$.

In another particular embodiment (embodiment 5.10), the compound (I) is a mixture of the compound (I-3), one or both of the compounds (I-1) and (I-2) and one or both of the compounds (II.1) and (II.2), where in each case $R^5$ is —C(=O)—CH$_2$CH$_3$.

In another particular embodiment (embodiment 5.11), the compound (I) is a compound (I) in which $R^1$, $R^2$, $R^3$ and $R^4$ are hydrogen and $R^5$ is —C(=O)—CH$_2$CH$_3$.

In another particular embodiment (embodiment 5.12), the compound (I) is a mixture of the compound (I) in which $R^1$, $R^2$, $R^3$ and $R^4$ are hydrogen and one or both of the compounds (II.1) and (II.2), where in each case $R^5$ is —C(=O)—CH$_2$CH$_3$.

Among the above embodiments, preference is given to embodiments x.1 to x.6, x.8 and x.9. More preference is given to embodiments x.4 to x.6 and x.8 and in particular to embodiments x.5, x.6 and x.8. x. stands for the numerals 1. to 5. in the above embodiments 1.1 to 5.12.

Synthesis of Compounds (I)

The compounds of the formula (I) can be prepared by the methods as described below or in the synthesis descriptions of the working examples, or by standard methods of organic chemistry. The substituents, variables and indices are as defined above for formula (I), if not otherwise specified.

To be more precise, the compounds (I) can be prepared by standard methods for preparing cyclic ethers, e.g. by a Prins reaction including reacting isoprenol (3-methylbut-3-en-1-ol) 1 with 3-hydroxy-2,2-dimethyl-propanal (hydroxypivalinaldehyde) 2, as shown in scheme 1 below (method A). The reaction of 1 with 2 is generally carried out under acidic conditions. The reaction leads to alcohol compounds (I) wherein $R^5$ is H [named in the following compounds (I')] and wherein one of $R^2$, $R^3$ or $R^4$ together with $R^1$ represents a double bond; and the others of $R^2$, $R^3$ or $R^4$ are hydrogen. To obtain compounds (I) wherein $R^5$ is different from H, the alcohol is etherified or esterified. To obtain compounds (I) wherein $R^1$, $R^2$, $R^3$ and $R^4$ are hydrogen, either the compounds (I') wherein one of $R^2$, $R^3$ or $R^4$ together with $R^1$ represents a double bond and the others of $R^2$, $R^3$ or $R^4$ are hydrogen are subjected to a hydrogenation reaction and, if desired, the hydrogenation product is etherified or esterified to give compounds wherein $R^5$ is different from H, or the etherification or esterification products of the compound (I') wherein one of $R^2$, $R^3$ or $R^4$ together with $R^1$ represents a double bond and the others of $R^2$, $R^3$ or $R^4$ are hydrogen is subjected to a hydrogenation reaction.

Scheme 1

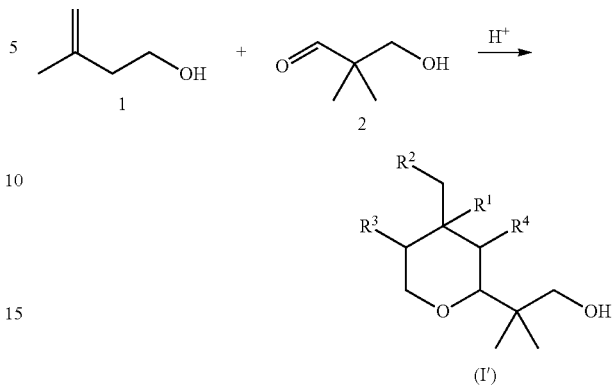

In the reaction product (I') of scheme 1, one of $R^2$, $R^3$ or $R^4$ together with $R^1$ represents a double bond and the others of $R^2$, $R^3$ or $R^4$ are hydrogen.

As already explained, depending on the reaction conditions, the compound(s) I' may be obtained in admixture with one or both acetals (II.1) and (II.2).

One aspect of the invention relates thus to a method for preparing a compound of the formula (I), a stereoisomer thereof, a mixture of stereoisomers thereof, a mixture of different compounds (I) or a mixture of at least one compound of the formula (I) with one or both of the compounds of the formula (II.1) and/or (II.2), as defined above, which method comprises:

(a) reacting 3-methylbut-3-en-1-ol (isoprenol) (1 in scheme 1 above) with 3-hydroxy-2,2-dimethyl-propanal (hydroxypivalinaldehyde) (2 in scheme 1 above) in acidic medium to obtain a reaction mixture containing one or more different compounds of the formula (I'), optionally in admixture with one or both of the compounds (II'-1) and (II'-2)

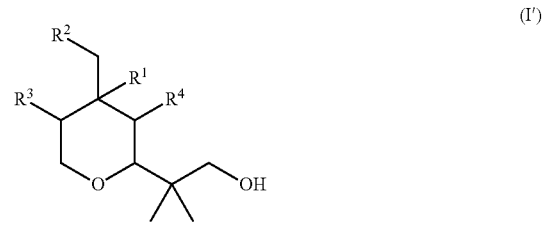

wherein one of $R^2$, $R^3$ or $R^4$ together with $R^1$ represents a double bond and the others of $R^2$, $R^3$ or $R^4$ are hydrogen;

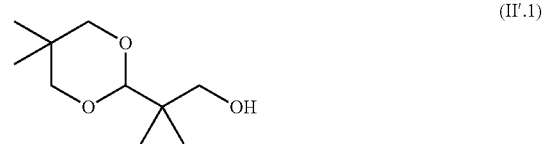

-continued

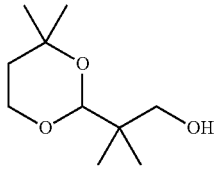

(II'.2)

(b) optionally isolating the one or more compounds of the formula (I') or the mixture of at least one compound of the formula (I') with one or both of the compounds of the formula (II'.1) and/or (II'.2) [if the latter are formed in step (a)] from the reaction mixture obtained in step (a) or enriching it/them in the reaction mixture obtained in step (a);

(c) if a compound of the formula (I) or a compound of the formula (I'), wherein $R^1$, $R^2$, $R^3$ and $R^4$ are hydrogen, is to be prepared: subjecting the reaction mixture obtained in step (a) or the product obtained in step (b) to a hydrogenation reaction to obtain a compound of the formula (I') wherein $R^1$, $R^2$, $R^3$ and $R^4$ are hydrogen;

(d) if a compound of the formula (I) is to be prepared in which $R^5$ is not hydrogen: subjecting the reaction mixture obtained in step (a) or the product obtained in step (b) or the product obtained in step (c) to an etherification or esterification reaction;

(e) if a compound of the formula (I), wherein $R^1$, $R^2$, $R^3$ and $R^4$ are hydrogen and $R^5$ is not hydrogen, is to be prepared and step (c) has not been carried out: subjecting the product obtained in step (d) to a hydrogenation reaction; and (d) optionally subjecting the product obtained in step (b) or step (c) or step (d) or step (e) to a purification step.

In step (a) (which is reflected in scheme 1) isoprenol 1 and hydroxypivalinaldehyde (HPA) 2 undergo an addition reaction in acidic medium to yield a compound of the formula (I'), in which $R^5$ is H and one of $R^2$, $R^3$ or $R^4$ together with $R^1$ represents a double bond while the others of $R^2$, $R^3$ or $R^4$ are hydrogen. This reaction may be regarded to belong to the group of reactions known in the art as Prins reactions. 1 and 2 are usually applied in a molar ratio of 0.9:1 to 1.5:1 and preferably in a molar ratio of 1:1 to 1.3:1. It is expedient to use 1 in slight excess is order to avoid the formation of acetals as side products which would be favoured if 2 were used in excess.

The acidic medium of step (a) is provided by carrying out the reaction in the presence of an acid, suitably a Brønsted acid.

The Brønsted acid used in the reaction may be any Brønsted acid known in the art and is preferably selected from strong Brønsted acids, such as hydrochloric acid, sulfuric acid, acetic acid, trifluoroacetic acid, methanesulfonic acid, p-toluenesulfonic acid, camphorsulfonic acid (to be more precise 10-camphorsulfonic acid) or strongly acidic cation exchange resins.

The term "strongly acidic cationic exchanger" refers to a cationic exchanger in the $H^+$ form which has strongly acidic groups. The strongly acidic groups are generally sulfonic acid groups; they are generally bonded to a polymer matrix, which can be e.g. gel-like and/or macroporous. Preference is given to styrene (co)polymers containing sulfonic acid groups, specifically to styrene-divinyl benzene copolymers containing sulfonic acid groups. Commercial examples for such cationic exchangers are Lewatit® (Lanxess), Purolite® (The Purolite Company), Dowex® (Dow Chemical Company), Amberlite® (Rohm and Haas Company), Amberlyst® (Rohm and Haas Company). Preferred strongly acidic cation exchangers are: Lewatit® K 1221, Lewatit® K 1461, Lewatit® K 2431, Lewatit® K 2620, Lewatit® K 2621, Lewatit® K 2629, Lewatit® K 2649, Amberlite® FPC 22, Amberlite® FPC 23, Amberlite® IR 120, Amberlyst® 131, Amberlyst® 15, Amberlyst® 31, Amberlyst® 35, Amberlyst® 36, Amberlyst® 39, Amberlyst® 46, Amberlyst® 70, Purolite® SGC650, Purolite® C100H, Purolite® C150H, Dowex® 50X8, Serdolit® red and Nation® NR-50. Specifically, resins of the Amberlyst® brand from Rohm and Haas, and very specifically Amberlyst® 131 is used. Alternatively, the cation exchanger can be a perfluorinated ion exchange resin, sold e.g. under the Nafion® brand of DuPont.

The Brønsted acid different from acidic cationic exchanger resins is generally used in catalytic amounts. For example, the Brønsted acid can be used in an amount of from 0.01 to 20 mol-%, preferably from 0.05 to 15 mol-%, in particular from 0.1 to 10 mol-%, relative to 1 mol of that starting compound 1 and 2 which is used in a smaller amount. If 1 and 2 are used in equimolar amounts, the percentage is of course relative to 1 mol of either of the starting compounds.

The amount of strongly acidic cation exchanger is not very critical, but yet for economic and processing aspects it is generally used in catalytic amounts. Usually, the strongly acidic cation exchanger is used in an amount of from about 5 up to about 40% by weight, preferably in an amount of from about 10 to about 40% by weight and particularly preferably in an amount of from about 15 to about 30% by weight, in each case based on the sum of the weights of 1 and 2. Here, the figures refer to the ready-to-use cation exchanger which is generally pretreated with water and accordingly can comprise amounts of up to about 70% by weight, preferably of about 30 to about 70% by weight and particularly preferably of about 40 to about 70% by weight of water. Particularly in the case of a discontinuous procedure, an additional addition of water when carrying out the process may therefore be superfluous. The specified strongly acidic cation exchangers can be used either individually or else in the form of mixtures.

Preferably, the Brønsted acid is selected from the group consisting of hydrochloric acid, sulfuric acid, acetic acid, trifluoroacetic acid, methanesulfonic acid, p-toluenesulfonic acid and 10-camphorsulfonic acid. In a specific embodiment, methanesulfonic acid or toluenesulfonic acid is used as acid.

If an acid different from acidic cationic exchangers is used in the reaction in step (a), the reaction is generally carried out in a suitable organic solvent that is inert under the reaction conditions of step (a). Suitable solvents are e.g. alkanes, such as pentane or hexane, halogenated $C_1$-$C_4$-alkanes, such as dichloromethane, chloroform or dichloroethane, cycloalkanes, such as cyclohexane, aromatic hydrocarbons, such as toluene and the xylenes, aliphatic ethers, such as diethyl ether, diisopropylether or methyl-tert-buty ether, cyclic ethers, such as tetrahydrofuran or the dioxanes, or carboxylic acid esters, such as ethyl acetate. The specified solvents can be used on their own or in the form of mixtures with one another. Specifically, an aromatic hydrocarbon, very specifically toluene, is used. If an acidic cationic exchanger is used, the reaction can also be carried out in the presence of a solvent that is inert under the reaction conditions. Suitable solvents are those listed above. Generally however, when a strongly acidic cation exchanger is used as Brønsted acid, the reaction is carried out neat, i.e. without the addition of an organic solvent.

The reactants can in principle be contacted with one another in any desired sequence. For example, isoprenol and hydroxypivalinaldehyde, optionally dissolved or dispersed in an inert solvent, can be initially charged and mixed with each other. To the obtained mixture the Brønsted acid can then be added. The acid can be added in one portion or gradually, either continuously or portionwise. Alternatively, isoprenol, optionally dissolved or dispersed in an inert solvent, and the Brønsted acid can be initially charged and hydroxypivalinaldehyde can be added. Alternatively, hydroxypivalinaldehyde may first be mixed with the Brønsted acid and the mixture then admixed with isoprenol. As a further alternative all reactants can be added simultaneously to the reaction vessel.

In a specific embodiment, isoprenol and hydroxypivalinaldehyde are mixed and dissolved or dispersed in an inert solvent, and the Brønsted acid is added in one portion or, preferably, gradually, either continuously or in portions.

Suitably, the water formed in the reaction is removed, generally by distillation, in order to promote the reaction.

The reaction temperature of step (a) depends on different factors, in particular on the acidity and the quantity used of the Brønsted acid, and can be determined by the person skilled in the art in the individual case, for example by simple preliminary tests. In general, the conversion in step (a) is performed at a temperature in the range of from 20 to 150° C., preferably in the range from 50 to 130° C., more preferably in the range from 100 to 120° C. To remove water, it is expedient to carry out the reaction at reflux point of the reaction mixture, which in turn depends i.a. on the solvent chosen.

The optional isolation step (b) following step (a) can for example be carried out by treating the obtained reaction mixture with an aqueous base, such as aqueous sodium hydrogen carbonate. The organic phase containing the compound (I') can then be used for step (c) or (d), either directly or after partial or complete removal of the solvent. Preferably however, the organic phase is concentrated and the crude product thus obtained is subsequently either used directly in step (c) or (d), or, preferably, subjected to further purification steps, such as distillation or chromatography, in particular distillation.

If the reaction in step (a) has been carried out neat in the presence of a cation exchange resin as Brønsted acid, work-up is generally carried out by first adding a solvent to the reaction, e.g. a polar organic solvent that is insoluble or only slightly soluble in water and suitable for dissolving the reaction product obtained, such as e.g. ethyl acetate or dichloromethane. Afterwards it is expedient to filter the diluted mixture so as to remove the cation exchange resin used as Brønsted acid. Then the above-described work-up can be carried out.

Step (a) generally yields a mixture containing at least two of the three double bond isomers (I-1), (I-2) and (I-3), most frequently all three of (I-1), (I-2) and (I-3). This mixture can be used as such in step (c) or (d). Alternatively, a separation step can be included into step (b). A simple distillation step, as mentioned above as optional purification step within the work-up step (b), is generally not suitable to separate the three double bond isomers. These may however be obtained in pure or at least enriched form in a rectification (fractional distillation) step. The degree of purity will depend on the number of theoretical plates in the fractionation column. Alternatively, high performance chromatography, such as H PLC, may be used.

Steps (a) and (b), if carried out, yield compounds (I) in which $R^5$ is hydrogen.

Under certain reaction conditions, step (a) may moreover also yield one or both acetal compounds (II.1) and (II.2). These can principally be removed in step (b), but, as said above, since they do not have any negative influence on the odor profile, a separation is not necessary. The below remarks to the further conversion of the compounds (I) in which $R^5$ is hydrogen [steps (c), (d), (e) and (f)] thus also relates to the further conversion of compounds (I) in admixture with compounds (II.1) and/or (II.2).

If a compound (I) is to be obtained in which $R^1$, $R^2$, $R^3$ and $R^4$ are hydrogen, either hydrogenation step (c) or hydrogenation step (e) is carried out.

The hydrogenation can in principle be accomplished by using any hydrogenation method known in the art to be suitable for similar conversions. Preferably, the hydrogenation is conducted by employing gaseous hydrogen as reducing agent in the presence of a catalyst typically comprising at least one transition metal, in particular one from the groups IVB, VIIIB or IB of the Periodic Table (CAS version), for example zirconium, palladium, platinum, iron, cobalt, nickel, rhodium, iridium, ruthenium or copper. These metals may be present in the catalyst in the form of one of their salts, oxides or complexes, or, alternatively in metallic form. A preferred metal in this regard is nickel, especially in the form of Raney nickel. The hydrogenation in step (c) or (e) can be carried out in analogy to the conversions described e.g. in J. H. Tyman et al., Tetrahedron Lett. 1970, 11, 4507; V. H. Rawal et al., J. Org. Chem. 1993, 58, 7718; B. M. Trost et al., J. Am. Chem. Soc. 2006, 128, 6745; L. Coulombel et al., Eur. J. Org. Chem. 2009, 33, 5788; and P. L. Alsters et al., Org. Process Res. Dev. 2010, 14, 259.

The hydrogenation in step (c) or (e) may be conducted without a solvent, but is preferably conducted in the presence of a solvent that is inert under the hydrogenation conditions, such as in particular a protic organic solvent preferably selected from $C_1$-$C_6$-alkanols, especially from methanol, ethanol and isopropanol.

The hydrogenation is typically carried at a hydrogen pressure in the range from 1 to 2 bar, preferably in the range from 1 to 1.5 bar and in particular from 1 to 1.2 bar. The temperature is usually in the range from 10 to 50° C. and preferably in the range from 20 to 40° C., e.g. from 20 to 30° C. or from 20 to 25° C.

The work-up of the reaction mixture obtained in step (c) or (e) and the isolation of the hydrogenated compound can be effected in a customary manner, for example by filtration and removal of the solvent, for example under reduced pressure. Generally, the hydrogenated product in which $R^1$, $R^2$, $R^3$ and $R^4$ are hydrogen is obtained in sufficient purity, and additional purification steps, such as chromatography or distillation are usually not necessary, but may be applied in case a very pure product is desired. For more details to purification methods, see below remarks in context with step (f).

If a compound (I) is to be obtained in which $R^5$ is not hydrogen, step (d) is carried out. The etherification (or alkylation) reaction to obtain compounds in which $R^5$ is $C_1$-$C_4$-alkyl and esterification (or acylation) reaction to obtain compounds in which $R^5$ is —C(=O)—$R^6$ can be carried out according to standard procedures in organic chemistry.

The etherification or alkylation reaction can be performed under conventional alkylation reaction conditions that are well known in the art. Preferably, the compound (I) with $R^5$ being —$C_1$-$C_4$-alkyl is prepared by alkylating compound (I')

with R⁵ being H and one of R², R³ or R⁴ together with R¹ representing a double bond (if step (c) has not been carried out) or R¹, R², R³ and R⁴ being hydrogen (if step (c) has been carried out) using the alkylation agent R⁷—Y, wherein R⁷ is a C₁-C₄-alkyl group and Y represents a leaving group, selected from halogen, such as Cl, Br, I, sulfonates, such as tosylate, mesylate, triflate or nonaflate, and sulfates, such as methylsulfate or ethylsulfate, typically in the presence of a base. Examples for alkylation agents are methyl iodide, ethyl iodide, dimethyl sulfate and diethyl sulfate.

Suitable bases are typically selected from inorganic bases and organic bases.

Suitable inorganic bases that can be used in this alkylation reaction are for example alkali metal carbonates, e.g. Li₂CO₃, Na₂CO₃, K₂CO₃ or Cs₂CO₃, alkali metal hydroxides, e.g. LiOH, NaOH or KOH, and hydride donors, e.g. NaH, LiAlH₄ or NaBH₄.

Suitable organic bases that can be used in this alkylation reaction are for example tertiary amines, e.g. trimethylamine, triethylamine, tripropylamine, ethyldiisopropylamine and the like, or basic N-heterocycles, such as morpholine, pyridine, lutidine, DMAP (4-dimethylaminopyridine), DABCO (1,4-diazabicyclo(2.2.2)octane), DBU (1,8-diazabicyclo[5.4.0]undec-7-ene) or DBN (1,5-diazabicyclo[4.3.0]non-5-ene).

Specifically, NaH is used.

Instead of using a base, the reaction can alternatively be carried out in the presence of a Lewis acid as catalyst, such as zinc chloride.

If the reaction is carried out in the presence of a base, it is expedient to first mix the compounds (I') with the base, especially if this is a hydride donor, and adding only subsequently the alkylation agent.

The work-up of the reaction mixture obtained in the alkylation reaction and the purification/isolation of the product of formula (I) with R⁵ being —C₁-C₄-alkyl [optional step (f)] are effected in a customary manner, for example by quenching the reaction mixture to hydrolyse any remaining alkylation agent, followed by extractive work-up with an organic solvent that is insoluble or only slightly soluble in water and suitable for dissolving the reaction product obtained, such as e.g. an open-chained ether, e.g. diethyl ether or methyl-tert-butyl ether, dichloromethane or ethyl acetate; and removal of the organic solvent, e.g. under reduced pressure. The desired product is generally obtained in sufficient purity by applying such measures or a combination thereof. However, additional purification steps, such as chromatography, distillation or rectification may be performed if a very pure compound of formula (I) with R⁵ being —C₁-C₄-alkyl is desired.

Generally, the ester of formula (I) with R⁵ being —C(=O)—R⁶ can efficiently be prepared by reacting the compound (I'), where R⁵ is H and one of R², R³ or R⁴ together with R¹ represents a double bond (if step (c) has not been carried out) or R¹, R², R³ and R⁴ are hydrogen (if step (c) has been carried out), with the carboxylic acid R⁶—COOH, wherein R⁶ has one of the meanings defined herein, or an acid anhydride thereof, such as acetic anhydride or propionic anhydride. The reaction is typically performed in the presence of an esterification catalyst or a base.

Suitable esterification catalysts that can be applied in this reaction are well known in the art and are for example metal based catalysts, e.g. iron, cadmium, cobalt, lead, zinc, antimony, magnesium, titanium and tin catalysts in the form of metals, metal oxides or metal salts, such as metal alcoxylates, mineral acids, such as sulfuric acid, hydrochloric acid or phosphoric acid, or organic sulfonic acids, such as methanesulfonic acid or para-toluenesulfonic acid.

Suitable bases are for example organic bases, as defined above, such as in particular pyridine, lutidine or DMAP, specifically DMAP.

Alternatively, the ester of formula (I) with R⁵ being —(C=O)—R⁶ can be prepared by reacting the compound (I'), where R⁵ is H, with an acid halide of the formula R⁶—(C=O)Y', wherein R⁶ has one of the meanings defined herein and Y' is halogen, such as Cl, Br or I, in the presence of an organic base, preferably one of those defined above.

Preferably, the ester of formula (I) with R⁵ being —(C=O)—R⁶ is prepared by reacting the compound (I'), where R⁵ is H, with an acid anhydride of the carboxylic acid R⁶—COOH in the presence of an organic base.

The individual reaction conditions for the preparations of the ester of formula (I) with R⁵ being —(C=O)—R⁶, as outlined above, are well known in the art.

The work-up of the reaction mixtures obtained in the acylation reaction and the isolation/purification of the product of formula (I) with R⁵ being —(C=O)—R⁶ [optional step (f)] are effected in a customary manner, for example by quenching the reaction mixture to hydrolyse any remaining acid anhydride or acid halide, followed by extractive work-up with an organic solvent that is insoluble or only slightly soluble in water and suitable for dissolving the reaction product obtained, such as e.g. an open-chained ether, e.g. diethyl ether or methyl-tert-butyl ether, dichloromethane or ethyl acetate; and removal of the organic solvent, e.g. under reduced pressure. The desired product is generally obtained in sufficient purity by applying such measures or a combination thereof. However, additional purification steps, such as chromatography, distillation or rectification may be performed if a very pure compound of formula (I) with R⁵ being —(C=O)—R⁶ is desired. Alternatively, compounds (I) can be prepared by subjecting hydroxypivalinaldehyde 2 to an esterification or etherification reaction and then reacting the obtained ester/ether with 3-methylbut-3-en-1-ol (isoprenol) 1, as shown in scheme 2 below (method B). The reaction of the ester/ether of 2 (compound 3 in scheme 2) with 1 is generally carried out in the presence of a BF₃ source. The reaction leads to compounds (I) wherein R⁵ is different from H [named in the following compounds (I"); R⁵ which is different from H is termed below R⁵ᵃ].

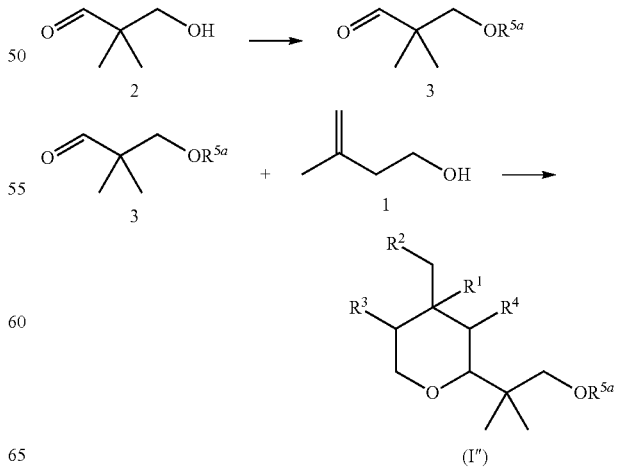

Scheme 2

In the reaction product (I″) of scheme 2, one of $R^2$, $R^3$ or $R^4$ together with $R^1$ represents a double bond and the others of $R^2$, $R^3$ or $R^4$ are hydrogen, and $R^{5a}$ is $C_1$-$C_4$-alkyl or —C(=O)—$R^6$, where $R^6$ is as defined above.

Another aspect of the invention relates thus to a method for preparing a compound of the formula (I) wherein $R^5$ is selected from the group consisting of $C_1$-$C_4$-alkyl and —C(=O)—$R^6$, a stereoisomer thereof, a mixture of stereoisomers thereof, a mixture of different compounds (I), as defined above, which method comprises:

(i) subjecting 3-hydroxy-2,2-dimethyl-propanal (hydroxypivalinaldehyde) to an etherification or esterification reaction to obtain a reaction mixture containing a compound of the formula 3

3 wherein $R^{5a}$ is selected from the group consisting of $C_1$-$C_4$-alkyl and —C(=O)—$R^6$;

(ii) optionally isolating the compound of the formula 3 from the reaction mixture obtained in step (i) or enriching it in the reaction mixture obtained in step (i);

(iii) reacting the reaction mixture obtained in step (i) or the product obtained in step (ii) with 3-methylbut-3-en-1-ol (isoprenol) in the presence of a $BF_3$ source to obtain a reaction mixture containing a compound of the formula (I) wherein one of $R^2$, $R^3$ or $R^4$ together with $R^1$ represents a double bond and the others of $R^2$, $R^3$ or $R^4$ are hydrogen and $R^5$ is selected from the group consisting of $C_1$-$C_4$-alkyl and —C(=O)—$R^6$;

(iv) if a compound of the formula (I), wherein $R^1$, $R^2$, $R^3$ and $R^4$ are hydrogen and $R^5$ is selected from the group consisting of $C_1$-$C_4$-alkyl and —C(=O)—$R^6$, is to be prepared: subjecting the product obtained in step (iii) to a hydrogenation reaction; and (v) optionally subjecting the product obtained in step (iii) or step (iv) to a purification step.

The etherification or esterification step (i) can be carried out according to standard procedures in organic chemistry and as depicted above for step (d).

The etherification or alkylation reaction of step (i) can be performed under conventional alkylation reaction conditions that are well known in the art. Preferably, the compound 3 with $R^{5a}$ being —$C_1$-$C_4$-alkyl is prepared by alkylating compound 2 using the alkylation agent $R^7$—Y, wherein $R^7$ is a $C_1$-$C_4$-alkyl group and Y represents a leaving group, selected from halogen, such as Cl, Br, I, sulfonates, such as tosylate, mesylate, triflate or nonaflate, and sulfates, such as methylsulfate or ethylsulfate, typically in the presence of a base. Examples for alkylation agents are methyl iodide, ethyl iodide, dimethyl sulfate, diethyl sulfate, dimethyl carbonate and diethyl carbonate.

Suitable bases are typically selected from inorganic bases and organic bases.

Suitable inorganic bases that can be used in this alkylation reaction are for example alkali metal carbonates, e.g. $Li_2CO_3$, $Na_2CO_3$, $K_2CO_3$ or $Cs_2CO_3$, alkali metal hydroxides, e.g. LiOH, NaOH or KOH, and hydride donors, e.g. NaH, $LiAlH_4$ or $NaBH_4$.

Suitable organic bases that can be used in this alkylation reaction are for example tertiary amines, e.g. trimethylamine, triethylamine, tripropylamine, ethyldiisopropylamine and the like, or basic N-heterocycles, such as morpholine, pyridine, lutidine, DMAP (4-dimethylaminopyridine), DABCO (1,4-diazabicyclo(2.2.2)octane), DBU (1,8-diazabicyclo[5.4.0]undec-7-ene) or DBN (1,5-diazabicyclo[4.3.0]non-5-ene).

Instead of using a base, the reaction can alternatively be carried out in the presence of a Brønsted acid or a Lewis acid as catalyst. Suitable Brønsted acids are those listed above in context with step (a) of method A. A suitable Lewis acid is for example zinc chloride.

If the reaction is carried out in the presence of a base, it is expedient to first mix the compounds 2 with the base, especially if this is a hydride donor, and adding only subsequently the alkylation agent.

The work-up of the reaction mixture obtained in the alkylation reaction and the purification/isolation of the product 3 with $R^{5a}$ being —$C_1$-$C_4$-alkyl [optional step (b)] are effected in a customary manner, for example by quenching the reaction mixture to hydrolyse any remaining alkylation agent, followed by extractive work-up with an organic solvent that is insoluble or only slightly soluble in water and suitable for dissolving the reaction product obtained, such as e.g. an open-chained ether, e.g. diethyl ether or methyl-tert-butyl ether, dichloromethane or ethyl acetate; and removal of the organic solvent, e.g. under reduced pressure. The desired product is generally obtained in sufficient purity by applying such measures or a combination thereof. However, additional purification steps, such as chromatography, distillation or rectification may be performed if a very pure compound of formula 3 with $R^{5a}$ being —$C_1$-$C_4$-alkyl is desired.

Generally, the ester of formula 3 with $R^{5a}$ being —C(=O)—$R^6$ can efficiently be prepared by reacting the compound 2 with the carboxylic acid $R^6$—COOH, wherein $R^6$ has one of the meanings defined herein, or an acid anhydride thereof, such as acetic anhydride or propionic anhydride. The reaction is typically performed in the presence of an esterification catalyst or a base.

Suitable esterification catalysts that can be applied in this reaction are well known in the art and are for example acids, such as mineral acids, for example sulfuric acid, hydrochloric acid or phosphoric acid; or organic sulfonic acids, such as methanesulfonic acid, para-toluenesulfonic acid or camphorsulfonic acid; or metal based catalysts, e.g. iron, cadmium, cobalt, lead, zinc, antimony, magnesium, titanium and tin catalysts in the form of metals, metal oxides or metal salts, such as metal alcoxylates.

Suitable bases are for example organic bases, as defined above, such as in particular pyridine, lutidine or DMAP, specifically DMAP.

Alternatively, the ester of formula 3 with $R^{5a}$ being —(C=O)—$R^6$ can be prepared by reacting the compound 2 with an acid halide of the formula $R^6$—(C=O)Y', wherein $R^6$ has one of the meanings defined herein and Y' is halogen, such as Cl, Br or I, in the presence of an organic base, preferably one of those defined above.

Preferably, the ester of formula 3 with $R^{5a}$ being —(C=O)—$R^6$ is prepared by reacting the compound 2 with the carboxylic acid $R^6$—COOH in the presence of an acid, in particular of an organic sulfonic acid. Specifically, toluenesulfonic acid is used.

The acid is generally used in catalytic amounts, for example in an amount of from 0.01 to 20 mol-%, preferably from 0.05 to 15 mol-%, in particular from 0.1 to 10 mol-%, specifically from 1 to 5 mol-%, relative to 1 mol of 2.

The individual reaction conditions for the preparations of the ester of formula 3 with $R^{5a}$ being —(C=O)—$R^6$, as outlined above, are well known in the art.

In the preferred embodiment of reacting the compound 2 with the carboxylic acid $R^6$—COOH in the presence of an acid, suitably, the water formed in the reaction is removed, generally by distillation, in order to promote the reaction.

The work-up of the reaction mixtures obtained in the acylation reaction and the isolation/purification of the product of formula 3 with $R^{5a}$ being —C(=O)—$R^6$ [optional step (b)] are effected in a customary manner, for example by chromatography, distillation or rectification, especially if a very pure compound 3 is desired.

The reaction of 1 and 3 in step (iii) is suitably carried out using a $BF_3$ source as a catalyst. Suitable $BF_3$ sources are gaseous $BF_3$ and $BF_3$ complexes with dialkyl ethers (e.g. diethyl ether), dicycloalkyl ethers (e.g. dicyclohexyl ether), tetrahydrofuran, phenol, aryl alkyl ethers (e.g. anisole) or aliphatic alcohols. For practical reasons, preference is given to the use of $BF_3$ complexes. Among these, preference is given to $BF_3$ complexes with dialkyl ethers, and in particular with diethyl ether ($BF_3$-diethyl etherate).

The $BF_3$ source is preferably used in substoichiometric amounts, for example in an amount of from 1 to 50 mol-%, preferably from 10 to 30 mol-% and in particular from 15 to 25 mol-%, relative to 1 mol of that starting compound 1 or 3 which is used in a smaller amount. If 1 and 3 are used in equimolar amounts, the percentage is of course relative to 1 mol of either of the starting compounds. 1 and 3 are usually applied in a molar ratio of 0.7:1 to 1.5:1 and preferably in a molar ratio of 0.9:1 to 1.3:1. For economic reasons, it is expedient to use 1 in at least equimolar amounts, so that the molar ratio of 1 and 3 is for example 1:1 to 1.3:1, and it is even more expedient to use 1 in slight excess, so that the molar ratio of 1 and 3 is for example 1.1:1 to 1.3:1.

The reactants can in principle be contacted with one another in any desired sequence. For example, 1 and 3, optionally dissolved or dispersed in an inert solvent, can be initially charged and mixed with each other. To the obtained mixture the $BF_3$ source can then be added. The $BF_3$ source can be added in one portion or gradually, either continuously or portionwise. Alternatively, 1, optionally dissolved or dispersed in an inert solvent, and the $BF_3$ source can be initially charged and 3 can be added. Alternatively, 3 may first be mixed with the $BF_3$ source and the mixture then admixed with 1. As a further alternative all reactants can be added simultaneously to the reaction vessel.

In a specific embodiment, 1 and 3 are mixed and dissolved or dispersed in an inert solvent, and the $BF_3$ source added in one portion.

The reaction temperature of step (iii) depends on different factors, for example on the type of $BF_3$ source used (the reaction with gaseous $BF_3$ generally being carried out at lower temperatures than with $BF_3$ complexes), and can be determined by the person skilled in the art in the individual case, for example by simple preliminary tests. In general, the conversion in step (iii) is performed at a temperature in the range of from 20 to 150° C., preferably in the range from 50 to 130° C., more preferably in the range from 60 to 100° C.

After completion of step (iii), the compound (I") is isolated by usual work-up, for example by treating the obtained reaction mixture with an aqueous base, such as aqueous sodium hydrogen carbonate. The organic phase containing the compound (I") can then be separated from the aqueous phase and concentrated to yield the compound (I").

To obtain compounds (I) wherein $R^1$, $R^2$, $R^3$ and $R^4$ are hydrogen, the product of step (iii) is subjected to a hydrogenation reaction [step (iv)]. Suitable hydrogenation conditions correspond to those described above for steps (c) and (e) of method A.

In the optional step (v) following step (iii) or (iv) the crude product obtained in step (iii) or (iv) may be subjected to further purification steps, such as distillation or chromatography, in particular distillation.

Step (iii) generally yields a mixture containing at least two of the three double bond isomers (I-1), (I-2) and (I-3), most frequently all three of (I-1), (I-2) and (I-3), wherein $R^5$ is $C_1$-$C_4$-alkyl or —C(=O)—$R^6$. If desired, a separation step can be included into step (v).

A simple distillation step, as mentioned above, is generally not suitable to separate the three double bond isomers. These may however be obtained in pure or at least enriched form in a rectification (fractional distillation) step. The degree of purity will depend on the number of theoretical plates in the fractionation column. Alternatively, high performance chromatography, such as HPLC, may be used.

Method B yield compounds (I) in which $R^5$ is $C_1$-$C_4$-alkyl or —C(=O)—$R^6$.

Method B generally avoids the formation of acetal compounds (II.1) and (II.2).

Another aspect of the invention is the product obtained with the methods of the invention (method A or method B).

Use and Methods of Use of the Compounds (I)

As already explained, the compounds of formula (I) or a stereoisomer thereof or a mixture of two or more stereoisomers thereof or a mixture of two or more different compounds (I) or a mixture of at least one compound of the formula (I) with one or both of the compounds of the formula (II.1) and/or (II.2), as defined above, are useful as aroma chemicals.

Accordingly, a further aspect of the present invention is the use of a compound of formula (I) or of a stereoisomer thereof or of a mixture of two or more stereoisomers thereof or of a mixture of two or more different compounds (I) or of a mixture of at least one compound of the formula (I) with one or both of the compounds of the formula (II.1) and/or (II.2), as defined above, as an aroma chemical.

Preferably, the compounds of formula (I) or their stereoisomers or a mixture of two or more stereoisomers thereof or a mixture of two or more different compounds (I) or a mixture of at least one compound of the formula (I) with one or both of the compounds of the formula (II.1) and/or (II.2), as defined above, are used for imparting an olfactory impression. In particular, the compounds of formula (I) or their stereoisomers or a mixture of two or more stereoisomers thereof or a mixture of two or more different compounds (I) or a mixture of at least one compound of the formula (I) with one or both of the compounds of the formula (II.1) and/or (II.2), as defined above, are used as a fragrance.

In particular, a mixture of the above-described compounds (I-1), (I-2) and (I-3), wherein in each case $R^5$ is H, is used to impart a pineapple, green, chrysanthemum note; or is used to produce a scent with a pineapple, green, chrysanthemum note. Specifically, compounds (I-1), (I-2) and (I-3), wherein in each case $R^5$ is H, are present in a weight ratio of ca. 40:25:35.

In particular, a mixture of the above-described compounds (I-1), (I-2) and (I-3), wherein in each case $R^5$ is —C(=O)$CH_3$, is used to impart a floral, apricot, green, bux tree note; or is used to produce a scent with a floral, apricot, green, bux tree note. Specifically, compounds (I-1), (I-2) and (I-3), wherein in each case $R^5$ is —C(=O)$CH_3$, are present in a weight ratio of ca. 70:15:15.

In particular, a mixture of the above-described compounds (I-1), (I-2) and (I-3), wherein in each case $R^5$ is —C(=O)$CH_3$, is used to impart a sweet, woody, green, herbal note; or is used to produce a scent with a sweet, woody, green, herbal note. Specifically, compounds (I-1), (I-2) and (I-3), wherein in each case $R^5$ is —C(=O)CH$_3$, are present in a weight ratio of ca. 44:18:33 or of ca. 2:66:30.

In particular, a mixture of the above-described compounds (I-1), (I-3), (II.1) and (II.2), wherein in each case $R^5$ is —C(=O)CH$_2$CH$_3$, is used to impart a white floral, freesia, grape note; or is used to produce a scent with a white floral, freesia, grape note. Specifically, compounds (I-1), (I-3), (II.1) and (II.2), wherein in each case $R^5$ is —C(=O)CH$_2$CH$_3$, are present in a weight ratio of ca. 50:20:20:5.

In particular, a mixture of the above-described compounds (I-1), (I-2) and (I-3), wherein in each case $R^5$ is —C(=O)CH$_2$CH$_3$, is used to impart a woody, ambery, pepper, natural, warm, spicy note; or is used to produce a scent with a woody, ambery, pepper, natural, warm, spicy note. Specifically, compounds (I-1), (I-2) and (I-3), wherein in each case $R^5$ is —C(=O)CH$_2$CH$_3$, are present in a weight ratio of ca. 52:23:19.

In particular, a mixture of the above-described compounds (I-1), (I-2) and (I-3), wherein in each case $R^5$ is —C(=O)CH$_2$CH$_3$, is used to impart a cedarwood, smoky, dusty note; or is used to produce a scent with a cedarwood, smoky, dusty note. Specifically, compounds (I-1), (I-2) and (I-3), wherein in each case $R^5$ is —C(=O)CH$_2$CH$_3$, are present in a weight ratio of ca. 2:62:35.

In particular, a mixture of the above-described compounds (I-1), (I-2) and (I-3), wherein in each case $R^5$ is —CH$_3$, is used to impart a floral, pencil shavings, carrot, lime, bergamot note; or is used to produce a scent with a floral, pencil shavings, carrot, lime, bergamot note. Specifically, compounds (I-1), (I-2) and (I-3), wherein in each case $R^5$ is —C(=O)CH$_3$, are present in a weight ratio of ca. 35:45:20.

In particular, a mixture of the above-described compounds (I-1), (I-2) and (I-3), wherein in each case $R^5$ is —CH$_2$CH$_3$, is used to impart a an etheral, herbal, soapy, mimosa, cedarwood, floral note; or is used to produce a scent with an etheral, herbal, soapy, mimosa, cedarwood, floral note. Specifically, compounds (I-1), (I-2) and (I-3), wherein in each case $R^5$ is —CH$_2$CH$_3$, are present in a weight ratio of ca. 50:30:20.

The compounds (I), the mixtures thereof, the stereoisomers thereof, the stereoisomer mixtures thereof or the mixtures of at least one compound of the formula (I) with one or both of the compounds of the formula (II.1) and/or (II.2) are generally used in a ready-to-use composition, in particular in a fragranced ready-to-use composition. "Fragranced ready-to-use composition", as used herein, refers to a ready-to-use composition which predominately induces a pleasant odor impression.

Fragranced ready-to-use compositions are for example compositions used in personal care, in home care, in industrial applications as well as compositions used in other applications, such as pharmaceutical compositions or crop protection compositions.

Preferably, the compounds of formula (I) or the stereoisomers thereof or the mixtures of two or more stereoisomers thereof or the mixtures of two or more different compounds (I) or the mixtures of at least one compound of the formula (I) with one or both of the compounds of the formula (II.1) and/or (II.2) are used in a composition selected from the group consisting of perfume compositions, body care compositions (including cosmetic compositions), products for oral and dental hygiene, hygiene articles, cleaning compositions (including dishwashing compositions), textile detergent compositions, compositions for scent dispensers, foods, food supplements, pharmaceutical compositions and crop protection compositions.

In particular, a mixture of the above-described compounds (I-1), (I-2) and (I-3), wherein in each case $R^5$ is H, is used to impart a pineapple, green, chrysanthemum note to the above-listed compositions. Specifically, compounds (I-1), (I-2) and (I-3), wherein in each case $R^5$ is H, are present in a weight ratio of ca. 40:25:35.

In particular, a mixture of the above-described compounds (I-1), (I-2) and (I-3), wherein in each case $R^5$ is —C(=O)CH$_3$, is used to impart a floral, apricot, green, bux tree note to the above-listed compositions. Specifically, compounds (I-1), (I-2) and (I-3), wherein in each case $R^5$ is —C(=O)CH$_3$, are present in a weight ratio of ca. 70:15:15.

In particular, a mixture of the above-described compounds (I-1), (I-2) and (I-3), wherein in each case $R^5$ is —C(=O)CH$_3$, is used to impart a sweet, woody, green, herbal note to the above-listed compositions. Specifically, compounds (I-1), (I-2) and (I-3), wherein in each case $R^5$ is —C(=O)CH$_3$, are present in a weight ratio of ca. 44:18:33 or of ca. 2:66:30.

In particular, a mixture of the above-described compounds (I-1), (I-3), (II.1) and (II.2), wherein in each case $R^5$ is —C(=O)CH$_2$CH$_3$, is used to impart a white floral, freesia, grape note to the above-listed compositions. Specifically, compounds (I-1), (I-3), (II.1) and (II.2), wherein in each case $R^5$ is —C(=O)CH$_2$CH$_3$, are present in a weight ratio of ca. 50:20:20:5.

In particular, a mixture of the above-described compounds (I-1), (I-2) and (I-3), wherein in each case $R^5$ is —C(=O)CH$_2$CH$_3$, is used to impart a woody, ambery, pepper, natural, warm, spicy note to the above-listed compositions. Specifically, compounds (I-1), (I-2) and (I-3), wherein in each case $R^5$ is —C(=O)CH$_2$CH$_3$, are present in a weight ratio of ca. 52:23:19.

In particular, a mixture of the above-described compounds (I-1), (I-2) and (I-3), wherein in each case $R^5$ is —C(=O)CH$_2$CH$_3$, is used to impart a cedarwood, smoky, dusty note to the above-listed compositions. Specifically, compounds (I-1), (I-2) and (I-3), wherein in each case $R^5$ is —C(=O)CH$_2$CH$_3$, are present in a weight ratio of ca. 2:62:35.

In particular, a mixture of the above-described compounds (I-1), (I-2) and (I-3), wherein in each case $R^5$ is —CH$_3$, is used to impart a floral, pencil shavings, carrot, lime, bergamot note to the above-listed compositions. Specifically, compounds (I-1), (I-2) and (I-3), wherein in each case $R^5$ is —CH$_3$, are present in a weight ratio of ca. 35:45:20.

In particular, a mixture of the above-described compounds (I-1), (I-2) and (I-3), wherein in each case $R^5$ is —CH$_2$CH$_3$, is used to impart a an etheral, herbal, soapy, mimosa, cedarwood, floral note to the above-listed compositions. Specifically, compounds (I-1), (I-2) and (I-3), wherein in each case $R^5$ is —CH$_2$CH$_3$, are present in a weight ratio of ca. 50:30:20.

Details to the above-listed compositions are given below.

In addition to the olfactory properties, the compounds (I), the mixtures thereof, the stereoisomers thereof, the stereoisomer mixtures thereof or the mixtures of at least one compound of the formula (I) with one or both of the compounds of the formula (II.1) and/or (II.2) exhibit advantageous secondary properties.

For example, they can provide better sensory profiles as a result of synergistic effects with other fragrances, which means that they can provide a booster effect for other fragrances. They are therefore suitable as boosters for other fragrances.

Accordingly, another aspect of the invention relates to the use of the compounds (I), the mixtures thereof, the stereoisomers thereof, the stereoisomer mixtures thereof or the mixtures of at least one compound of the formula (I) with one or both of the compounds of the formula (II.1) and/or (II.2) for modifying the scent character of a fragranced composition; and specifically to the use as a booster for other fragrances.

Booster effect means that the substances enhance and intensify in perfumery formulations the overall impression of the mixture. In the mint range, for example, it is known that menthyl methyl ether intensifies the perfumery or taste mixtures of peppermint oils and particularly in top notes brings about a considerably more intensive and more complex perception although the ether itself, being a pure substance, develops no particular intensive odor at all. In fragrance applications, Hedione® (methyl dihydrojasmonate), which as a pure substance only exhibits a light floral jasmin-note, reinforces diffusion, freshness and volume of a perfume composition as an odor booster.

Booster effects are particularly desired when top-note-characterized applications are required, in which the odor impression is to be conveyed particularly quickly and intensively, for example in deodorants, air fresheners or in the taste sector in chewing gums.

To achieve such a booster effect, the compounds (I), the mixtures thereof, the stereoisomers thereof or the stereoisomer mixtures thereof are generally used in an amount of 0.1-20% by weight, preferably in an amount of 0.5 to 5% by weight, in particular in an amount of from 0.6 to 3% by weight, based on the total weight of the fragrance mixture.

Furthermore, the compounds (I), the mixtures thereof, the stereoisomers thereof or the stereoisomer mixtures thereof can have further positive effects on the composition in which they are used. For example, they can enhance the overall performance of the composition into which they are incorporated, such as the stability, e.g. the formulation stability, the extendability or the staying power of the composition.

A further embodiment of the invention is directed to a method of preparing an aroma chemical composition, in particular a fragranced composition, especially a fragranced ready-to-use composition, comprising incorporating at least one compound of formula (I), a stereoisomer thereof or a mixture of stereoisomers thereof into the target composition, e.g. a ready-to-use composition, resulting in an aroma chemical composition, in particular in a fragranced composition, especially in a fragranced ready-to-use composition. Alternatively, the invention is directed to a method of preparing an aroma chemical composition, in particular a fragranced composition, especially a fragranced ready-to-use composition, comprising mixing at least one compound of formula (I), a stereoisomer thereof or a mixture of stereoisomers thereof with at least one aroma chemical different from compounds (I) and/or with at least one non-aroma chemical carrier and/or with at least one antioxidant and/or with at least one deodorant-active agent. Suitable and preferred aroma chemicals different from compounds (I), non-aroma chemical carriers, antioxidants and deodorant-active agents are described below.

For example, the method can be carried out by mixing at least one compound of formula (I), a stereoisomer thereof or a mixture of stereoisomers thereof, as defined above, and at least one further component selected from the group consisting of aroma chemicals different from compounds (I), non-aroma chemical carriers, antioxidants and deodorant-active agents.

The invention is also directed to a method for modifying the scent character of an aroma chemical composition, in particular of a fragranced composition, especially of a fragranced ready-to-use composition, comprising incorporating at least one compound of formula (I), a stereoisomer thereof, a mixture of stereoisomers thereof or a mixture of at least one compound of the formula (I) with one or both of the compounds of the formula (II.1) and/or (II.2) into an aroma chemical composition, in particular into a fragranced composition, especially into a fragranced ready-to-use composition.

In particular, the invention is directed to a method of preparing a perfume composition, body care composition, product for oral and dental hygiene, hygiene article, cleaning composition, textile detergent composition, composition for scent dispensers, food, food supplement, pharmaceutical composition or crop protection composition, comprising including the compounds of formula (I), the mixtures thereof, the stereoisomers thereof, the mixture of stereoisomers thereof or the mixtures of at least one compound of the formula (I) with one or both of the compounds of the formula (II.1) and/or (II.2) as defined above in a perfume composition, body care composition, product for oral and dental hygiene, hygiene article, cleaning composition, textile detergent composition, composition for scent dispensers, food, food supplement, pharmaceutical composition or crop protection composition.

In a particular embodiment the invention is directed to a method for imparting a pineapple, green, chrysanthemum note to a perfume composition, body care composition, product for oral and dental hygiene, hygiene article, cleaning composition, textile detergent composition, composition for scent dispensers, food, food supplement, pharmaceutical composition or crop protection composition, which comprises including a mixture of the above-described compounds (I-1), (I-2) and (I-3), wherein in each case $R^5$ is H, or a mixture of stereoisomers thereof in a perfume composition, body care composition, product for oral and dental hygiene, hygiene article, cleaning composition, textile detergent composition, composition for scent dispensers, food, food supplement, pharmaceutical composition or crop protection composition. Specifically, compounds (I-1), (I-2) and (I-3), wherein in each case $R^5$ is H, are present in a weight ratio of ca. 40:25:35.

In a particular embodiment the invention is directed to a method for imparting a floral, apricot, green, bux tree note to a perfume composition, body care composition, product for oral and dental hygiene, hygiene article, cleaning composition, textile detergent composition, composition for scent dispensers, food, food supplement, pharmaceutical composition or crop protection composition, which comprises including a mixture of the above-described compounds (I-1), (I-2) and (I-3), wherein in each case $R^5$ is —C(=O)CH$_3$, or a mixture of stereoisomers thereof in a perfume composition, body care composition, product for oral and dental hygiene, hygiene article, cleaning composition, textile detergent composition, composition for scent dispensers, food, food supplement, pharmaceutical composition or crop protection composition. Specifically, compounds (I-1), (I-2) and (I-3), wherein in each case $R^5$ is —C(=O)CH$_3$, are present in a weight ratio of ca. 70:15:15.

In a particular embodiment the invention is directed to a method for imparting a sweet, woody, green, herbal note to a perfume composition, body care composition, product for oral and dental hygiene, hygiene article, cleaning composition, textile detergent composition, composition for scent dispensers, food, food supplement, pharmaceutical composition or crop protection composition, which comprises including a mixture of the above-described compounds (I-1), (I-2) and (I-3), wherein in each case $R^5$ is —C(═O)CH$_3$, or a mixture of stereoisomers thereof in a perfume composition, body care composition, product for oral and dental hygiene, hygiene article, cleaning composition, textile detergent composition, composition for scent dispensers, food, food supplement, pharmaceutical composition or crop protection composition. Specifically, compounds (I-1), (I-2) and (I-3), wherein in each case $R^5$ is —C(═O)CH$_3$, are present in a weight ratio of ca. 44:18:33 or 2:66:30.

In another particular embodiment the invention is directed to a method for imparting a white floral, freesia, grape note to a perfume composition, body care composition, product for oral and dental hygiene, hygiene article, cleaning composition, textile detergent composition, composition for scent dispensers, food, food supplement, pharmaceutical composition or crop protection composition, which comprises including a mixture of the above-described compounds (I-1), (I-3), (II.1) and (II.2), wherein in each case $R^5$ is —C(═O)CH$_2$CH$_3$, or a mixture of stereoisomers thereof in a perfume composition, body care composition, product for oral and dental hygiene, hygiene article, cleaning composition, textile detergent composition, composition for scent dispensers, food, food supplement, pharmaceutical composition or crop protection composition. Specifically, compounds (I-1), (I-3), (II.1) and (II.2), wherein in each case $R^5$ is —C(═O)CH$_2$CH$_3$, are present in a weight ratio of ca. 50:20:20:5.

In another particular embodiment the invention is directed to a method for imparting a woody, ambery, pepper, natural, warm, spicy note to a perfume composition, body care composition, product for oral and dental hygiene, hygiene article, cleaning composition, textile detergent composition, composition for scent dispensers, food, food supplement, pharmaceutical composition or crop protection composition, which comprises including a mixture of the above-described compounds (I-1), (I-2) and (I-3), wherein in each case $R^5$ is —C(═O)CH$_2$CH$_3$, or a mixture of stereoisomers thereof in a perfume composition, body care composition, product for oral and dental hygiene, hygiene article, cleaning composition, textile detergent composition, composition for scent dispensers, food, food supplement, pharmaceutical composition or crop protection composition. Specifically, compounds (I-1), (I-2) and (I-3), wherein in each case $R^5$ is —C(═O)CH$_2$CH$_3$, are present in a weight ratio of ca. 52:23:19.

In another particular embodiment the invention is directed to a method for imparting a cedarwood, smoky, dusty note to a perfume composition, body care composition, product for oral and dental hygiene, hygiene article, cleaning composition, textile detergent composition, composition for scent dispensers, food, food supplement, pharmaceutical composition or crop protection composition, which comprises including a mixture of the above-described compounds (I-1), (I-2) and (I-3), wherein in each case $R^5$ is —C(═O)CH$_2$CH$_3$, or a mixture of stereoisomers thereof in a perfume composition, body care composition, product for oral and dental hygiene, hygiene article, cleaning composition, textile detergent composition, composition for scent dispensers, food, food supplement, pharmaceutical composition or crop protection composition. Specifically, compounds (I-1), (I-2) and (I-3), wherein in each case $R^5$ is —C(═O)CH$_2$CH$_3$, are present in a weight ratio of ca. 2:62:35.

In another particular embodiment the invention is directed to a method for imparting a floral, pencil shavings, carrot, lime, bergamot note to a perfume composition, body care composition, product for oral and dental hygiene, hygiene article, cleaning composition, textile detergent composition, composition for scent dispensers, food, food supplement, pharmaceutical composition or crop protection composition, which comprises including a mixture of the above-described compounds (I-1), (I-2) and (I-3), wherein in each case $R^5$ is —CH$_3$, or a mixture of stereoisomers thereof in a perfume composition, body care composition, product for oral and dental hygiene, hygiene article, cleaning composition, textile detergent composition, composition for scent dispensers, food, food supplement, pharmaceutical composition or crop protection composition. Specifically, compounds (I-1), (I-2) and (I-3), wherein in each case $R^5$ is —CH$_3$, are present in a weight ratio of ca. 35:45:20.

In another particular embodiment the invention is directed to a method for imparting a etheral, herbal, soapy, mimosa, cedarwood, floral note to a perfume composition, body care composition, product for oral and dental hygiene, hygiene article, cleaning composition, textile detergent composition, composition for scent dispensers, food, food supplement, pharmaceutical composition or crop protection composition, which comprises including a mixture of the above-described compounds (I-1), (I-2) and (I-3), wherein in each case $R^5$ is —CH$_3$, or a mixture of stereoisomers thereof in a perfume composition, body care composition, product for oral and dental hygiene, hygiene article, cleaning composition, textile detergent composition, composition for scent dispensers, food, food supplement, pharmaceutical composition or crop protection composition. Specifically, compounds (I-1), (I-2) and (I-3), wherein in each case $R^5$ is —CH$_3$, are present in a weight ratio of ca. 50:30:20.

Compositions

The invention relates moreover to a composition comprising a compound of formula (I), a mixture thereof [i.e. a mixture of different compounds (I)], a stereoisomer thereof, a mixture of stereoisomers thereof or a mixture of at least one compound of the formula (I) with one or both of the compounds of the formula (II.1) and/or (II.2) as defined above and at least one further component selected from the group consisting of aroma chemicals different from compounds (I), (II.1) and (II.2), non-aroma chemical carriers, anti-oxidants and deodorant-active agents.

The (further) aroma chemical is of course different from the compounds of formula (I), (II.1) and (II.2) or their stereoisomers or mixtures of their stereoisomers.

The non-aroma chemical carrier is in particular selected from the group consisting of surfactants, oil components (emollients) and solvents.

Thus, in a preferred embodiment, the composition comprises a compound of formula (I), a mixture thereof [i.e. a mixture of different compounds (I)], a stereoisomer thereof, a mixture of stereoisomers thereof or a mixture of at least one compound of the formula (I) with one or both of the compounds of the formula (II.1) and/or (II.2) as defined above and at least one further component selected from the group consisting of aroma chemicals different from compounds (I), (II.1) and (II.2), surfactants, oil components, solvents, anti-oxidants and deodorant-active agents. The pleasant aroma, low volatility and excellent solubility make compounds (I) suitable components in compositions where a pleasing aroma is desirable.

Accordingly, said composition is preferably an aroma chemical composition, more preferably an odor composition and in particular a fragrance composition.

One embodiment of the invention is directed to a composition comprising a compound of formula (I), a mixture thereof [i.e. a mixture of different compounds (I)], a stereoisomer thereof, a mixture of stereoisomers thereof or a mixture of at least one compound of the formula (I) with one or both of the compounds of the formula (II.1) and/or (II.2) as defined above and at least one further component selected from the group consisting of oil components, solvents, anti-oxidants and deodorant-active agents.

One embodiment of the invention is directed to a composition comprising a compound of formula (I), a stereoisomer thereof, a mixture of stereoisomers thereof, a mixture of different compounds (I) or a mixture of at least one compound of the formula (I) with one or both of the compounds of the formula (II.1) and/or (II.2), and at least one aroma chemical.

One embodiment of the invention is directed to a composition comprising a compound of formula (I), a stereoisomer thereof, a mixture of stereoisomers thereof, a mixture of different compounds (I) or a mixture of at least one compound of the formula (I) with one or both of the compounds of the formula (II.1) and/or (II.2), and at least one non-aroma chemical carrier.

One embodiment of the invention is directed to a composition comprising a compound of formula (I), a stereoisomer thereof, a mixture of stereoisomers thereof, a mixture of different compounds (I) or a mixture of at least one compound of the formula (I) with one or both of the compounds of the formula (II.1) and/or (II.2), and at least one surfactant.

One embodiment of the invention is directed to a composition comprising a compound of formula (I), a stereoisomer thereof, a mixture of stereoisomers thereof, a mixture of different compounds (I) or a mixture of at least one compound of the formula (I) with one or both of the compounds of the formula (II.1) and/or (II.2), and at least one oil component.

One embodiment of the invention is directed to a composition comprising a compound of formula (I), a stereoisomer thereof, a mixture of stereoisomers thereof, a mixture of different compounds (I) or a mixture of at least one compound of the formula (I) with one or both of the compounds of the formula (II.1) and/or (II.2), and at least one solvent.

One embodiment of the invention is directed to a composition comprising a compound of formula (I), a stereoisomer thereof, a mixture of stereoisomers thereof, a mixture of different compounds (I) or a mixture of at least one compound of the formula (I) with one or both of the compounds of the formula (II.1) and/or (II.2), and at least one anti-oxidant.

One embodiment of the invention is directed to a composition comprising a compound of formula (I), a stereoisomer thereof, a mixture of stereoisomers thereof, a mixture of different compounds (I) or a mixture of at least one compound of the formula (I) with one or both of the compounds of the formula (II.1) and/or (II.2), and at least one deodorant-active agent.

The compound of formula (I), a stereoisomer thereof, a mixture of stereoisomers thereof, a mixture of different compounds (I) or a mixture of at least one compound of the formula (I) with one or both of the compounds of the formula (II.1) and/or (II.2) can preferably be used in aroma compositions. In preferred embodiments, the aroma composition is an odor composition, i.e. a composition inducing an odor impression, and is in particular a fragrance composition, i.e. a composition inducing a pleasant odor.

The composition according to the invention can be selected from, but is not limited to, the group consisting of perfume compositions, body care compositions (including cosmetic compositions), products for oral and dental hygiene, hygiene articles, cleaning compositions (including dishwashing compositions), textile detergent compositions, compositions for scent dispensers, foods, food supplements, pharmaceutical compositions and crop protection compositions.

Aroma Chemicals (Different from Compounds (I))

By virtue of the physical properties of the compounds (I), combinations of said compounds have particularly good, virtually universal solvent properties for and in aroma chemicals and other customary ingredients in aroma compositions such as, in particular, fragrance compositions. Therefore, the compound of formula (I), a stereoisomer thereof, a mixture of stereoisomers thereof, a mixture of different compounds (I) or a mixture of at least one compound of the formula (I) with one or both of the compounds of the formula (II.1) and/or (II.2) are well combinable with aroma chemicals which are different from compounds (I), (II.1) and (II.2) (including stereoisomers thereof), allowing, in particular, the creation of aroma compositions (preferably fragrance compositions) having novel advantageous sensory profiles. Especially, as already explained above, the combinations can boost the sensory profile of aroma chemicals (such as for example of fragrances) wherein said aroma chemicals are different from compounds (I), (II.1) and (II.2).

The compositions of the invention can comprise at least one aroma chemical that is different from compounds (I), (II.1) and (II.2). Said at least one aroma chemical can for example be 1, 2, 3, 4, 5, 6, 7, 8 or more aroma chemicals, selected from the group consisting of:

Geranyl acetate (3,7-dimethyl-2,6 octadien-1yl acetate), alpha-hexylcinnamaldehyde, 2-phenoxyethyl isobutyrate (Phenirat[1]), dihydromyrcenol (2,6-dimethyl-7-octen-2-ol), methyl dihydrojasmonate (preferably with a content of cis isomer of more than 60 wt. %) (Hedione[9], Hedione HC[9]), 4,6,6,7,8,8-hexamethyl-1,3,4,6,7,8-hexahydrocyclopenta[g]benzopyran (Galaxolid[3]), tetrahydrolinalool (3,7-dimethyl-octan-3-ol), ethyllinalool, benzyl salicylate, 2-methyl-3-(4-tert-butylphenyl)propanal (Lysmeral[2]), cinnamyl alcohol, 4,7-methano-3a,4,5,6,7,7a-hexahydro-5-indenyl acetate and/or 4,7-methano-3a,4,5,6,7,7a-hexahydro-6-indenyl acetate (Herbaflorat[1]), citronellol, citronellyl acetate, tetrahydrogeraniol, vanillin, linalyl acetate, styrolyl acetate (1-phenylethyl acetate), octahydro-2,3,8,8-tetramethyl-2-acetonaphthone and/or 2-acetyl-1,2,3,4,6,7,8-octahydro-2,3,8,8-tetramethylnaphthalene (Iso E Super[3]), hexyl salicylate, 4-tert-butylcyclohexyl acetate (Oryclone[1]), 2-tert-butylcyclohexyl acetate (Agrumex HC[1]), alpha-ionone (4-(2,2,6-trimethyl-2-cyclohexen-1-yl)-3-buten-2-one), n-alpha-methylionone, alpha-isomethylionone, coumarin, terpinyl acetate, 2-phenylethyl alcohol, 4-(4-hydroxy-4-methylpentyl)-3-cyclohexenecarboxaldehyde (Lyral[3]), alpha-amylcinnamaldehyde, ethylene brassylate, (E)- and/or (Z)-3-methylcyclopentadec-5-enone (Muscenon[9]), 15-pentadec-11-enolide and/or 15-pentadec-12-enolide (Globalide[1]), 15-cyclopentadecanolide (Macrolide[1]), 1-(5,6,7,8-tetrahydro-3,5,5,6,8,8-hexamethyl-2-naphthalenyl)ethanone (Tonalid[10]), 2-isobutyl-4-methyltetrahydro-2H-pyran-4-ol (Florol[9]), 2-ethyl-4-(2,2,3-trimethyl-3-cyclopenten-1-yl)-2-buten-1-ol (Sandolen[1]), cis-3-hexenyl acetate, trans-3-hexenyl acetate, trans-2/cis-6-nonadienol, 2,4-dimethyl-3-cyclohexenecarboxaldehyde (Vertocital[1]), 2,4,4,7-tetramethyloct-6-en-3-one (Claritone[1]), 2,6-dimethyl-5-hepten-1-al (Melonal[2]), borneol, 3-(3-isopropylphenyl)butanal (Florhydral[2]), 2-methyl-3-(3,4-methylenedioxyphenyl)propanal (Helional[3]), 3-(4-ethylphenyl)-2,2-dimethylpropanal (Florazon[1]), 7-methyl-2H-1,5-benzodioxepin-3(4H)-one (Calone), 3,3,5-trimethylcyclohexyl acetate (preferably with a content of cis isomers of 70 wt. %) or more, 2,5,5-trimethyl-1,2,3,4,4a,5,6,7-octahydronaphthalen-2-ol (Ambrinol S1), 3-(4-tert-butylphenyl)-propanal (Bourgeonal[4]), ethyl 2-methylpentanoate (Manzanate[4]), ethoxymethoxycyclododecane (Amberwood[1]), 2,4-dimethyl-4,4a,5,9b-tetrahydroindeno[1,2-d][1,3]dioxine (Magnolan[1]), (2-tert-butylcyclohexyl) acetate (Verdox[3]) and 3-[5,5,6-trimethylbicyclo[2.2.1]hept-2-yl]cyclohexan-1-ol (Sandela[4]). Within the context of the present invention, the aforementioned aroma chemical(s) are accordingly preferably combined with a compound of formula (I), a stereoisomer thereof, a mixture of stereoisomers thereof or a mixture of different compounds (I), as described above.

Where trade names are given above, these refer to the following sources:

[1]trade name of Symrise GmbH, Germany;
[2]trade name of BASF SE;
[3]trade name of International Flavors & Fragrances Inc., USA;
[4]Givaudan AG, Switzerland;
[9]trade name of Firmenich S.A., Switzerland;
[10]trade name of PFW Aroma Chemicals B.V., the Netherlands.

A preferred embodiment of the invention relates to a composition comprising a compound of formula (I), a stereoisomer thereof, a mixture of stereoisomers thereof, a mixture of different compounds (I) or a mixture of at least one compound of the formula (I) with one or both of the compounds of the formula (II.1) and/or (II.2), and at least one aroma chemical selected from the group consisting of methyl benzoate, benzyl acetate, geranyl acetate, 2-isobutyl-4-methyltetrahydro-2H-pyran-4-ol and linalool.

A further embodiment of the invention relates to a composition comprising a compound of formula (I), a stereoisomer thereof, a mixture of stereoisomers thereof, a mixture of different compounds (I) or a mixture of at least one compound of the formula (I) with one or both of the compounds of the formula (II.1) and/or (II.2), and 2-isobutyl-4-methyltetrahydro-2H-pyran-4-ol.

A further embodiment of the invention relates to a composition comprising a compound of formula (I), a stereoisomer thereof, a mixture of stereoisomers thereof, a mixture of different compounds (I) or a mixture of at least one compound of the formula (I) with one or both of the compounds of the formula (II.1) and/or (II.2), and methyl benzoate.

A preferred embodiment of the invention relates to a composition comprising a compound of formula (I), a stereoisomer thereof, a mixture of stereoisomers thereof, a mixture of different compounds (I) or a mixture of at least one compound of the formula (I) with one or both of the compounds of the formula (II.1) and/or (II.2), and at least one further aroma chemical selected from the group consisting of ethylvanillin, vanillin, 2,5-dimethyl-4-hydroxy-2H-furan-3-one (furaneol) or 3-hydroxy-2-methyl-4H-pyran-4-one (maltol).

Further aroma chemicals with which the compound of formula (I), a stereoisomer thereof, a mixture of stereoisomers thereof, a mixture of different compounds (I) or a mixture of at least one compound of the formula (I) with one or both of the compounds of the formula (II.1) and/or (II.2) can be combined to give a composition according to the invention can be found, e.g., in S. Arctander, Perfume and Flavor Chemicals, Vol. I and II, Montclair, N.J., 1969, self-published or K. Bauer, D. Garbe and H. Surburg, Common Fragrance and Flavor Materials, 4th Ed., Wiley-VCH, Weinheim 2001. Specifically, mention may be made of:

extracts from natural raw materials such as essential oils, concretes, absolutes, resins, resinoids, balsams, tinctures such as e.g.

ambergris tincture; amyris oil; angelica seed oil; angelica root oil; aniseed oil; valerian oil; basil oil; tree moss absolute; bay oil; mugwort oil; benzoin resin; bergamot oil; beeswax absolute; birch tar oil; bitter almond oil; savory oil; buchu leaf oil; cabreuva oil; cade oil; calmus oil; camphor oil; cananga oil; cardamom oil; cascarilla oil; cassia oil; cassia absolute; castoreum absolute; cedar leaf oil; cedar wood oil; cistus oil; citronella oil; lemon oil; copaiba balsam; copaiba balsam oil; coriander oil; costus root oil; cumin oil; cypress oil; davana oil; dill weed oil; dill seed oil; Eau de brouts absolute; oak moss absolute; elemi oil; tarragon oil; eucalyptus citriodora oil; eucalyptus oil; fennel oil; pine needle oil; galbanum oil; galbanum resin; geranium oil; grapefruit oil; guaiacwood oil; gurjun balsam; gurjun balsam oil; helichrysum absolute; helichrysum oil; ginger oil; iris root absolute; iris root oil; jasmine absolute; calmus oil; camomile oil blue; roman camomile oil; carrot seed oil; cascarilla oil; pine needle oil; spearmint oil; caraway oil; labdanum oil; labdanum absolute; labdanum resin; lavandin absolute; lavandin oil; lavender absolute; lavender oil; lemongrass oil; lovage oil; lime oil distilled; lime oil pressed; linalool oil; litsea cubeba oil; laurel leaf oil; mace oil; marjoram oil; mandarin oil; massoia bark oil; mimosa absolute; musk seed oil; musk tincture; clary sage oil; nutmeg oil; myrrh absolute; myrrh oil; myrtle oil; clove leaf oil; clove flower oil; neroli oil; olibanum absolute; olibanum oil; opopanax oil; orange blossom absolute; orange oil; origanum oil; palmarosa oil; patchouli oil; perilla oil; peru balsam oil; parsley leaf oil; parsley seed oil; petitgrain oil; peppermint oil; pepper oil; pimento oil; pine oil; pennyroyal oil; rose absolute; rose wood oil; rose oil; rosemary oil; Dalmatian sage oil; Spanish sage oil; sandalwood oil; celery seed oil; spike-lavender oil; star anise oil; styrax oil; tagetes oil; fir needle oil; tea tree oil; turpentine oil; thyme oil; tolubalsam; tonka absolute; tuberose absolute; vanilla extract; violet leaf absolute; verbena oil; vetiver oil; juniper berry oil; wine lees oil; wormwood oil; winter green oil; hyssop oil; civet absolute; cinnamon leaf oil; cinnamon bark oil, and fractions thereof, or ingredients isolated therefrom;

individual fragrances from the group of hydrocarbons, such as e.g. 3-carene; alphapinene; beta-pinene; alpha-terpinene; gamma-terpinene; p-cymene; bisabolene; camphene; caryophyllene; cedrene; farnesene; limonene; longifolene; myrcene; ocimene; valencene; (E,Z)-1,3,5-undecatriene; styrene; diphenylmethane;

the aliphatic alcohols such as e.g. hexanol; octanol; 3-octanol; 2,6-dimethylheptanol; 2-methyl-2-heptanol; 2-methyl-2-octanol; (E)-2-hexenol; (E)- and (Z)-3-hexenol; 1-octen-3-ol; mixture of 3,4,5,6,6-pentamethyl-3/4-hepten-2-ol and 3,5,6,6-tetramethyl-4-methyleneheptan-2-ol; (E,Z)-2,6-nonadienol; 3,7-dimethyl-7-methoxyoctan-2-ol; 9-decenol; 10-undecenol; 4-methyl-3-decen-5-ol;

the aliphatic aldehydes and acetals thereof such as e.g. hexanal; heptanal; octanal; nonanal; decanal; undecanal; dodecanal; tridecanal; 2-methyloctanal; 2-methylnonanal; (E)-2-hexenal; (Z)-4-heptenal; 2,6-dimethyl-5-heptenal; 10-undecenal; (E)-4-decenal; 2-dodecenal; 2,6,10-trimethyl-9-undecenal; 2,6,10-trimethyl-5,9-undecadienal; heptanal diethylacetal; 1,1-dimethoxy-2,2,5-trimethyl-4-hexene; citronellyloxyacetaldehyde; (E/Z)-1-(1-methoxypropoxy)-hex-3-ene; the aliphatic ketones and oximes thereof such as e.g. 2-heptanone; 2-octanone; 3-octanone; 2-nonanone; 5-methyl-3-heptanone; 5-methyl-3-heptanone oxime; 2,4,4,7-tetramethyl-6-octen-3-one; 6-methyl-5-hepten-2-one;

the aliphatic sulfur-containing compounds such as e.g. 3-methylthiohexanol; 3-methylthiohexyl acetate; 3-mercaptohexanol; 3-mercaptohexyl acetate; 3-mercaptohexyl butyrate; 3-acetylthiohexyl acetate; 1-menthene-8-thiol;

the aliphatic nitriles such as e.g. 2-nonenenitrile; 2-undecenenitrile; 2-tridecenenitrile; 3,12-tridecadienenitrile; 3,7-dimethyl-2,6-octadienenitrile; 3,7-dimethyl-6-octenenitrile;

the esters of aliphatic carboxylic acids such as e.g. (E)- and (Z)-3-hexenyl formate; ethyl acetoacetate; isoamyl acetate; hexyl acetate; 3,5,5-trimethylhexyl acetate; 3-methyl-2-butenyl acetate; (E)-2-hexenyl acetate; (E)- and (Z)-3-hexenyl acetate; octyl acetate; 3-octyl acetate; 1-octen-3-yl acetate; ethyl butyrate; butyl butyrate; isoamyl butyrate; hexyl butyrate; (E)- and (Z)-3-hexenyl isobutyrate; hexyl crotonate; ethyl isovalerate; ethyl 2-methylpentanoate; ethyl hexanoate; allyl hexanoate; ethyl heptanoate; allyl heptanoate; ethyl octanoate; ethyl (E,Z)-2,4-decadienoate; methyl 2-octinate; methyl 2-noninate; allyl 2-isoamyloxy acetate; methyl-3,7-dimethyl-2,6-octadienoate; 4-methyl-2-pentyl crotonate;

the acyclic terpene alcohols such as e.g. geraniol; nerol; linalool; lavandulol; nerolidol; farnesol; tetrahydrolinalool; 2,6-dimethyl-7-octen-2-ol; 2,6-dimethyloctan-2-ol; 2-methyl-6-methylene-7-octen-2-ol; 2,6-dimethyl-5,7-octadien-2-ol; 2,6-dimethyl-3,5-octadien-2-ol; 3,7-dimethyl-4,6-octadien-3-ol; 3,7-dimethyl-1,5,7-octatrien-3-ol; 2,6-dimethyl-2,5,7-octatrien-1-ol; and the formates, acetates, propionates, isobutyrates, butyrates, isovalerates, pentanoates, hexanoates, crotonates, tiglinates and 3-methyl-2-butenoates thereof;

the acyclic terpene aldehydes and ketones such as e.g. geranial; neral; citronellal; 7-hydroxy-3,7-dimethyloctanal; 7-methoxy-3,7-dimethyloctanal; 2,6,10-trimethyl-9-undecenal; geranyl acetone; as well as the dimethyl- and diethylacetals of geranial, neral, 7-hydroxy-3,7-dimethyloctanal; the cyclic terpene alcohols such as e.g. menthol; isopulegol; alpha-terpineol; terpine-4-ol; menthan-8-ol; menthan-1-ol; menthan-7-ol; borneol; isoborneol; linalool oxide; nopol; cedrol; ambrinol; vetiverol; guajol; and the formates, acetates, propionates, isobutyrates, butyrates, isovalerates, pentanoates, hexanoates, crotonates, tiglinates and 3-methyl-2-butenoates thereof;

the cyclic terpene aldehydes and ketones such as e.g. menthone; isomenthone; 8-mercaptomenthan-3-one; carvone; camphor; fenchone; alpha-ionone; beta-ionone; alpha-n-methylionone; beta-n-methylionone; alpha-isomethylionone; betaisomethylionone; alpha-irone; alpha-damascone; beta-damascone; betadamascenone; delta-damascone; gamma-damascone; 1-(2,4,4-trimethyl-2-cyclohexen-1-yl)-2-buten-1-one; 1,3,4,6,7,8a-hexahydro-1,1,5,5-tetramethyl-2H-2,4a-methanonaphthalene-8(5H)-one; 2-methyl-4-(2,6,6-trimethyl-1-cyclohexen-1-yl)-2-butenal; nootkatone; dihydronootkatone; 4,6,8-megastigmatrien-3-one; alpha-sinensal; betasinensal; acetylated cedar wood oil (methyl cedryl ketone);

the cyclic alcohols such as e.g. 4-tert-butylcyclohexanol; 3,3,5-trimethylcyclohexanol; 3-isocamphylcyclohexanol; 2,6,9-trimethyl-Z2,Z5,E9-cyclododecatrien-1-ol; 2-isobutyl-4-methyltetrahydro-2H-pyran-4-ol;

the cycloaliphatic alcohols such as e.g. alpha-3,3-trimethylcyclohexylmethanol; 1-(4-isopropylcyclohexyl)ethanol; 2-methyl-4-(2,2,3-trimethyl-3-cyclopent-1-yl)butanol; 2-methyl-4-(2,2,3-trimethyl-3-cyclopent-1-yl)-2-buten-1-ol; 2-ethyl-4-(2,2,3-trimethyl-3-cyclopent-1-yl)-2-buten-1-ol; 3-methyl-5-(2,2,3-trimethyl-3-cyclopent-1-yl)pentan-2-ol; 3-methyl-5-(2,2,3-trimethyl-3-cyclopent-1-yl)-4-penten-2-ol; 3,3-dimethyl-5-(2,2,3-trimethyl-3-cyclopent-1-yl)-4-penten-2-ol; 1-(2,2,6-trimethylcyclohexyl)pentan-3-ol; 1-(2,2,6-trimethylcyclohexyl)hexan-3-ol;

the cyclic and cycloaliphatic ethers such as e.g. cineol; cedryl methyl ether; cyclododecyl methyl ether; 1,1-dimethoxycyclododecane; (ethoxymethoxy)cyclododecane; alpha-cedrene epoxide; 3a,6,6,9a-tetramethyl-dodecahydronaphtho[2,1-b]furan; 3a-ethyl-6,6,9a-trimethyldodecahydronaphtho[2,1-b]furan; 1,5,9-trimethyl-13-oxabicyclo[10.1.0]trideca-4,8-diene; rose oxide; 2-(2,4-dimethyl-3-cyclohexen-1-yl)-5-methyl-5-(1-methylpropyl)-1,3-dioxane;

the cyclic and macrocyclic ketones such as e.g. 4-tert-butylcyclohexanone; 2,2,5-trimethyl-5-pentylcyclopentanone; 2-heptylcyclopentanone; 2-pentylcyclopentanone; 2-hydroxy-3-methyl-2-cyclopenten-1-one; 3-methyl-cis-2-penten-1-yl-2-cyclopenten-1-one; 3-methyl-2-pentyl-2-cyclopenten-1-one; 3-methyl-4-cyclopentadecenone; 3-methyl-5-cyclopentadecenone; 3-methylcyclopentadecanone; 4-(1-ethoxyvinyl)-3,3,5,5-tetramethylcyclohexanone; 4-tert-pentylcyclohexanone; 5-cyclohexadecen-1-one; 6,7-dihydro-1,1,2,3,3-pentamethyl-4(5H)-indanone; 8-cyclohexadecen-1-one; 7-cyclohexadecen-1-one; (7/8)-cyclohexadecen-1-one; 9-cycloheptadecen-1-one; cyclopentadecanone; cyclohexadecanone;

the cycloaliphatic aldehydes such as e.g. 2,4-dimethyl-3-cyclohexenecarbaldehyde; 2-methyl-4-(2,2,6-trimethylcyclohexen-1-yl)-2-butenal; 4-(4-hydroxy-4-methylpentyl)-3-cyclohexene carbaldehyde; 4-(4-methyl-3-penten-1-yl)-3-cyclohexenecarbaldehyde; the cycloaliphatic ketones such as e.g. 1-(3,3-dimethylcyclohexyl)-4-penten-1-one; 2,2-dimethyl-1-(2,4-dimethyl-3-cyclohexen-1-yl)-1-propanone; 1-(5,5-dimethyl-1-cyclohexen-1-yl)-4-penten-1-one; 2,3,8,8-tetramethyl-1,2,3,4,5,6,7,8-octahydro-2-naphthalenyl methyl ketone; methyl 2,6,10-trimethyl-2,5,9-cyclododecatrienyl ketone; tert-butyl (2,4-dimethyl-3-cyclohexen-1-yl) ketone;

the esters of cyclic alcohols such as e.g. 2-tert-butylcyclohexyl acetate; 4-tert-butylcyclohexyl acetate; 2-tert-pentylcyclohexyl acetate; 4-tert-pentylcyclohexyl acetate; 3,3,5-trimethylcyclohexyl acetate; decahydro-2-naphthyl acetate; 2-cyclopentylcyclopentyl crotonate; 3-pentyltetrahydro-2H-pyran-4-yl acetate; decahydro-2,5,5,8a-tetramethyl-2-naphthyl acetate; 4,7- methano-3a,4,5,6,7,7a-hexahydro-5 or 6-indenyl acetate; 4,7-methano-3a,4,5,6,7,7a-hexahydro-5 or 6-indenyl propionate; 4,7-methano-3a,4,5,6,7,7a-hexahydro-5 or 6-indenyl isobutyrate; 4,7-methanooctahydro-5 or 6-indenyl acetate;

the esters of cycloaliphatic alcohols such as e.g. 1-cyclohexylethyl crotonate;

the esters of cycloaliphatic carboxylic acids such as e.g. allyl 3-cyclohexylpropionate; allyl cyclohexyloxyacetate; cis- and trans-methyl dihydrojasmonate; cis- and trans-methyl jasmonate; methyl 2-hexyl-3-oxocyclopentanecarboxylate; ethyl 2-ethyl-6,6-dimethyl-2-cyclohexenecarboxylate; ethyl 2,3,6,6-tetramethyl-2-cyclohexenecarboxylate; ethyl 2-methyl-1,3-dioxolane-2-acetate;

the araliphatic alcohols such as e.g. benzyl alcohol; 1-phenylethyl alcohol, 2-phenylethyl alcohol, 3-phenylpropanol; 2-phenylpropanol; 2-phenoxyethanol; 2,2-dimethyl-3-phenylpropanol; 2,2-dimethyl-3-(3-methylphenyl)propanol; 1,1-dimethyl-2-phenylethyl alcohol; 1,1-dimethyl-3-phenylpropanol; 1-ethyl-1-methyl-3-phenylpropanol; 2-methyl-5-phenylpentanol; 3-methyl-5-phenylpentanol; 3-phenyl-2-propen-1-ol; 4-methoxybenzyl alcohol; 1-(4-isopropylphenyl)ethanol;

the esters of araliphatic alcohols and aliphatic carboxylic acids such as e.g. benzyl acetate; benzyl propionate; benzyl isobutyrate; benzyl isovalerate; 2-phenylethyl acetate; 2-phenylethyl propionate; 2-phenylethyl isobutyrate; 2-phenylethyl isovalerate; 1-phenylethyl acetate; alpha-trichloromethylbenzyl acetate; alpha,alpha-dimethylphenylethyl acetate; alpha,alpha-dimethylphenylethyl butyrate; cinnamyl acetate; 2-phenoxyethyl isobutyrate; 4-methoxybenzyl acetate;

the araliphatic ethers such as e.g. 2-phenylethyl methyl ether; 2-phenylethyl isoamyl ether; 2-phenylethyl 1-ethoxyethyl ether; phenylacetaldehyde dimethyl acetal; phenylacetaldehyde diethyl acetal; hydratropaaldehyde dimethyl acetal; phenylacetaldehyde glycerol acetal; 2,4,6-trimethyl-4-phenyl-1,3-dioxane; 4,4a,5,9b-tetrahydroindeno[1,2-d]-m-dioxine; 4,4a,5,9b-tetrahydro-2,4-dimethylindeno[1,2-d]-m-dioxine;

the aromatic and araliphatic aldehydes such as e.g. benzaldehyde; phenylacetaldehyde; 3-phenylpropanal; hydratropaaldehyde; 4-methylbenzaldehyde; 4-methylphenylacetaldehyde; 3-(4-ethylphenyl)-2,2-dimethylpropanal; 2-methyl-3-(4-isopropylphenyl)propanal; 2-methyl-3-(4-tert-butylphenyl)propanal; 2-methyl-3-(4-isobutylphenyl)propanal; 3-(4-tert-butylphenyl)propanal; cinnamaldehyde; alpha-butylcinnamaldehyde; alpha-amylcinnamaldehyde; alpha-hexylcinnamaldehyde; 3-methyl-5-phenylpentanal; 4-methoxybenzaldehyde; 4-hydroxy-3-methoxybenzaldehyde; 4-hydroxy-3-ethoxybenzaldehyde; 3,4-methylenedioxybenzaldehyde; 3,4-dimethoxybenzaldehyde; 2-methyl-3-(4-methoxyphenyl)propanal; 2-methyl-3-(4-methylenedioxyphenyl)propanal;

the aromatic and araliphatic ketones such as e.g. acetophenone; 4-methylacetophenone; 4-methoxyacetophenone; 4-tert-butyl-2,6-dimethylacetophenone; 4-phenyl-2-butanone; 4-(4-hydroxyphenyl)-2-butanone; 1-(2-naphthalenyl)ethanone; 2-benzofuranylethanone; (3-methyl-2-benzofuranyl)ethanone; benzophenone; 1,1,2,3,3,6-hexamethyl-5-indanyl methyl ketone; 6-tert-butyl-1,1-dimethyl-4-indanyl methyl ketone; 1-[2,3-dihydro-1,1,2,6-tetramethyl-3-(1-methylethyl)-1H5-indenyl]ethanone; 5',6',7',8'-tetrahydro-3',5',5',6',8',8'-hexamethyl-2-acetonaphthone;

the aromatic and araliphatic carboxylic acids and esters thereof such as e.g. benzoic acid; phenylacetic acid; methyl benzoate; ethyl benzoate; hexyl benzoate; benzyl benzoate; methyl phenylacetate; ethyl phenylacetate; geranyl phenylacetate; phenylethyl phenylacetate; methyl cinnamate; ethyl cinnamate; benzyl cinnamate; phenylethyl cinnamate; cinnamyl cinnamate; allyl phenoxyacetate; methyl salicylate; isoamyl salicylate; hexyl salicylate; cyclohexyl salicylate; cis-3-hexenyl salicylate; benzyl salicylate; phenylethyl salicylate; methyl 2,4-dihydroxy-3,6-dimethylbenzoate; ethyl 3-phenylglycidate; ethyl 3-methyl-3-phenylglycidate;

the nitrogen-containing aromatic compounds such as e.g. 2,4,6-trinitro-1,3-dimethyl-5-tert-butylbenzene; 3,5-dinitro-2,6-dimethyl-4-tert-butylacetophenone; cinnamonitrile; 3-methyl-5-phenyl-2-pentenonitrile; 3-methyl-5-phenylpentanonitrile; methyl anthranilate; methyl-N-methylanthranilate; Schiff bases of methyl anthranilate with 7-hydroxy-3,7-dimethyloctanal, 2-methyl-3-(4-tert-butylphenyl)propanal or 2,4-dimethyl-3-cyclohexenecarbaldehyde; 6-isopropylquinoline; 6-isobutylquinoline; 6-sec-butylquinoline; 2-(3-phenylpropyl)pyridine; indole; skatole; 2-methoxy-3-isopropylpyrazine; 2-isobutyl-3-methoxypyrazine;

the phenols, phenyl ethers and phenyl esters such as e.g. estragole; anethole; eugenol; eugenyl methyl ether; isoeugenol; isoeugenyl methyl ether; thymol; carvacrol; diphenyl ether; beta-naphthyl methyl ether; beta-naphthyl ethyl ether; beta-naphthyl isobutyl ether; 1,4-dimethoxybenzene; eugenyl acetate; 2-methoxy-4-methylphenol; 2-ethoxy-5-(1-propenyl)phenol; p-cresyl phenylacetate;

the heterocyclic compounds such as e.g. 2,5-dimethyl-4-hydroxy-2H-furan-3-one; 2-ethyl-4-hydroxy-5-methyl-2H-furan-3-one; 3-hydroxy-2-methyl-4H-pyran-4-one; 2-ethyl-3-hydroxy-4H-pyran-4-one;

the lactones such as e.g. 1,4-octanolide; 3-methyl-1,4-octanolide; 1,4-nonanolide; 1,4-decanolide; 8-decen-1,4-olide; 1,4-undecanolide; 1,4-dodecanolide; 1,5-decanolide; 1,5-dodecanolide; 4-methyl-1,4-decanolide; 1,15-pentadecanolide; cis- and trans-11-pentadecen-1,15-olide; cis- and trans-12-pentadecen-1,15-olide; 1,16-hexadecanolide; 9-hexadecen-1,16-olide; 10-oxa-1,16-hexadecanolide; 11-oxa-1,16-hexadecanolide; 12-oxa-1,16-hexadecanolide; ethylene 1,12-dodecanedioate; ethylene 1,13-tridecanedioate; coumarin; 2,3-dihydrocoumarin; octahydrocoumarin.

Non-Aroma Chemical Carriers

A further embodiment of the invention is directed to a composition comprising a compound of formula (I), a stereoisomer thereof, a mixture of stereoisomers thereof or a mixture of different compounds (I), and at least one non-aroma chemical carrier.

The at least one non-aroma chemical carrier can be a compound, a mixture of compounds or other additives, which has/have no or no noteworthy sensory properties. The non-aroma chemical carrier can serve for the dilution and/or the fixing of the compound (I) and optionally the at least one aroma chemical, as defined above, or any other component, if comprised in the composition.

A further embodiment of the invention is directed to a composition comprising a compound of formula (I), a stereoisomer thereof, a mixture of stereoisomers thereof or a mixture of different compounds (I), and at least one non-aroma chemical carrier selected from the group consisting of solvents, surfactants and oil components.

According to preferred embodiments of the present invention, said non-aroma chemical carrier(s) is/are selected from the solvents, surfactants and oil components listed below.

One embodiment of the invention is directed to a composition comprising a compound of formula (I), a stereoisomer thereof, a mixture of stereoisomers thereof or a mixture of different compounds (I), as described herein and at least one solvent.

In the context of the present invention, a "solvent" serves for the dilution of the compound(s) (I) to be used according to the invention and/or any further component of the composition without having its own aroma.

The one or more solvent(s) can be present in the composition in amount of 0.01 to 99 wt. % based on the composition. In a preferred embodiment of the invention, the composition comprises 0.1 to 90 wt. %, preferably 0.5 to 80 wt. % of solvent(s) based on the total weight of the composition. The amount of solvent(s) can be chosen depending on the composition. In one embodiment of the invention, the composition comprises 0.05 to 10 wt. %, preferably 0.1 to 5 wt. %, more preferably 0.2 to 3 wt. % based on the total weight of the composition. In one embodiment of the invention, the composition comprises 20 to 70 wt. %, preferably 25 to 50 wt. % of solvent(s) based on the total weight of the composition.

Preferred solvents are ethanol, isopropanol, dipropylene glycol (DPG), propylene glycol, 1,2-butylene glycol, glycerol, diethylene glycol monoethyl ether, diethyl phthalate (DEP), isopropyl myristate (IPM), triethyl citrate (TEC), and benzyl benzoate (BB).

Especially preferred solvents are selected from the group consisting of ethanol, propylene glycol, dipropylene glycol, triethyl citrate, benzyl benzoate and isopropyl myristate.

In a preferred embodiment of the invention, the solvent is selected from the group consisting of ethanol, isopropanol, diethylene glycol monoethyl ether, glycerol, propylene glycol, 1,2-butylene glycol, dipropylene glycol, triethyl citrate and isopropyl myristate.

According to a further embodiment, the compound of formula (I), a stereoisomer thereof, a mixture of stereoisomers thereof, a mixture of different compounds (I) or a mixture of at least one compound of the formula (I) with one or both of the compounds of the formula (II.1) and/or (II.2), is used according to the present invention in surfactant-containing compositions. Due to its characteristic fragrance property and its substantivity, tenacity as well as stability, the compound of formula (I), a stereoisomer thereof, a mixture of stereoisomers thereof, a mixture of different compounds (I) or a mixture of at least one compound of the formula (I) with one or both of the compounds of the formula (II.1) and/or (II.2) can especially be used to provide an odor, preferably a fragrance impression to surfactant-containing compositions such as, for example, cleaners (in particular laundry care products and all-purpose cleaners). It can preferably be used to impart a long-lasting clean note to a surfactant comprising composition.

One embodiment of the invention is therefore directed to a composition comprising a compound of formula (I), a stereoisomer thereof, a mixture of stereoisomers thereof, a mixture of different compounds (I) or a mixture of at least one compound of the formula (I) with one or both of the compounds of the formula (II.1) and/or (II.2), and at least one surfactant.

The surfactant(s) may be selected from anionic, nonionic, cationic and/or amphoteric or zwitterionic surfactants.

Surfactant-containing compositions, such as for example shower gels, foam baths, shampoos, etc., preferably contain at least one anionic surfactant.

The compositions according to the invention usually contain the surfactant(s), in the aggregate, in an amount of 0 to 40 wt. %, preferably 0 to 20 wt. %, more preferably 0.1 to 15 wt. %, and particularly 0.1 to 10 wt. %, based on the total weight of the composition. Typical examples of nonionic surfactants are fatty alcohol polyglycol ethers, alkylphenol polyglycol ethers, fatty acid polyglycol esters, fatty acid amide polyglycol ethers, fatty amine polyglycol ethers, alkoxylated triglycerides, mixed ethers and mixed formals, optionally partly oxidized alk(en)yl oligoglycosides or glucuronic acid derivatives, fatty acid-N-alkyl glucamides, protein hydrolyzates (particularly wheat-based vegetable products), polyol fatty acid esters, sugar esters, sorbitan esters, polysorbates and amine oxides. If the nonionic surfactants contain polyglycol ether chains, they may have a conventional homolog distribution, although they preferably have a narrow-range homolog distribution.

Zwitterionic surfactants are surface-active compounds which contain at least one quaternary ammonium group and at least one —COOH$^{(-)}$ or —SO$_3^{(-)}$ group in the molecule. Particularly suitable zwitterionic surfactants are the so-called betaines, such as the N-alkyl-N,N-dimethyl ammonium glycinates, for example, cocoalkyl dimethyl ammonium glycinate, N-acylaminopropyl-N,N-dimethyl ammonium glycinates, for example, co-coacylaminopropyl dimethyl ammonium glycinate, and 2-alkyl-3-carboxymethyl-3-hydroxyethyl imidazolines, containing 8 to 18 carbon atoms in the alkyl or acyl group, and cocoacylaminoethyl hydroxyethyl carboxymethyl glycinate. The fatty acid amide derivative known under the CTFA name of Cocamidopropyl Betaine is particularly preferred.

Ampholytic surfactants are also suitable, particularly as co-surfactants. Ampholytic surfactants are surface-active compounds which, in addition to a $C_8$ to $C_{18}$ alkyl or acyl group, contain at least one free amino group and at least one —COOH— or —SO$_3$H— group in the molecule and which are capable of forming inner salts. Examples of suitable ampholytic surfactants are N-alkyl glycines, N-alkyl propionic acids, N-alkylaminobutyric acids, N-alkyliminodipropionic acids, N-hydroxyethyl-N-alkylamidopropyl glycines, N-alkyl taurines, N-alkyl sarcosines, 2-alkylaminopropionic acids and alkylaminoacetic acids containing around 8 to 18 carbon atoms in the alkyl group. Particularly preferred ampholytic surfactants are N-cocoalkylaminopropionate, cocoacylaminoethyl aminopropionate and acyl sarcosine.

Anionic surfactants are characterized by a water-solubilizing anionic group such as, for example, a carboxylate, sulfate, sulfonate or phosphate group and a lipophilic group. Dermatologically safe anionic surfactants are known to the practitioner in large numbers from relevant textbooks and are commercially available. They are, in particular, alkyl sulfates in the form of their alkali metal, ammonium or alkanolammonium salts, alkylether sulfates, alkylether carboxylates, acyl isethionates, acyl sarcosinates, acyl taurines containing linear $C_{12}$-$C_{18}$ alkyl or acyl groups and sulfosuccinates and acyl glutamates in the form of their alkali metal or ammonium salts.

Particularly suitable cationic surfactants are quaternary ammonium compounds, preferably ammonium halides, more especially chlorides and bromides, such as alkyl trimethyl ammonium chlorides, dialkyl dimethyl ammonium chlorides and trialkyl methyl ammonium chlorides, for example, cetyl trimethyl ammonium chloride, stearyl trimethyl ammonium chloride, distearyl dimethyl ammonium chloride, lauryl dimethyl ammonium chloride, lauryl dimethyl benzyl ammonium chloride and tricetyl methyl ammonium chloride. In addition, the readily biodegradable quaternary ester compounds, such as, for example, the dialkyl ammonium methosulfates and methyl hydroxyalkyl dialkoyloxyalkyl ammonium methosulfates marketed under the name of Stepantexe and the corresponding products of the Dehyquart® series, may be used as cationic surfactants. "Esterquats" are generally understood to be quaternized fatty acid triethanolamine ester salts. They can provide the compositions with particular softness. They are known substances which are prepared by the relevant methods of organic chemistry. Other cationic surfactants suitable for use in accordance with the invention are the quaternized protein hydrolyzates.

One embodiment of the invention is directed to a composition comprising a compound of formula (I), a stereoisomer thereof, a mixture of stereoisomers thereof or a mixture of different compounds (I), and at least one oil component.

The oil components are typically present in an amount of 0.1 to 80 wt. %, preferably 0.5 to 70 wt. %, more preferably 1 to 60 wt. %, even more preferably 1 to 50 wt. %, in particular 1 to 40 wt. %, more particularly 5 to 25 wt. % and specifically 5 to 15 wt. % based on the total weight of the composition.

The oil components may be selected, for example, from Guerbet alcohols based on fatty alcohols containing 6 to 18, preferably 8 to 10, carbon atoms and other additional esters, such as myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Also suitable are esters of $C_{18}$-$C_{38}$ alkyl-hydroxycarboxylic acids with linear or branched $C_6$-$C_{22}$ fatty alcohols, more especially dioctyl malate, esters of linear and/or branched fatty acids with polyhydric alcohols (for example propylene glycol, dimer dial or trimer triol), triglycerides based on $C_6$-$C_{10}$ fatty acids, liquid mono-, di- and triglyceride mixtures based on $C_6$-$C_1$ fatty acids, esters of $C_6$-$C_{22}$ fatty alcohols and/or Guerbet alcohols with aromatic carboxylic acids, more particularly benzoic acid, esters of dicarboxylic acids with polyols containing 2 to 10 carbon atoms and 2 to 6 hydroxyl groups, vegetable oils, branched primary alcohols, substituted cyclohexanes, linear and branched $C_6$-$C_{22}$ fatty alcohol carbonates such as, for example, dicaprylyl carbonate (Cetiol® CC), Guerbet carbonates based on fatty alcohols containing 6 to 18, preferably 8 to 10, carbon atoms, esters of benzoic acid with linear and/or branched $C_6$ to $C_{22}$ alcohols (for example Finsolv® TN), linear or branched, symmetrical or nonsymmetrical dialkyl ethers containing 6 to 22 carbon atoms per alkyl group such as, for example, dicaprylyl ether (Cetiol® OE), ring opening products of epoxidized fatty acid esters with polyols and hydrocarbons or mixtures thereof.

Anti-Oxidants

One embodiment of the invention is directed to a composition comprising a compound of formula (I), a stereoisomer thereof, a mixture of stereoisomers thereof, a mixture of different compounds (I) or a mixture of at least one compound of the formula (I) with one or both of the compounds of the formula (II.1) and/or (II.2), and at least one anti-oxidant.

Anti-oxidants are able to inhibit or prevent the undesired changes in the compositions to be protected caused by oxygen effects and other oxidative processes. The effect of the anti-oxidants consists in most cases in them acting as free-radical scavengers for the free radicals which arise during autoxidation.

Anti-oxidants can for example be selected from the group consisting of
    amino acids (for example glycine, alanine, arginine, serine, threonine, histidine, tyrosine, tryptophan) and derivatives thereof,
    imidazoles (e.g. urocanic acid) and derivatives thereof,
    peptides, such as D,L-carnosine, D-carnosine, L-carnosine (=β-Alanyl-L-histidin) and derivatives thereof
    carotenoids, carotenes (e.g. alpha-carotene, beta-carotene, lycopene, lutein) or derivatives thereof,
    chlorogenic acid and derivatives thereof,
    lipoic acid and derivatives thereof (for example dihydrolipoic acid),
    auro-thioglucose, propylthiouracil and other thiols (for example thioredoxin, glutathione, cysteine, cystine, cystamine and the glycosyl, N-acetyl, methyl, ethyl, propyl, amyl, butyl and lauryl, palmitoyl, oleyl, gamma-linoleyl, cholesteryl and glyceryl esters thereof) and salts thereof,
    dilauryl thiodipropionate, distearyl thiodipropionate, thiodipropionic acid and derivatives thereof (esters, ethers, peptides, lipids, nucleotides, nucleosides and salts),
    sulfoximine compounds (for example buthionine sulfoximines, homocysteine sulfoximine, buthionine sulfones, penta-, hexa-, heptathionine sulfoximine)
    (metal) chelating agents (e.g. alpha-hydroxy fatty acids, palmitic acid, phytic acid, lactoferrin),
    alpha-hydroxy acids (for example citric acid, lactic acid, malic acid),
    humic acid, bile acid, bile extracts, bilirubin, biliverdin, boldin (=alkaloid from the plant Peumus boldus, boldo extract,
    EDTA, EGTA and derivatives thereof,
    unsaturated fatty acids and derivatives thereof (e.g. gamma-linolenic acid, linoleic acid, oleic acid),
    folic acid and derivatives thereof,
    ubiquinone and ubiquinol and derivatives thereof,
    vitamin C and derivatives (for example ascorbyl palmitate, Mg ascorbyl phosphate, ascorbyl acetate),
    tocopherols and derivatives (for example vitamin E acetate),
    vitamin A and derivatives (for example vitamin A palmitate),
    coniferyl benzoate of gum benzoin, rutic acid and derivatives thereof, alpha-glycosylrutin, ferulic acid, furfurylideneglucitol,
    butylhydroxytoluene (BHT), butylhydroxyanisole (BHA)
    nordihydroguaiacic acid, nordihydroguaiaretic acid, trihydroxybutyrophenone, uric acid and derivatives thereof, mannose and derivatives thereof,
    superoxide dismutase
    zinc and derivatives thereof (for example ZnO, ZnSO4),
    selenium and derivatives thereof (for example selenomethionine) and stilbenes and derivatives thereof (e.g. stilbene oxide, trans-stilbene oxide)

In a preferred embodiment, the anti-oxidant is selected from the group consisting of pentaerythrityl, tetra-di-t-butyl hydroxyhydrocinnamate, nordihydroguaiaretic acid, ferulic acid, resveratrol, propyl gallate, butylhydroxytoluene (BHT), butylhydroxyanisole (BHA), ascorbyl palmitate and tocopherol.

The compositions according to the invention can comprise the anti-oxidants in an amount of 0.001 to 25 wt.-%, preferably 0.005 to 10 wt.-%, preferably 0.01 to 8 wt.-%, preferably 0.025 to 7 wt.-%, preferably 0.05 to 5 wt.-%, based on the total weight of the composition.

Deodorant-Active Agents

One embodiment of the invention is directed to a composition comprising a compound of formula (I), a stereoisomer thereof, a mixture of stereoisomers thereof, a mixture of different compounds (I) or a mixture of at least one compound of the formula (I) with one or both of the compounds of the formula (II.1) and/or (II.2), and at least one deodorant-active agent.

The compounds (I), their stereoisomers, mixtures of stereoisomers thereof, mixtures of different compounds (I) and mixtures of at least one compound of the formula (I) with one or both of the compounds of the formula (II.1) and/or (II.2) can be used to impart a clean, long-lasting note to deodorizing compositions as well as to the skin treated with such compositions.

Deodorizing compositions (deodorants and antiperspirants) counteract, mask or eliminate body odors. Body odors are formed through the action of skin bacteria on apocrine perspiration which results in the formation of unpleasant-smelling degradation products.

In a preferred embodiment of the invention, the at least one deodorant-active agent is selected from the groups consisting of anti-perspirants, esterase inhibitors and anti-bacterial agents.

Suitable antiperspirants can be selected from the group consisting of salts of aluminium, zirconium or zinc. Examples are aluminium chloride, aluminium chlorohydrate, aluminium dichlorohydrate, aluminium sesquichlorohydrate and complex compounds thereof, for example with 1,2-propylene glycol, aluminium hydroxyallantoinate, aluminium chloride tartrate, aluminium zirconium trichlorohydrate, aluminium zirconium tetrachlorohydrate, aluminium zirconium pentachlorohydrate and complex compounds thereof, for example with amino acids, such as glycine. Aluminium chlorohydrate, aluminium zirconium tetrachlorohydrate, aluminium zirconium pentachlorohydrate and complex compounds thereof are preferably used.

In a preferred embodiment of the invention the compositions comprise at least one antiperspirant selected from the group consisting aluminium chloride, aluminium chlorohydrate, aluminium dichlorohydrate, aluminium sesquichlorohydrate, aluminium hydroxyallantoinate, aluminium chloride tartrate, aluminium zirconium trichlorohydrate, aluminium zirconium tetrachlorohydrate and aluminium zirconium pentachlorohydrate The compositions according to the invention can comprise the antiperspirants in an amount of 1 to 50, preferably 5 to 30 and more particularly 10 to 25 wt.-%, based on the solids content of the composition.

Where perspiration is present in the underarm region, extracellular enzymes-esterases, mainly proteases and/or lipases are formed by bacteria and split the esters present in the perspiration, releasing odors in the process. Suitable esterase inhibitors are for example trialkyl citrates, such as trimethyl citrate, tripropyl citrate, triisopropyl citrate, tributyl citrate and, in particular, triethyl citrate. Esterase inhibitors inhibit enzyme activity and thus reduce odor formation. The free acid is probably released by the cleavage of the citric acid ester and reduces the pH value of the skin to such an extent that the enzymes are inactivated by acylation. Other esterase inhibitors are sterol sulfates or phosphates such as, for example, lanosterol, cholesterol, campesterol, stigmasterol and sitosterol sulfate or phosphate, dicarboxylic acids and esters thereof, for example glutaric acid, glutaric acid monoethyl ester, glutaric acid diethyl ester, adipic acid, adipic acid monoethyl ester, adipic acid diethyl ester, malonic acid and malonic acid diethyl ester, hydroxycarboxylic acids and esters thereof, for example citric acid, malic acid, tartaric acid or tartaric acid diethyl ester, and zinc glycinate.

In a preferred embodiment of the invention the compositions comprise at least one esterase inhibitor selected from the group consisting of trimethyl citrate, tripropyl citrate, triisopropyl citrate, tributyl citrate triethyl citrate, lanosterol, cholesterol, campesterol, stigmasterol, sitosterol sulfate, sitosterol phosphate, glutaric acid, glutaric acid monoethyl ester, glutaric acid diethyl ester, adipic acid, adipic acid monoethyl ester, adipic acid diethyl ester, malonic acid, malonic acid diethyl ester, citric acid, malic acid, tartaric acid, tartaric acid diethyl ester and zinc glycinate.

The compositions according to the invention can comprise the esterase inhibitors in amounts of 0.01 to 20, preferably 0.1 to 10 and more particularly 0.5 to 5 wt.-%, based on the solids content of the composition.

The term "anti-bacterial agents" as used herein encompasses substances which have bactericidal and/or bacteriostatic properties. Typically these substances act against gram-positive bacteria such as, for example, 4-hydroxybenzoic acid and salts and esters thereof, N-(4-chlorophenyl)-N'-(3,4-dichlorophenyl)-urea, 2,4,4'-trichloro-2'-hydroxydiphenylether (triclosan), 4-chloro-3,5-dimethylphenol, 2,2'-methylene-bis-(6-bromo-4-chlorophenol), 3-methyl-4-(1-methylethyl)-phenol, 2-benzyl-4-chlorophenol, 3-(4-chlorophenoxy)-propane-1,2-diol, 3-iodo-2-propinyl butyl carbamate, chlorhexidine, 3,4,4'-trichlorocarbanilide (TTC), phenoxyethanol, glycerol monocaprate, glycerol monocaprylate, glycerol monolaurate (GML), diglycerol monocaprate (DMC), salicylic acid-N-alkylamides such as, for example, salicylic acid-n-octyl amide or salicylic acid-n-decyl amide.

In a preferred embodiment the antibacterial agent is selected from the group consisting of chitosan, phenoxyethanol, 5-Chloro-2-(2,4-dichlorophenoxy)-phenol, 4-hydroxybenzoic acid and salts and esters thereof, N-(4-chlorophenyl)-N'-(3,4-dichlorophenyl)-urea, 2,4,4'-trichloro-2'-hydroxydiphenylether (triclosan), 4-chloro-3,5-dimethylphenol, 2,2'-methylene-bis-(6-bromo-4-chlorophenol), 3-methyl-4-(1-methylethyl)-phenol, 2-benzyl-4-chlorophenol, 3-(4-chlorophenoxy)-propane-1,2-diol, 3-iodo-2-propinyl butyl carbamate, chlorhexidine, 3,4,4'-trichlorocarbanilide (TTC), phenoxyethanol, glycerol monocaprate, glycerol monocaprylate, glycerol monolaurate (GML), diglycerol monocaprate (DMC), salicylic acid-N-alkylamides.

The compositions according to the invention can comprise the antibacterial agents in amounts of 0.01 to 5 wt. % and preferably 0.1 to 2 wt.-%, based on the solids content of the composition.

The compositions according to the invention can further comprise one or more substances, such as, for example: preservatives, abrasives, anti-acne agents, agents to combat skin aging, anti-cellulite agents, antidandruff agents, anti-inflammatory agents, irritation-preventing agents, irritation-alleviating agents, astringents, sweat-inhibiting agents, anti-septics, anti-statics, binders, buffers, carrier materials, chelating agents, cell stimulants, care agents, hair removal agents, emulsifiers, enzymes, essential oils, fibers, film formers, fixatives, foam formers, foam stabilizers, substances for preventing foaming, foam boosters, fungicides, gelling agents, gel-forming agents, hair care agents, hair shaping agents, hair smoothing agents, moisture-donating agents, moisturizing substances, humectant substances, bleaching agents, strengthening agents, stain removal agents, optical brighteners, impregnating agents, soil repellents, friction-reducing agents, lubricants, moisturizing creams, ointments, opacifiers, plasticizers, covering agents, polish, shine agents, polymers, powders, proteins, refatting agents, exfoliating agents, silicones, skin-calming agents, skin-cleansing agents, skin care agents, skin-healing agents, skin lightening agents, skin-protective agents, skin-softening agents, cooling agents, skin-cooling agents, warming agents, skin-warming agents, stabilizers, UV-absorbent agents, UV filters, fabric softeners, suspending agents, skin-tanning agents, thickeners, vitamins, waxes, fats, phospholipids, saturated fatty acids, mono- or polyunsaturated fatty acids, α-hydroxy acids, polyhydroxy fatty acids, liquefiers, dyes, color-protection agents, pigments, anti-corrosives, polyols, electrolytes, or silicone derivatives.

The compound of formula (I), a stereoisomer thereof, a mixture of stereoisomers thereof, a mixture of different compounds (I) or a mixture of at least one compound of the formula (I) with one or both of the compounds of the formula (II.1) and/or (II.2), as described herein can be used in a wide range of compositions, preferably in aroma compositions, more preferably in fragrance compositions. The olfactory properties and the substance properties (such as solubility in customary solvents and compatibility with further customary constituents of such compositions) of the compounds (I) underline the particular suitability of the combinations for the stated use purposes and compositions.

Suitable compositions are for example perfume compositions, body care compositions (including cosmetic compositions), products for oral and dental hygiene, hygiene articles, cleaning compositions (including dishwashing compositions), textile detergent compositions, compositions for scent dispensers, foods, food supplements, pharmaceutical compositions and crop protection compositions.

Perfume compositions can be selected from fine fragrances, air fresheners in liquid form, gel-like form or a form applied to a solid carrier, aerosol sprays, scented cleaners, perfume candles and oils, such as lamp oils or oils for massage.

Examples for fine fragrances are perfume extracts, Eau de Parfums, Eau de Toilettes, Eau de Colognes, Eau de Solide and Extrait Parfum.

Body care compositions include cosmetic compositions, and can be selected from after-shaves, pre-shave products, splash colognes, solid and liquid soaps, shower gels, shampoos, shaving soaps, shaving foams, bath oils, cosmetic emulsions of the oil-in-water type, of the water-in-oil type and of the water-in-oil-in-water type, such as e.g. skin creams and lotions, face creams and lotions, sunscreen creams and lotions, after-sun creams and lotions, hand creams and lotions, foot creams and lotions, hair removal creams and lotions, after-shave creams and lotions, tanning creams and lotions, hair care products such as e.g. hair-sprays, hair gels, setting hair lotions, hair conditioners, hair shampoo, permanent and semi-permanent hair colorants, hair shaping compositions such as cold waves and hair smoothing compositions, hair tonics, hair creams and hair lotions, deodorants and antiperspirants such as e.g. underarm sprays, roll-ons, deodorant sticks and deodorant creams, products of decorative cosmetics such as e.g. eye-liners, eye-shadows, nail varnishes, make-ups, lipsticks and mascara.

Products for oral and dental hygiene can be selected from toothpaste, dental floss, mouth wash, breath fresheners, dental foam, dental gels and dental strips.

Hygiene articles can be selected from joss sticks, insecticides, repellents, propellants, rust removers, perfumed freshening wipes, armpit pads, baby diapers, sanitary towels, toilet paper, cosmetic wipes, pocket tissues, dishwasher and deodorizer.

Cleaning compositions, such as e.g. cleaners for solid surfaces, can be selected from perfumed acidic, alkaline and neutral cleaners, such as e.g. floor cleaners, window cleaners, dishwashing compositions both for handwashing and machine washing use, bath and sanitary cleaners, scouring milk, solid and liquid toilet cleaners, powder and foam carpet cleaners, waxes and polishes such as furniture polishes, floor waxes, shoe creams, disinfectants, surface disinfectants and sanitary cleaners, brake cleaners, pipe cleaners, limescale removers, grill and oven cleaners, algae and moss removers, mold removers, facade cleaners.

Textile detergent compositions can be selected from liquid detergents, powder detergents, laundry pretreatments such as bleaches, soaking agents and stain removers, fabric softeners, washing soaps, washing tablets.

Food means a raw, cooked, or processed edible substance, ice, beverage or ingredient used or intended for use in whole or in part for human consumption, or chewing gum, gummies, jellies, and confectionaries.

A food supplement is a product intended for ingestion that contains a dietary ingredient intended to add further nutritional value to the diet. A dietary ingredient may be one, or any combination, of the following substances: a vitamin, a mineral, an herb or other botanical, an amino acid, a dietary substance for use by people to supplement the diet by increasing the total dietary intake, a concentrate, metabolite, constituent, or extract. Food supplements may be found in many forms such as tablets, capsules, softgels, gelcaps, liquids, or powders.

Pharmaceutical compositions comprise compositions which are intended for use in the diagnosis, cure, mitigation, treatment, or prevention of disease as well as articles (other than food) intended to affect the structure or any function of the body of man or other animals.

Crop protection compositions comprise compositions which are intended for the managing of plant diseases, weeds and other pests (both vertebrate and invertebrate) that damage agricultural crops and forestry.

The compositions according to the invention can further comprise one or more substances, such as, for example: preservatives, abrasives, anti-acne agents, agents to combat skin aging, antibacterial agents, anti-cellulite agents, antidandruff agents, anti-inflammatory agents, irritation-preventing agents, irritation-alleviating agents, antimicrobial agents, antioxidants, astringents, sweat-inhibiting agents, antiseptics, anti-statics, binders, buffers, carrier materials, chelating agents, cell stimulants, cleaning agents, care agents, hair removal agents, surface-active substances, deodorizing agents, antiperspirants, emulsifiers, enzymes, essential oils, fibers, film formers, fixatives, foam formers, foam stabilizers, substances for preventing foaming, foam boosters, fungicides, gelling agents, gel-forming agents, hair care agents, hair shaping agents, hair smoothing agents, moisture-donating agents, moisturizing substances, humectant substances, bleaching agents, strengthening agents, stain removal agents, optical brighteners, impregnating agents, soil repellents, friction-reducing agents, lubricants, moisturizing creams, ointments, opacifiers, plasticizers, covering agents, polish, shine agents, polymers, powders, proteins, refatting agents, exfoliating agents, silicones, skin-calming agents, skin-cleansing agents, skin care agents, skin-healing agents, skin lightening agents, skin-protective agents, skin-softening agents, cooling agents, skin-cooling agents, warming agents, skin-warming agents, stabilizers, UV-absorbent agents, UV filters, fabric softeners, suspending agents, skin-tanning agents, thickeners, vitamins, waxes, fats, phospholipids, saturated fatty acids, mono- or polyunsaturated fatty acids, α-hydroxy acids, polyhydroxy fatty acids, liquefiers, dyes, color-protection agents, pigments, anti-corrosives, polyols, electrolytes, or silicone derivatives.

The compounds (I), their stereoisomers, mixtures of stereoisomers thereof, mixtures of different compounds (I) or mixtures of at least one compound of the formula (I) with one or both of the compounds of the formula (II.1) and/or (II.2) may be worked into in compositions simply by directly mixing them with the basic composition lacking only this/these compound(s). Alternatively, the one or more compounds (I), their one or more stereoisomers, mixtures of stereoisomers thereof, mixtures of different compounds (I) or mixtures of at least one compound of the formula (I) with one or both of the compounds of the formula (II.1) and/or (II.2) may be mixed simultaneously or consecutively with the other components of the composition or with pre-formed mixtures of a part of the other components.

The compounds (I), their stereoisomers, mixtures of stereoisomers thereof, mixtures of different compounds (I) or mixtures of at least one compound of the formula (I) with one or both of the compounds of the formula (II.1) and/or (II.2) may, in an earlier step, be entrapped with an entrapment material, for example, polymers, capsules, microcapsules and nanocapsules, liposomes, film formers, absorbents such as carbon or zeolites, cyclic oligosaccharides and mixtures thereof, or may be chemically bonded to substrates, which are adapted to release the compounds (I) or their stereoisomers upon application of an external stimulus such as light, enzyme, or the like, and then mixed with the composition.

The compounds (I), their stereoisomers, mixtures of stereoisomers thereof, mixtures of different compounds (I) or mixtures of at least one compound of the formula (I) with one or both of the compounds of the formula (II.1) and/or (II.2) and compositions comprising these compounds according to the present invention can also be in microencapsulated form, spray-dried form, in the form of inclusion complexes or in the form of extrusion products. The properties can be further optimized by so-called "coating" with suitable materials with regard to a more targeted release of the scent, for which purpose preferably waxy synthetic substances such as e.g. polyvinyl alcohol are used.

The microencapsulation can take place for example by the so-called coacervation method with the help of capsule materials, e.g. made of polyurethane-like substances or soft gelatin. The spray-dried perfume oils can be produced for example by spray-drying an emulsion or dispersion comprising a compound of formula (I), a stereoisomer thereof, a mixture of stereoisomers thereof, a mixture of different compounds (I) or a mixture of at least one compound of the formula (I) with one or both of the compounds of the formula (II.1) and/or (II.2), or a composition of the present invention described herein, wherein carrier substances that can be used are modified starches, proteins, dextrin and vegetable gums. Inclusion complexes can be prepared e.g. by introducing dispersions of fragrance compositions and cyclodextrins or urea derivatives into a suitable solvent, e.g. water. Extrusion products can be produced by melting a compound of formula (I), a stereoisomer thereof, a mixture of stereoisomers thereof or a mixture of different compounds (I), or a composition of the present invention described herein with a suitable wax-like substance and by extrusion with subsequent solidification, optionally in a suitable solvent, e.g. isopropanol.

Generally, the total amount of the compounds of formula (I) or their stereoisomers in the compositions according to the present invention is typically adapted to the particular intended use or the intended application and can, thus, vary over a wide range. As a rule, the customary standard commercial amounts for scents are used.

The compositions according to the invention can comprise the compounds of formula (I) or their stereoisomers in an overall amount of from 0.001 to 99.9% by weight, preferably from 0.01 to 90% by weight, more preferably from 0.05 to 80%, in particular from 0.1 to 60% by weight, more particularly from 0.1 to 40% by weight, e.g. from 0.1 to 10% by weight or 0.1 to 15% by weight, based on the total weight of the composition.

In one embodiment of the invention, the compositions comprise the compounds of formula (I) or their stereoisomers in an overall amount of from 0.001 to 5 weight %, preferably from 0.01 to 2 weight % based on the total weight of the composition.

The following examples serve as further illustration of the invention.

EXAMPLES

1. Preparation Examples

| Abbreviations: | |
|---|---|
| HPA | hydroxypivalinaldehyde |
| DMAP: | 4-(dimethylamino)-pyridine |
| EA: | ethyl acetate |
| THF: | tetra hydrofuran |
| MTBE: | methyl-tert-butyl ether |
| RT: | room temperature |

Analytics:

The purity of the products was determined by gas chromatography area-%:

GC-Column: HP5 FD (30 m (Length), 0.25 mm (ID), 0.32 micrometer (film)).

Temperature program: 5 min at 50° C., from 50° C. to 250° C. at 6°/min, 6 min at 250° C.

Injector: 250° C., detector: 280° C.

For all samples except for propionate samples whose purity was determined by gas chromatography area-%:

GC-Column: DB-1701 (30 m (Length), 0.32 mm (ID), 0.25 micrometer (film)).

Temperature program: 5 min at 70° C., from 70° C. to 240° C. at 5°/min, 5 min at 240° C.

Injector: 250° C., detector: 280° C.

The products were identified by $^{13}$C NMR.

Example 1: Synthesis of 2-methyl-2-(4-methyl-enetetrahydropyran-2-yl)propan-1-ol and its Double Bond Isomers (Using Toluenesulfonic Acid Monohydrate as Catalyst)

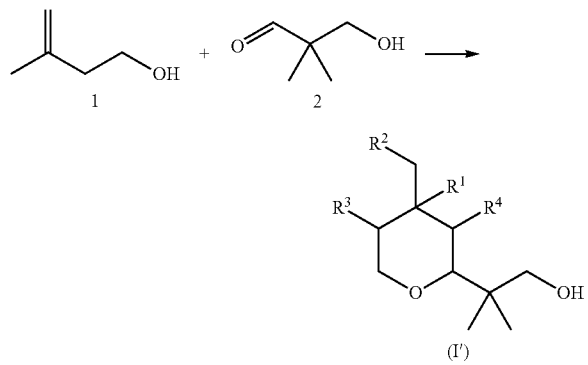

| Compound | MW | Mass/Volume | Moles |
|---|---|---|---|
| HPA (23.60% in toluene) | 102.1 | 500 g | 1.155 |
| Isoprenol | 86.13 | 119.4 g | 1.386 |
| Toluenesulfonic acid monohydrate | 190.22 | 2.2 g | 0.01155 |

A mixture of isoprenol 1 (119.4 g, 1.386 mol) and a 23.6% HPA 2 solution in toluene (500 g, 1.150 mol) was stirred at 40° C. At this temperature, toluenesulfonic acid monohydrate (2.2 g, 0.01155 mol) was added to the reaction mixture. The mixture was stirred at reflux (98-113° C.) for 7 h while water was being distilled during the reaction (23.3 g). After this time, the reaction mixture was set to RT and stirred for 17 h. To the mixture 150 mL of water were then added and the organic phase was washed twice with a 5% solution of NaHCO$_3$ and with water. The organic extracts were combined and dried with sodium sulfate and the solvent was removed under reduced pressure. The crude product was subjected to a distillative separation resulting in a major fraction that proved to be a mixture of the three elimination products I'-1, I'-2 and I'-3 with a purity of 94% (GC area %). The NMR analysis revealed 40% of isomer I'-1, 25% of isomer I'-2 and 35% of isomer I'-3.

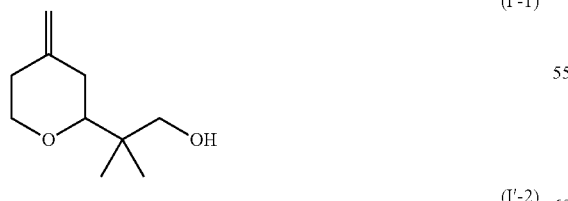
(I'-1)

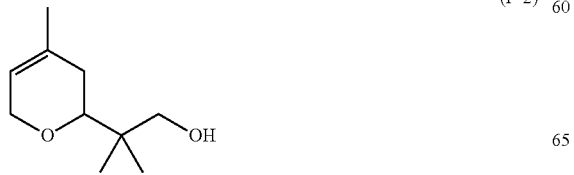
(I'-2)

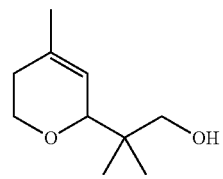
(I'-3)

I'-1 Isomer:

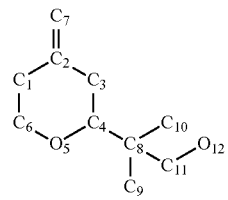

I'-1 Isomer: $^{13}$C NMR (125 MHz, CDCl$_3$): δ=19.12 (C9), 22.28 (C10), 35.11 (C1), 35.40 (C3), 38.09 (C8), 69.15 (C6), 71.92 (C11), 86.72 (C4), 108.96 (C7), 144.38 (C2).

I'-2 Isomer:

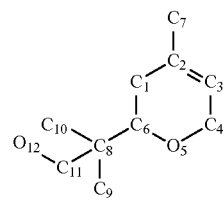

I'-2 Isomer: $^{13}$C NMR (125 MHz, CDCl$_3$): δ=18.81 (C9), 21.87 (C10), 23.04 (C7), 30.07 (C1), 37.66 (C8), 66.26 (C4), 71.60 (C11), 81.13 (C6), 119.08 (C3), 131.73 (C2).

I'-3 Isomer:

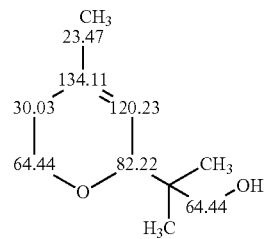

I'-3 Isomer: $^{13}$C NMR (125 MHz, CDCl$_3$): δ=19.42, 22.16, 23.47, 30.03, 64.44, 82.22, 120.23, 134.11.

Example 2: Synthesis of 2-methyl-2-(4-methyl-enetetrahydropyran-2-yl)propan-1-ol and its Double Bond Isomers (Using Methanesulfonic Acid as Catalyst)

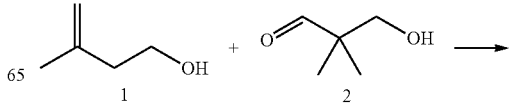

-continued

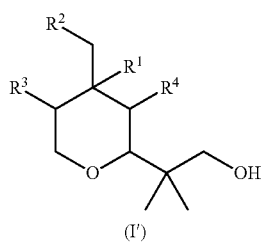

| Compound | MW | Mass/Volume | Moles |
|---|---|---|---|
| HPA (16.8% in toluene) | 102.1 | 150 g | 0.246 |
| Isoprenol | 86.13 | 25.41 g | 0.295 |
| Methanesulfonic acid | 96.1 | drops | |

A mixture of isoprenol 1 (25.41 g, 0.295 mol) and a 16.8% HPA 2 solution in toluene (150 g, 0.246 mol) was stirred at 20° C. At this temperature, 2 drops of pure methanesulfonic acid were added to the reaction mixture. The mixture was stirred at reflux (113° C.) for 5 h while water was being distilled during the reaction. After this time 5 drops of methanesulfonic acid were added and the reaction was stirred for 4 h at reflux. After 9 h, approximately 5 mL of water had been distilled. Afterwards, the reaction mixture was set to RT. To the mixture 150 mL of water were added and the organic phase was washed with a 5% solution of NaHCO₃ and with water. The organic extracts were combined and dried with sodium sulfate, and the solvent was removed at reduced pressure. The crude product was subjected to a distillative separation resulting in a major fraction that proved to be a mixture of the three elimination products I'-1, I'-2 and I'-3 with a purity of 92% (GC area %). The NMR analysis revealed 70% of isomer I'-1, and 15% of each of the isomers I'-2 and I'-3.

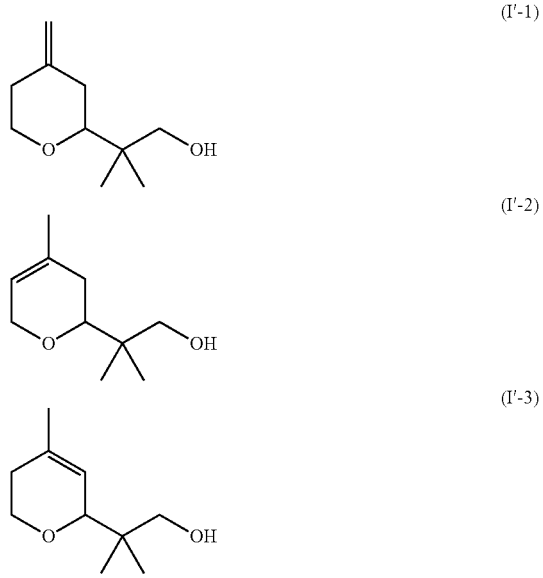

Example 3: Synthesis of 2-methyl-2-(4-methyl-enetetrahydropyran-2-yl)propan-1-ol and its Double Bond Isomers (Using Methanesulfonic Acid as Catalyst)

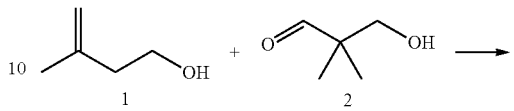

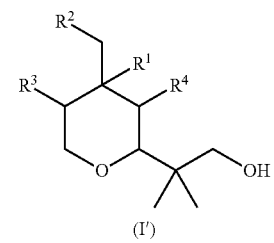

| Compound | MW | Mass/Volume | Moles |
|---|---|---|---|
| HPA (23.6% in toluene) | 102.1 | 750 g | 0.71 |
| Isoprenol | 86.13 | 72.60 g | 0.853 |
| Methanesulfonic acid | 96.1 | drops | |

A mixture of isoprenol 1 (72.60 g, 0.853 mol) and a 23.6% HPA 2 solution in toluene (750 g, 0.71 mol) was stirred at 40° C. At this temperature, 10 drops of methanesulfonic acid were added to the reaction mixture. The mixture was stirred at reflux (113° C.) for 4 h while water was being distilled during the reaction. After this time 10 drops of methane-sulfonic acid were added and the reaction was stirred for 2.5 h at reflux, then another 20 drops of methanesulfonic acid were added. At this point, water started to distill. The reaction was left at this temperature for 9 more hours. After this time, the reaction mixture was set to RT. To the mixture 300 mL of water were added and the organic phase was washed with a 5% solution of NaHCO₃ and with water. The organic extracts were combined and dried with sodium sulfate and the solvent was removed under reduced pressure. The crude product was subjected to a distillative separation and two major fractions were collected.

According to NMR, one of the fractions (fraction 1) proved to be a mixture of two of the elimination products I'-1 (55%) and I'-3 (20%) and the two acetals II'.1 (15%) and II'.2 (5%). This fraction was used to prepare the propionate in example 8.

Also according to NMR, the other fraction (fraction 2) proved to be a mixture of the three elimination products I'-1 (30%), I'-2 (35%) and I'-3 (15%) and the acetal II'.1 (5%).

This fraction was used to prepare the methyl ether in example 10.

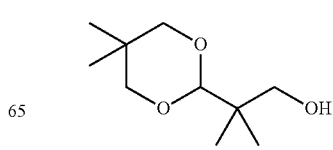

-continued

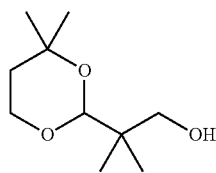
(II'.2)

II'.1-Isomer: $^{13}$C NMR (125 MHz, CDCl$_3$): δ=19.93, 21.68, 22.82, 30.25, 38.95, 69.17, 77.14, 107.57.

II'.2-Isomer: $^{13}$C NMR (125 MHz, CDCl$_3$): δ=19.82, 20.39, 21.44, 31.69, 35.89, 38.68, 63.16, 69.49, 71.67, 101.41.

Example 4: Synthesis of 2-methyl-2-(4-methyl-enetetrahydropyran-2-yl)propan-1-ol and its Double Bond Isomers (Using Methansulfonic Acid as Catalyst)

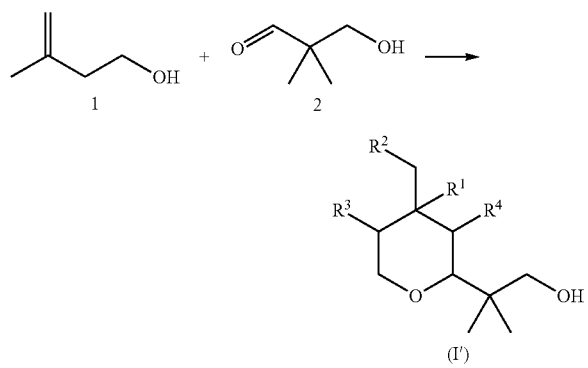

| Compound | MW | Mass/Volume | Moles |
|---|---|---|---|
| HPA (23.6% in toluene) | 102.1 | 250 g | 0.578 |
| Isoprenol | 86.13 | 59.7 g | 0.693 |
| Methanesulfonic acid | 96.1 | drops | |

A mixture of isoprenol 1 (59.7 g, 0.693 mol) and a 23.6% HPA 2 solution in toluene (250 g, 0.578 mol) was stirred at 40° C. At this temperature, 13 drops of pure methanesulfonic acid were added to the reaction mixture. The mixture was stirred at reflux (113° C.) for 7 h while water was being distilled during the reaction (10.8 mL). After this time, the reaction mixture was set to RT and stirred for 17 h. To the mixture 100 mL of water were added and the organic phase was washed with a 5% solution of NaHCO$_3$ and with water. The organic extracts were combined and dried with sodium sulfate and the solvent was removed under reduced pressure. The crude product was subjected to a distillative separation resulting in a major fraction that proved to be a mixture of the three elimination products I'-1, I'-2 and I'-3 with a purity of 91% (GC area %). The NMR analysis revealed 54% of isomer I'-1, 19% of isomer I'-2 and 18% of isomer I'-3.

Example 5: Synthesis of 2-methyl-2-(4-methyl-enetetrahydropyran-2-yl)propan-1-ol and its Double Bond Isomers (Using Methansulfonic Acid as Catalyst)

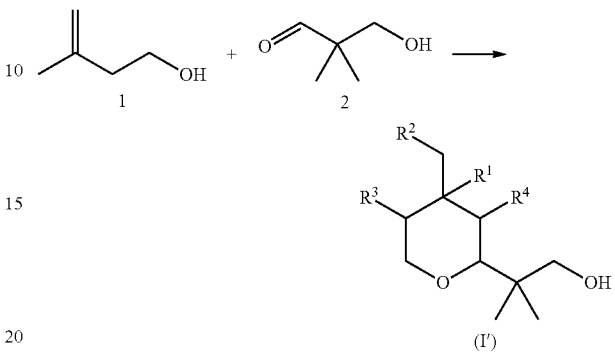

The protocol from example 4 was repeated. After the reaction the crude product was subjected to a distillative separation resulting in a major fraction that proved to be a mixture of the three elimination products I'-1, I'-2 and I'-3 with a purity of 90% (GC area %). The GC analysis revealed 46% of isomer I'-1, 27% of isomer I'-2 and 17% of isomer I'-3.

Example 6: Synthesis of [2-methyl-2-(4-methyl-enetetrahydropyran-2-yl)propyl] acetate and its Double Bond Isomers

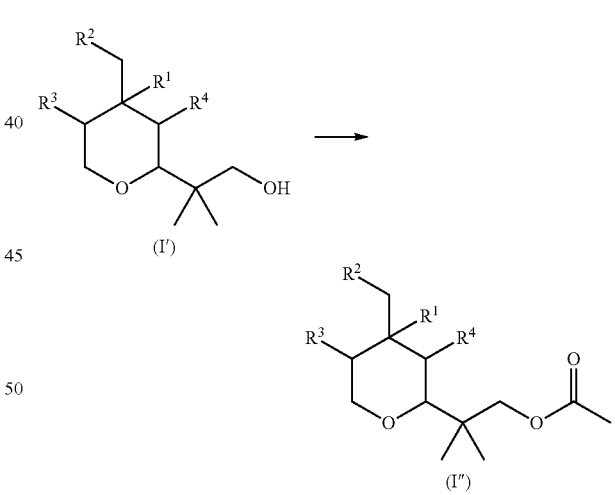

| Compound | MW | Mass/Volume | Moles |
|---|---|---|---|
| I'-1, I'-2, I'-3 mixture from example 2 | 170.25 | 9 g | 0.053 |
| Acetic anhydride | 102.09 | 6.5 g | 0.063 |
| DMAP | 122.17 | 0.19 | 0.002 |
| THF | | 50 mL | |

DMAP (0.19 g, 0,002 mol) was added to a solution of the product of example 2 (9 g, 0.053 mol) in 50 mL of THF at RT. The obtained mixture was refluxed at 53° C. while acetic anhydride (6.5 g, 1.2 eq.) was slowly added at this temperature. After 1 h, full conversion was observed by GC. The reaction was cooled down to RT and slowly quenched with 50 mL of water. Afterwards 50 mL of EA were added. The organic phase was separated and washed with a saturated aqueous solution of NaHCO₃ and then with brine. The organic extracts were combined and dried with sodium sulfate. After evaporating the solvent at reduced pressure 9.6 g of a crude product was obtained containing about 90% of the title compound, as per GC analysis (area %). Purification by distillation afforded the title compound having a purity of 92% (GC area %). %). The NMR analysis revealed a 70% of isomer I"-1, and a 15% of each of the isomers I"-2 and I"-3.

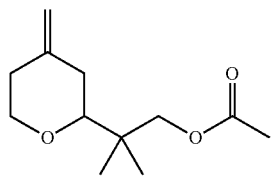
(I"-1)

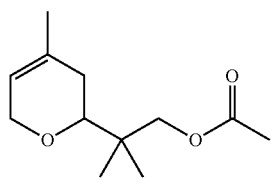
(I"-2)

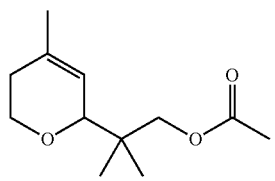
(I"-3)

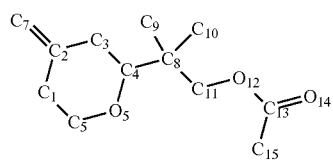

I"-1 Isomer: $^{13}$C NMR (125 MHz, CDCl₃): δ=19.59 (C9), 20.96 (C10), 21.23 (C15), 35.01 (C1), 35.24 (C3), 37.54 (C8), 69.01 (C6), 70.26 (C11), 82.38 (C4), 108.61 (C7), 145.14 (C2), 171.18 (C13).

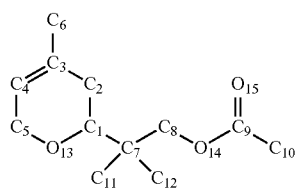

I"-2 Isomer: $^{13}$C NMR (125 MHz, CDCl₃): δ=19.34 (C12), 20.90 (C11), 20.97 (C10), 23.19 (C6), 29.87 (C2), 37.26 (C7), 66.53 (C5), 70.31 (C8), 77.22 (C1), 119.87 (C4), 132.01 (C3), 171.20 (C9).

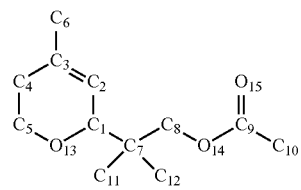

I"-3 Isomer: $^{13}$C NMR (125 MHz, CDCl₃): δ=19.98 (C12), 20.99 (C11), 21.33 (C10), 23.55 (C6), 30.07 (C4), 38.06 (C7), 64.20 (C5), 70.13 (C8), 78.13 (C1), 119.83 (C2), 134.31 (C3), 171.25 (C9).

Example 7: Synthesis of [2-methyl-2-(4-methyl-enetetrahydropyran-2-yl)propyl] acetate and its Double Bond Isomers

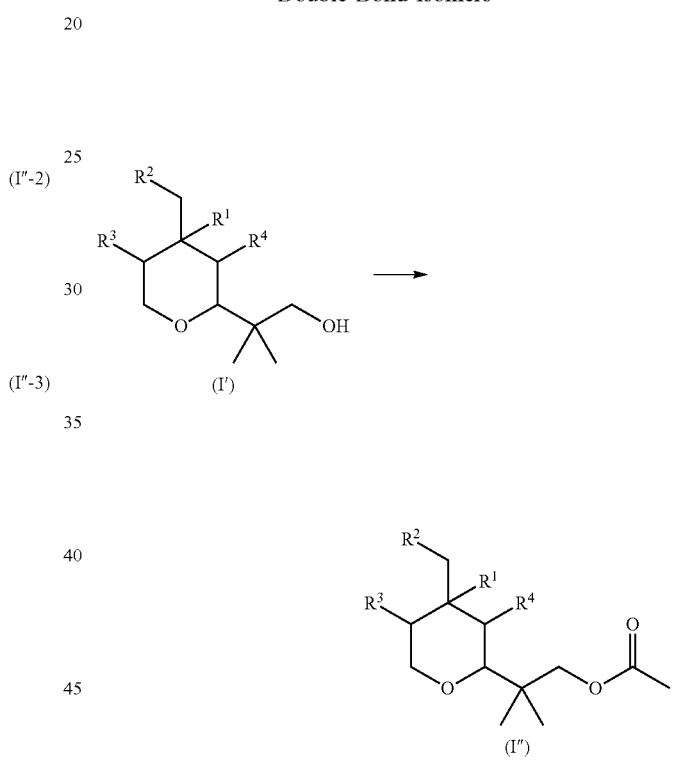

| Compound | MW | Mass/Volume | Moles |
| --- | --- | --- | --- |
| I'-1, I'-2, I'-3 mixture from example 1 | 170.25 | 75 g | 0.441 |
| Acetic anhydride | 102.09 | 53.9 g | 0.529 |
| DMAP | 122.17 | 1.6 g | 0.013 |
| THF | | 300 mL | |

The sample was prepared following the protocol described in Example 5. Purification by distillation afforded the title compound having a purity>95% (GC area %). The GC analysis revealed a 44% of isomer I"-1, a 18% isomer I"-2 and 33% of isomer I"-3.

Example 8: Synthesis of [2-methyl-2-(4-methyl-enetetrahydropyran-2-yl)propyl] propanoate, its Double Bond Isomer and Corresponding Acetals

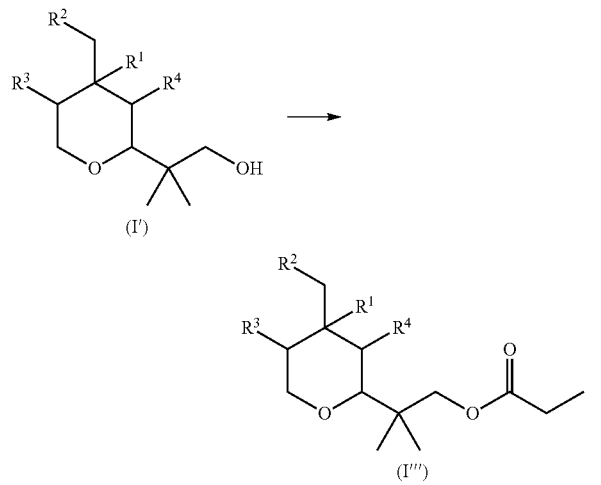

| Compound | MW | Mass/Volume | Moles |
|---|---|---|---|
| I'-1, I'-3, II'.1 and II'.2 mixture from ex. 3, fraction 1 | 170.25 | 15 g | 0.088 |
| Propionic anhydride | 130.14 | 14.9 g | 0.115 |
| DMAP | 122.17 | 0.32 | 0.003 |
| THF | | 70 mL | |

DMAP (0.32 g, 0.003 mol) was added to a solution of compounds I'-1, I'-3, II'.1 and II'.2 from Example 3, fraction 1 (15 g, 0.088 mol) in 70 mL of THE at RT. The obtained mixture was refluxed at 53° C. while propionic anhydride (14.9 g, 1.3 eq.) was slowly added at this temperature. After 1 h, full conversion was observed by GC. The reaction was cooled down to RT and slowly quenched with 50 mL of water. Afterwards 50 mL of EA were added. The organic phase was separated and washed with a saturated aqueous solution of $NaHCO_3$ and then with brine. The organic extracts were combined and dried with sodium sulfate. After evaporating the solvent at reduced pressure 20.9 g of a crude product was obtained containing about 80% of the title compound, as per GC analysis (area %). Purification by distillation afforded the title compound having a purity of 96% (GC area %). %). The NMR analysis revealed a 50% of isomer I'''-1, a 20% of I'''-3, a 20% of II'''.1 and 5% of II'''.2.

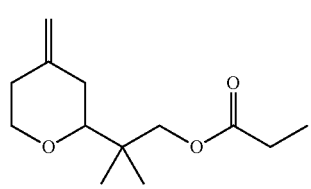
(I'''-1)

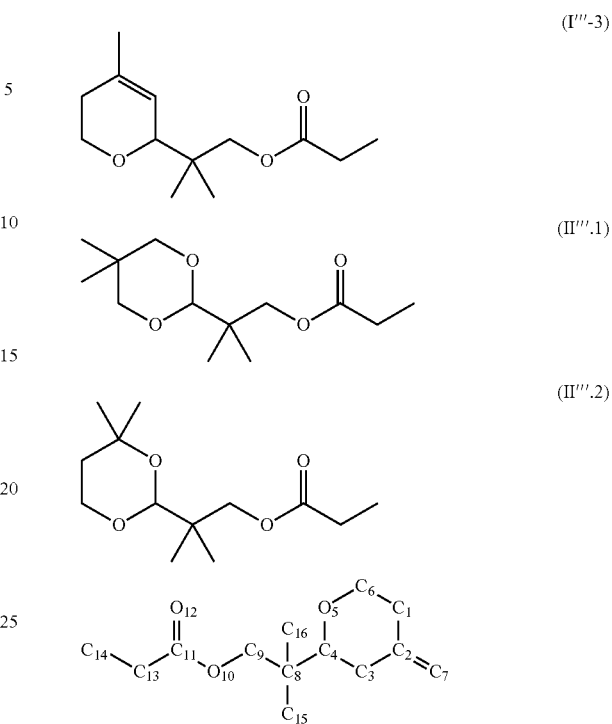

I'''-1 Isomer: $^{13}C$ NMR (125 MHz, $CDCl_3$): δ=9.27 (C14), 19.70 (C15), 21.22 (C16), 27.70 (C13), 35.25 (C1), 35.04 (C3), 37.63 (C8), 69.03 (C6), 70.06 (C9), 82.46 (C4), 108.59 (C7), 145.16 (C2), 174.45 (C11).

I'''-3 Isomer: $^{13}C$ NMR (125 MHz, $CDCl_3$): δ=9.27 (C14), 19.70 (C15), 21.22 (C16), 23.54 (C7), 27.70 (C13), 30.08 (C1), 37.63 (C8), 64.20 (C6), 69.38 (C9), 78.18 (C4), 119.89 (C3), 134.26 (C2), 174.38 (C11).

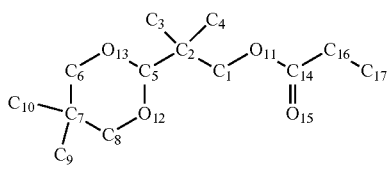

II'''.1: $^{13}C$ NMR (125 MHz, $CDCl_3$): δ=9.24 (C17), 19.46 (C4), 21.32 (C3), 21.71 (C10), 22.85 (C9), 27.67 (C16), 30.19 (C7), 38.46 (C2), 69.38 (C1), 77.21 (C6, C8), 104.36 (C5), 174.48 (C14).

II'''.2: $^{13}C$ NMR (126 MHz, $CDCl_3$) δ=174.45, 97.75, 70.97, 69.55, 63.16, 38.31, 35.88, 31.64, 27.70, 21.43, 19.84, 19.10, 9.27.

Example 9: Synthesis of [2-methyl-2-(4-methyl-enetetrahydropyran-2-yl)propyl] propanoate and its Double Bond Isomers

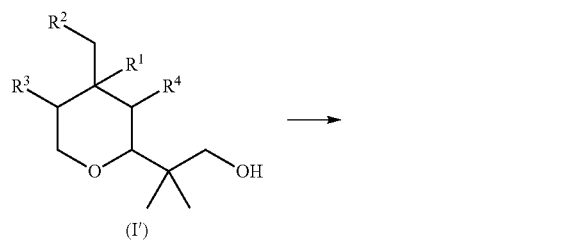

(I')

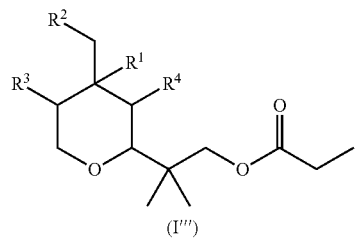

(I''')

| Compound | MW | Mass/Volume | Moles |
|---|---|---|---|
| I'-1, I'-2 and I'-3 from example 4 | 170.25 | 15 g | 0.088 |
| Propionic anhydride | 130.14 | 14.9 g | 0.115 |
| DMAP | 122.17 | 0.32 | 0.003 |
| THF | | 70 mL | |

The sample was prepared following the protocol described in Example 7. Purification by distillation afforded the title compound having a purity>94% (GC area %). The GC analysis revealed a 52% of isomer I'''-1, a 23% isomer I'''-2 and 19% of isomer I'''-3.

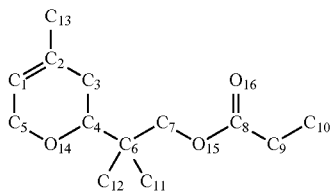

Isomer I'''-2: $^{13}$C NMR (126 MHz, CDCl$_3$) δ=174.51, 132.06, 119.91, 77.29, 70.12, 66.56, 37.35, 29.91, 27.71, 23.20, 20.92, 19.40, 9.27.

Example 10: Synthesis of 2-(2-methoxy-1,1-dimethyl-ethyl)-4-methylene tetrahydropyran and its Double Bond Isomers

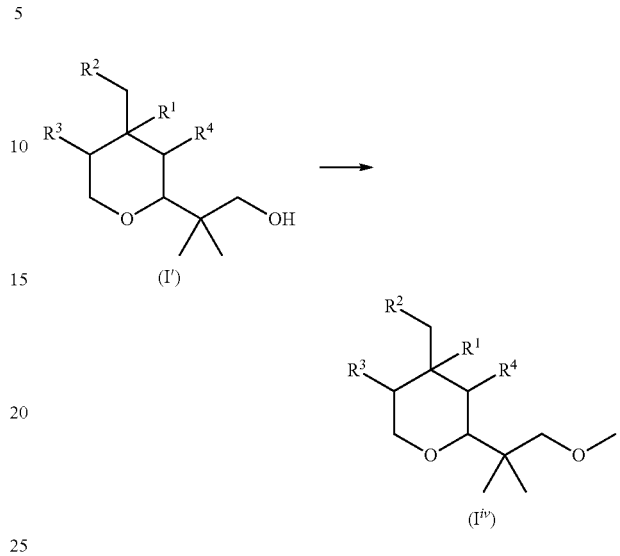

(I')

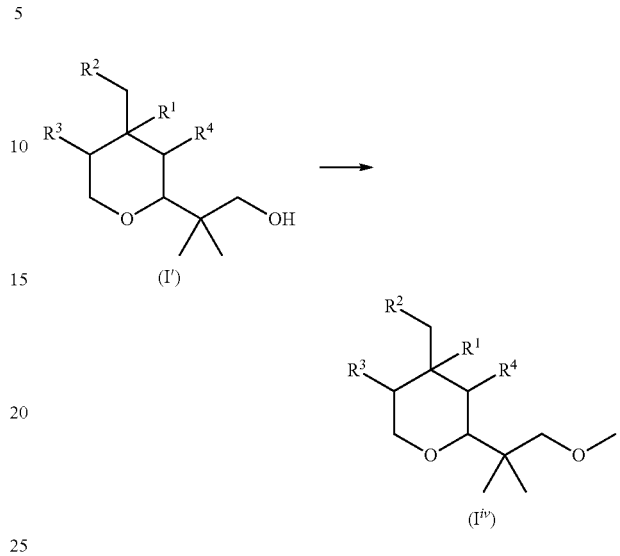

(I$^{iv}$)

| Compound | MW | Mass/Volume | Moles |
|---|---|---|---|
| I'-1, I'-2, I'-3 mixture from ex. 3, fraction 2 | 170.25 | 8 g | 0.047 |
| Methyl iodide | 141.94 | 8.7 g | 0.061 |
| NaH | 23.99 | 2.4 g | 0.061 |
| THF | | 105 mL | |

To a dispersion of sodium hydride (1.3 eq) in 75 mL of THF a solution of 8 g of compounds I'-1, I'-2 and I'-3 from Example 3, fraction 2 in 30 mL of THF was slowly added at 0° C. The mixture was stirred for 30 min at 0° C. Then 1.3 eq of methyl iodide were slowly added at RT. After the addition, the mixture was stirred at 40° C. for 4 h. The reaction mixture was cooled to 0° C. and the addition of 0.25 eq of NaH followed by 0.25 eq of methyl iodide was repeated. The mixture was then stirred for 18 h at 40° C. The reaction was slowly quenched with 50 mL of water. The organic phase was extracted with 3 times 50 mL of MTBE. The organic extracts were combined and washed with 50 mL of NH$_3$ solution and with 50 mL of brine. The organic extracts were combined and dried with sodium sulfate. After evaporating the solvent at reduced pressure 8.4 g of crude product were obtained containing 91% of the desired methyl ether according to the GC (area %). The crude product was subjected to a distillative separation resulting in a major fraction that proved to be the title compound with a purity of 95% (GC area %). NMR analysis indicated a 35% of isomer I$^{iv}$-1, a 45% of I$^{iv}$-2 and a 20% of I$^{iv}$-3.

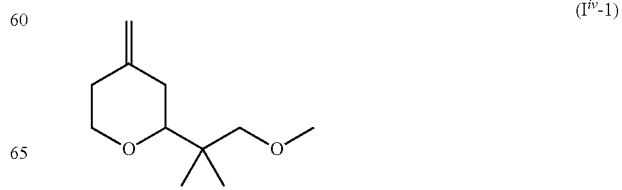

(I$^{iv}$-1)

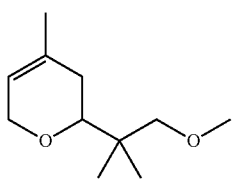
(I$^{iv}$-2)

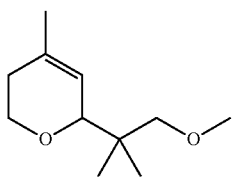
(I$^{iv}$-3)

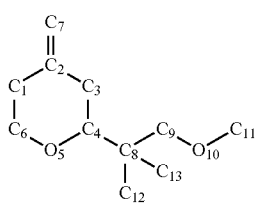

I$^{iv}$-1 Isomer: $^{13}$C NMR (125 MHz, CDCl$_3$): δ=20.13 (C13), 20.88 (C12), 35.12 (C1), 35.38 (C3), 37.94 (C8), 59.30 (C11), 69.00 (C6), 79.54 (C9), 82.71 (C4), 108.34 (C7), 145.47 (C2).

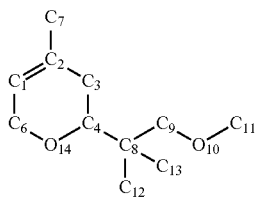

I$^{iv}$-2 Isomer: $^{13}$C NMR (125 MHz, CDCl$_3$): δ=19.69 (C13), 20.22 (C12), 23.53 (C7), 30.18 (C3), 38.29 (C8), 59.37 (C11), 66.57 (C6), 78.32 (C4), 79.56 (C9), 119.79 (C1), 132.33 (C2).

I$^{iv}$-3 isomer: $^{13}$C NMR (125 MHz, CDCl$_3$): δ=20.22, 21.32, 23.53, 30.18, 38.78, 59.38, 64.37, 78.33, 79.55, 120.55, 133.71.

Example 11: Synthesis of 2-(2-ethoxy-1,1-dimethyl-ethyl)-4-methyl ene-tetrahydropyran and its Double Bond Isomer(s)

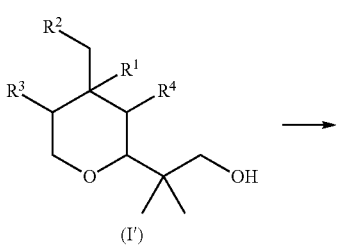

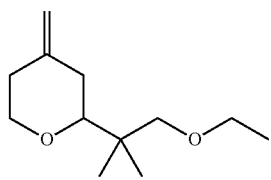
(I')

| Compound | MW | Mass/Volume | Moles |
|---|---|---|---|
| I'-1, I'-2, I'-3 mixture from example 5 | 170.25 | 10 g | 0.059 |
| Ethyl iodide | 155.97 | 11.9 g | 0.076 |
| NaH | 23.99 | 3 g | 0.076 |
| THF | | 105 mL | |

To a dispersion of sodium hydride (1.3 eq) in 75 mL of THF a solution of 10 g of compounds I'-1, I'-2 and I'-3 (46:27:17) from example 5 in 30 mL of THF was slowly added at 0° C. The mixture was stirred for 30 min at 0° C. Then 1.3 eq of ethyl iodide were slowly added at RT. After the addition, the mixture was stirred at 50° C. for 4 h. The reaction mixture was cooled to 0° C. and the addition of 0.25 eq of NaH followed by 0.25 eq of ethyl iodide was repeated. The mixture was then stirred for 18 h at 50° C. The reaction mixture was cooled to 0° C. and the addition of 0.25 eq of NaH followed by 0.25 eq of ethyl iodide was repeated again. The mixture was then stirred for 6 h at 50° C. The reaction was slowly quenched with 50 mL of water. The organic phase was extracted with 3 times 50 mL of MTBE. The organic extracts were combined and washed with 50 mL of NH$_3$ solution and with 50 mL of brine. The organic extracts were combined and dried with sodium sulfate. After evaporating the solvent at reduced pressure, 10.1 g of crude product were obtained containing 91% of the desired ethyl ether according to the GC (area %). The crude product was subjected to a distillative separation resulting in a major fraction that proved to be the title compound with a purity of 94% (GC area %). NMR analysis indicated a 50% of isomer $^v$-1, a 30% of I-2 and a 20% of I-3.

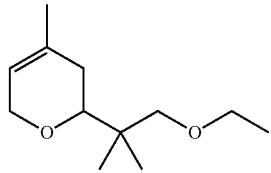
(I'-1)

(I'-2)

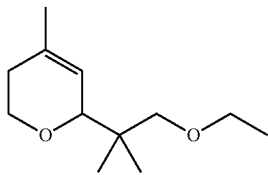

(I'-3)

I'-1 Isomer: $^{13}$C NMR (125 MHz, CDCl$_3$): δ=15.1, 20.24, 21.32, 35.14, 35.41, 38.28, 66.71, 68.99, 76.99, 82.70, 108.25, 145.66

I'-2 Isomer: $^{13}$C NMR (125 MHz, CDCl$_3$): δ=15.1, 20.03, 21.00, 23.25, 29.99, 37.94, 66.56, 66.73, 76.99, 77.49, 119.81, 132.45

I'-3 isomer: $^{13}$C NMR (125 MHz, CDCl$_3$): δ=15.1, 20.33, 21.32, 23.54, 30.20, 38.82, 64.27, 66.79, 76.99, 78.41, 120.73, 133.50.

Example 12: Synthesis of (2,2-dimethyl-3-oxo-propyl) acetate

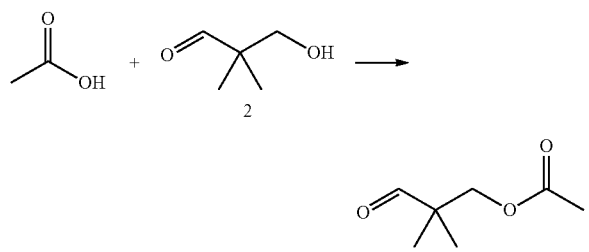

| Compound | MW | Mass/Volume | Moles |
|---|---|---|---|
| Hydroxypivalinaldehyde (87 wt %, water content ~7 wt %) | 102.13 | 225 g | 1.917 |
| Acetic acid | 60.05 | 900 mL | 15.736 |
| p-Toluenesulfonic acid monohydrate | 190.22 | 10.94 g | 0.057 |
| Cyclohexane | | 663 mL | | p-Toluenesulfonic acid monohydrate (10.94 g, 0.057 mol) was added to a solution of hydroxypivalinaldehyde (225 g, 1,917 mol) and acetic acid (900 mL, 15.736 mol) in 663 mL of cyclohexane at RT. The obtained mixture was refluxed at 72-75° C. and water was removed via a dean-stark apparatus over 5 h. After water removal, a distillation was performed until an inner temperature of 133° C. The crude residue was subjected to fractionated distillation to prepare a sample of (2,2-dimethyl-3-oxo-propyl) acetate in a purity of >99 GC-area % as colorless liquid for olfactory testing.

NMR Analysis:

$^{13}$C NMR (126 MHz, CDCl$_3$) δ=203.64, 170.95-170.93, 67.92, 46.26, 20.70, 18.84, 18.84.

$^1$H NMR (500 MHz, Chloroform-d) δ=9.53 (s, 1H), 4.12 (s, 2H), 2.05 (s, 3H), 1.12 (s, 6H).

Example 13: Synthesis of [2-methyl-2-(4-methylenetetrahydropyran-2-yl)propyl] acetate and its Double Bond Isomers

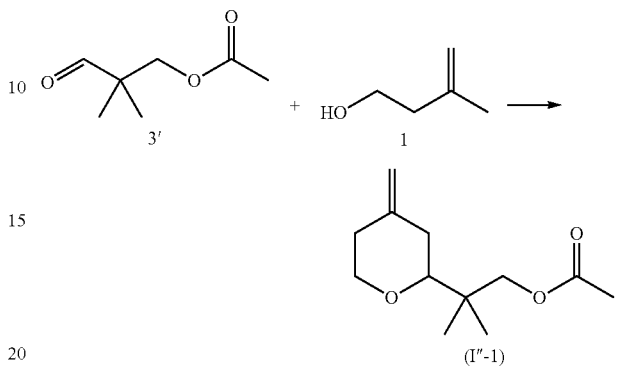

| Compound | MW | Mass/Volume | Moles |
|---|---|---|---|
| HPA-acetate from example 12, 95 GC-a % | 144.17 | 15 g | 0.099 |
| 3-Methyl-3-buten-1-ol | 86.13 | 10.75 g | 0.125 |
| Bortrifluoride-diethylether | 141.93 | 2.953 g | 0.0208 |
| Toluene | | 165 mL | |

BF$_3$-etherate (2.953 g, 0.0208 mol) was added to a solution of HPA-acetate (15 g, 0.099 mol) from example 12 and 3-methyl-3-buten-1-ol (10.75 g, 0.125 mol) in 165 mL of toluene at RT. The obtained mixture was stirred at 70° C. After 7 h, the reaction mixture was brought to RT and washed with 100 mL of a saturated aqueous solution of NaHCO$_3$. The phases were separated and the organic phase was dried with sodium sulfate. After filtration and evaporation of the solvent at 60° C. and 150-15 mbar, the crude product was purified by distillation to afford the title compound with a purity of 97.8% (GC area %) for olfactory testing.

The NMR/GC analysis revealed a 2% GC-area of isomer I"-1, a 66% GC-area of the isomer I"-2 and 30% GC-area of the isomer I"-3.

Example 14: Synthesis of (2,2-dimethyl-3-oxo-propyl) propionate

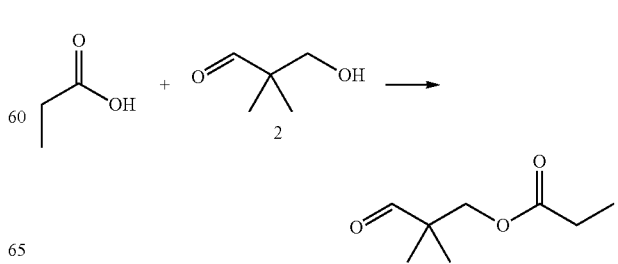

| Compound | MW | Mass/Volume | Moles |
|---|---|---|---|
| Hydroxypivalinaldehyde (87 wt %, water content ~7 wt %) | 102.13 | 225 g | 1.917 |
| Propionic acid | 74.08 | 904 mL | 12.075 |
| p-Toluenesulfonic acid monohydrate | 190.22 | 10.94 g | 0.057 |
| Cyclohexane | | 662 mL | | p-Toluenesulfonic acid monohydrate (10.94 g, 0.057 mol) was added to a solution of hydroxypivalinaldehyde (225 g, 1,917 mol) and propionic acid (904 mL, 12.075 mol) in 662 mL of cyclohexane at RT. The obtained mixture was refluxed at 72-76° C. and water was removed via a dean-stark apparatus over 5 h. After water removal, a distillation was performed until an inner temperature of 140° C. The crude residue was subjected to fractionated distillation to prepare a sample of (2,2-dimethyl-3-oxo-propyl) propionate in a purity of >99 GC-area % as colorless liquid for olfactory testing.

NMR analysis: $^{13}C$ NMR (126 MHz, CDCl$_3$) δ=203.60, 174.15, 67.77, 46.37, 27.36, 18.82, 18.82, 9.05. $^1H$ NMR (500 MHz, Chloroform-d) δ=9.54 (s, 1H), 4.13 (s, 2H), 2.33 (d, J=7.7 Hz, 2H), 1.12 (s, 9H).

Example 15: Synthesis of [2-methyl-2-(4-methyl-enetetrahydropyran-2-yl)propyl] propanoate and its Double Bond Isomers

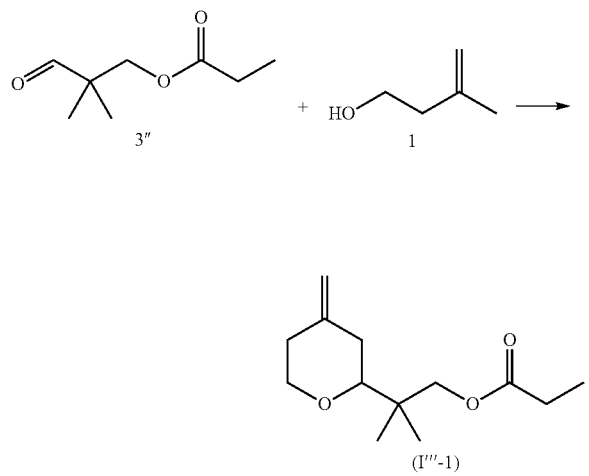

| Compound | MW | Mass/Volume | Moles |
|---|---|---|---|
| HPA-propionate from example 14, 96.6 GC-a % | 158.19 | 24 g | 0.147 |
| 3-Methyl-3-buten-1-ol | 86.13 | 15.68 g | 0.182 |
| Bortrifluoride-Diethylether | 141.93 | 4.3 g | 0.030 |
| Toluene | | 241 mL | |

BF$_3$-etherate (4.3 g, 0.003 mol) was added to a solution of HPA-propionate (24 g, 0.147 mol) and 3-methyl-3-buten-1-ol (15.68 g, 0.182 mol) in 241 mL of toluene at RT. The obtained mixture was stirred at 90° C. After 4 h, the reaction mixture was brought to RT and washed with 50 mL of a saturated aqueous solution of NaHCO$_3$. The phases were separated and the organic phase was dried with sodium sulfate. After filtration and evaporation of the solvent at 60° C. and 150-10 mbar, the crude product was purified by distillation to afford the title compound having a purity of 98% (GC area %) for olfactory testing.

The GC analysis revealed a 2% GC area of isomer I′′′-1, a 62% GC area of isomer I′′′2, and a 35% GC area of the isomer I′′′-3.

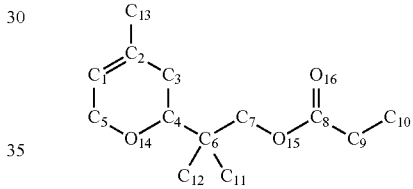

Isomer I′′′-2: $^{13}C$ NMR (126 MHz, CDCl$_3$) δ=174.51, 132.06, 119.91, 77.29, 70.12, 66.56, 37.35, 29.91, 27.71, 23.20, 20.92, 19.40, 9.27. $^1H$ NMR (500 MHz, Chloroform-d) δ=5.45-5.37 (m, 1H), 4.22-3.88 (m, 4H), 3.33 (dd, J=11.1, 3.1 Hz, 1H), 2.45-2.02 (m, 3H), 1.78-1.60 (m, 4H), 1.20-1.11 (m, 3H), 0.99-0.90 (s 6H).

Isomer I′′′-3: $^{13}C$ NMR (126 MHz, CDCl$_3$) δ=174.51, 134.30, 119.91, 78.20, 69.94, 64.22, 38.18, 30.08, 27.71, 23.55, 21.33, 20.05, 9.24. $^1H$ NMR (500 MHz, Chloroform-d) δ=5.45-5.35z (m, 1H), 4.10-3.88 (m, 3H), 3.86 (s, 1H), 3.53 (td, J=11.2, 3.4 Hz, 1H), 2.41-2.16 (m, 3H), 1.78-1.59 (m, 4H), 1.20-1.11 (m, 3H), 0.93-0.86 (s, 6H).

2. Olfactory Tests

In order to test the quality and intensity of the odor of the compounds (I) of the present invention, scent strip tests were performed.

For this purpose, strips of absorbent paper were dipped into solution containing 1 to 10% by weight solution of the compound (I) to be tested in ethanol or triethylcitrate. After evaporation of the solvent (about 30 sec.) the scent impression was olfactively evaluated by a trained perfumer.

The results of the scent test are summarized in table 1.

TABLE 1
| | Results of the scent tests. | |
|---|---|---|
| Example no. | Compound | Odor Description |
| 1 | 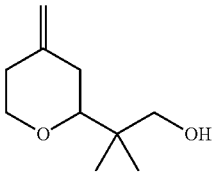<br>(I'-1)<br>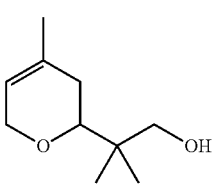<br>(I'-2)<br>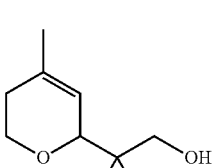<br>(I'-3)<br>molar ratio of 40:25:35 | Pineapple, green, chrysanthemum |
| 6 | 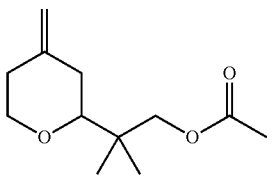<br>(I''-1)<br>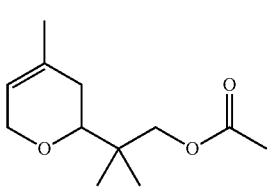<br>(I''-2)<br>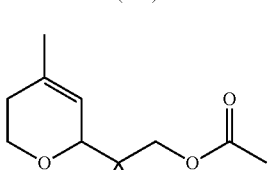<br>(I''-3)<br>molar ratio of 70:15:15 | Floral, apricot, green, bux tree |

TABLE 1-continued
Results of the scent tests.
| Example no. | Compound | Odor Description |
|---|---|---|
| 7 | 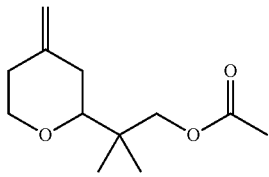<br>(I''-1)<br>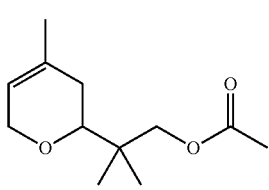<br>(I''-2)<br>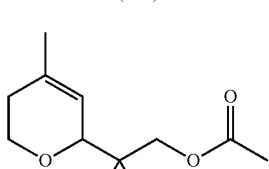<br>(I''-3)<br>GC-area % 44:18:33 | Sweet, woody, green, herbal |
| 13 | 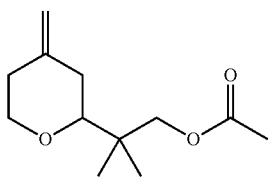<br>(I''-1)<br>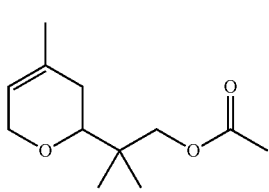<br>(I''-2)<br>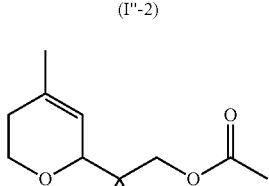<br>(I''-3)<br>GC Area % 2:66:30 | Same profile as example 7 but much less intense. |

TABLE 1-continued
Results of the scent tests.
| Example no. | Compound | Odor Description |
|---|---|---|
| 8 | 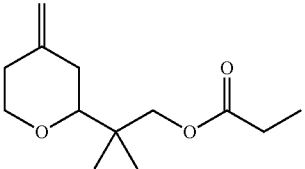 [SMILES: C=C1CCOC(C(C)(C)COC(=O)CC)C1] (I'''-1) 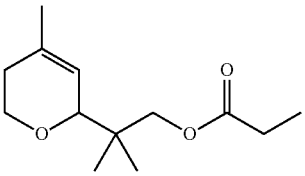 [SMILES: CCC(=O)OCC(C)(C)C1C=C(C)CCO1] (I'''-3) 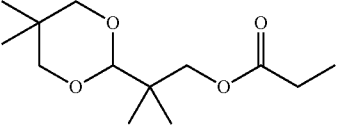 [SMILES: CCC(=O)OCC(C)(C)C1OCC(C)(C)CO1] (II'''.1) 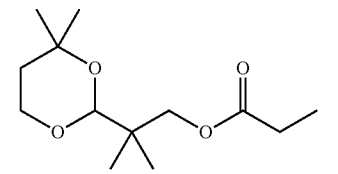 [SMILES: CCC(=O)OCC(C)(C)C1OCCC(C)(C)O1] (II'''.2) molar ratio of 50:20:20:5 | White floral, freesia, grape |
| 9 | 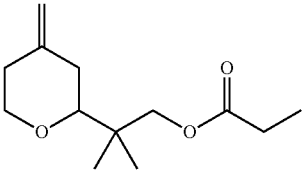 [SMILES: C=C1CCOC(C(C)(C)COC(=O)CC)C1] (I'''-1) 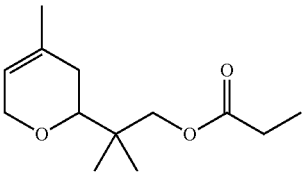 [SMILES: CCC(=O)OCC(C)(C)C1CC(C)=CCO1] (I'''-2) | Woody, ambery, pepper, natural, warm, spicy |

TABLE 1-continued

Results of the scent tests.

| Example no. | Compound | Odor Description |
|---|---|---|
|  | (I'''-3) GC Area % 52:23:19 |  |
| 15 | (I'''-1) | Cedarwood, smoky, dusty. Sample much less intense in comparison with example 8 and 9 |
|  | (I'''-2) |  |
|  | (I'''-3) GC Area % 2:62:35 |  |
| 10 | (I$^{iv}$-1) | Floral, pencil shavings, carrot, lime, bergamot |
|  | (I$^{iv}$-2) |  |

TABLE 1-continued

Results of the scent tests.

| Example no. | Compound | Odor Description |
|---|---|---|
| | (I$^{iv}$-3) molar ratio of 35:45:20 | |
| 11 | (I$^{v}$-1) | Etheral, herbal, soapy, mimosa, cedarwood, floral |
| | (I$^{v}$-2) | |
| | (I$^{v}$-3) molar ratio of 50:30:20 | |

Sales Products and Advantageous Fragrance Compositions

Solution A is the non-diluted product of example 1.
Solution B is the non-diluted product of example 6.
Solution C is the non-diluted product of example 7.
Solution D is the non-diluted product of example 8.
Solution E is the non-diluted product of example 9.
Solution F is the non-diluted product of example 10.
Solution G is the non-diluted product of example 11.
Solution H is the non-diluted product of example 13.
Solution I is the non-diluted product of example 15.

Advantageous Fragrance Compositions:

Solution A as described above was formulated in the compositions according to table 2. The amounts given in table 2 are weight units in grams.

TABLE 2

Fragrance compositions 1A and 1B

| | 1A | 1B |
|---|---|---|
| Lactone C10 gamma (5-hexyloxolan-2-one) | 2 | 2 |
| Bourgeonal (3-(4-tert-butylphenyl)propanal) | 2 | 2 |
| Citronellol | 3 | 3 |
| Aldehyde C-14 (5-heptyloxolan-2-one) | 3 | 3 |
| Allyl heptylate | 4 | 4 |
| Amber core (1-(2-tert-butylcyclohexyl)oxybutan-2-ol) | 4 | 4 |
| Ethyl-2-methyl butyrate | 4 | 4 |
| Geranyl acetate | 5 | 5 |
| Helional (3-(1,3-benzodioxol-5-yl)-2-methylpropanal) | 10 | 10 |
| Manzanate (ethyl 2-methylpentanoate) | 10 | 10 |
| Amberwood (ethoxymethoxycyclododecane) | 10 | 10 |
| Hexyl acetate | 11 | 11 |
| Benzyl salicylate | 12 | 12 |

TABLE 2-continued

Fragrance compositions 1A and 1B

| | 1A | 1B |
|---|---|---|
| Magnolan (2,4-dimethyl-4,4a,5,9b-tetrahydroindeno[1,2-d][1,3]dioxine) | 15 | 15 |
| Verdox (2-tert-butylcyclohexyl) acetate) | 25 | 25 |
| Bergamot oil bergaptene free | 25 | 25 |
| Linalol | 30 | 30 |
| Dipropylene glycol | 45 | 45 |
| Iso E Super (Tetramethyl acetyloctahydronaphthalenes) | 110 | 110 |
| Pyranol (4-methyl-2-(2-methylpropyl)oxan-4-ol) | 170 | 170 |
| Hedione (methyl 3-oxo-2-pentylcyclopentaneacetate) | 200 | 200 |
| Galaxolide 50% IPM (1,3,4,6,7,8-hexahydro-4,6,6,7,8,8-hexamethylcyclopenta(g)-2-benzopyran 50% in isopropyl myristate) | 300 | 300 |
| Solution A | 25 | 50 |
| | 1025 | 1050 |

Solution A as described above was formulated in the compositions according to table 3. The amounts given in table 3 are weight units in grams.

TABLE 3

Fragrance compositions 2A and 2B

| | 2A | 2B |
|---|---|---|
| Raspberry ketone (4-(4-hydroxyphenyl)butan-2-one) | 4 | 4 |
| Vanitrope (2-ethoxy-5-prop-1-enylphenol) | 6 | 6 |
| Cyclamen aldehyde (at least 90% 2-methyl-3-(p-isopropylphenyl)-propionaldehyde; secondary component: 5% 3-(p-cumenyl)-2-methylpropionic acid) | 10 | 10 |
| Bicyclononalactone (3,4,4a,5,6,7,8,8a-octahydrochromen-2-one) | 10 | 10 |
| Aldehyde C-14 (5-heptyloxolan-2-one) | 14 | 14 |
| Ethylvanillin (3-ethoxy-4-hydroxybenzaldehyde) | 16 | 16 |
| Heliotropine (1,3-benzodioxole-5-carbaldehyde) | 20 | 20 |
| Iso E Super (tetramethyl acetyloctahydronaphthalenes) | 20 | 20 |
| Sandela (3-[5,5,6-trimethylbicyclo[2.2.1]hept-2-yl]cyclohexan-1-ol) | 30 | 30 |
| Vanillin isobutyrate ((4-formyl-2-methoxyphenyl) 2-methylpropanoate) | 40 | 40 |
| Aldehyde C-18 (5-pentyloxolan-2-one) | 50 | 50 |
| Benzyl salicylate | 60 | 60 |
| Hexyl cinnamic aldehyde (2-(phenylmethylidene)octanal) | 70 | 70 |
| Hedione (methyl 3-oxo-2-pentylcyclopentaneacetate) | 130 | 130 |
| Pyranol (4-methyl-2-(2-methylpropyl)oxan-4-ol) | 150 | 150 |
| Ethylene brassylate (1,4-dioxacycloheptadecane-5,17-dione) | 170 | 170 |
| Galaxolide 50% IPM (1,3,4,6,7,8-hexahydro-4,6,6,7,8,8-hexamethylcyclopenta(g)-2-benzopyran 50% in isopropyl myristate) | 200 | 200 |
| Solution A | 10 | 20 |
| | 1010 | 1020 |

Fragrance composition 3 corresponds to fragrance composition 1A, where Solution A is replaced by the same amount of Solution B. Fragrance composition 4 corresponds to fragrance composition 1B, where Solution A is replaced by the same amount of Solution B. Fragrance composition 5 corresponds to fragrance composition 2A, where Solution A is replaced by the same amount of Solution B. Fragrance composition 6 corresponds to fragrance composition 2B, where Solution A is replaced by the same amount of Solution B.

Fragrance composition 7 corresponds to fragrance composition 1A, where Solution A is replaced by the same amount of Solution C. Fragrance composition 8 corresponds to fragrance composition 1B, where Solution A is replaced by the same amount of Solution C. Fragrance composition 9 corresponds to fragrance composition 2A, where Solution A is replaced by the same amount of Solution C. Fragrance composition 10 corresponds to fragrance composition 2B, where Solution A is replaced by the same amount of Solution C.

Fragrance composition 11 corresponds to fragrance composition 1A, where Solution A is replaced by the same amount of Solution D. Fragrance composition 12 corresponds to fragrance composition 1B, where Solution A is replaced by the same amount of Solution D. Fragrance composition 13 corresponds to fragrance composition 2A, where Solution A is replaced by the same amount of Solution D. Fragrance composition 14 corresponds to fragrance composition 2B, where Solution A is replaced by the same amount of Solution D.

Fragrance composition 15 corresponds to fragrance composition 1A, where Solution A is replaced by the same amount of Solution E. Fragrance composition 16 corresponds to fragrance composition 1B, where Solution A is replaced by the same amount of Solution E. Fragrance composition 17 corresponds to fragrance composition 2A, where Solution A is replaced by the same amount of Solution E. Fragrance composition 18 corresponds to fragrance composition 2B, where Solution A is replaced by the same amount of Solution E.

Fragrance composition 19 corresponds to fragrance composition 1A, where Solution A is replaced by the same amount of Solution F. Fragrance composition 20 corresponds to fragrance composition 1B, where Solution A is replaced by the same amount of Solution F. Fragrance composition 21 corresponds to fragrance composition 2A, where Solution A is replaced by the same amount of Solution F. Fragrance composition 22 corresponds to fragrance composition 2B, where Solution A is replaced by the same amount of Solution F.

Fragrance composition 23 corresponds to fragrance composition 1A, where Solution A is replaced by the same amount of Solution G. Fragrance composition 24 corresponds to fragrance composition 1B, where Solution A is replaced by the same amount of Solution G. Fragrance composition 25 corresponds to fragrance composition 2A, where Solution A is replaced by the same amount of Solution G. Fragrance composition 26 corresponds to fragrance composition 2B, where Solution A is replaced by the same amount of Solution G.

Fragrance composition 27 corresponds to fragrance composition 1A, where Solution A is replaced by the same amount of Solution H. Fragrance composition 28 corresponds to fragrance composition 1B, where Solution A is replaced by the same amount of Solution H. Fragrance composition 29 corresponds to fragrance composition 2A, where Solution A is replaced by the same amount of Solution H. Fragrance composition 30 corresponds to fragrance composition 2B, where Solution A is replaced by the same amount of Solution H.

Fragrance composition 31 corresponds to fragrance composition 1A, where Solution A is replaced by the same amount of Solution I. Fragrance composition 32 corresponds to fragrance composition 1B, where Solution A is replaced by the same amount of Solution I. Fragrance composition 33 corresponds to fragrance composition 2A, where Solution A is replaced by the same amount of Solution I. Fragrance composition 34 corresponds to fragrance composition 2B, where Solution A is replaced by the same amount of Solution I.

The invention claimed is:

1. A compound of the formula (I)

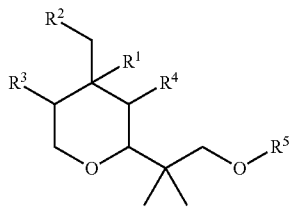

wherein $R^1$, $R^2$, $R^3$ and $R^4$ are hydrogen; or one of $R^2$, $R^3$ or $R^4$ together with $R^1$ represents a double bond; and the others of $R^2$, $R^3$ or $R^4$ are hydrogen; and $R^5$ is selected from the group consisting of hydrogen, $C_1$-$C_4$-alkyl and —C(=O)—$R^6$; where $R^6$ is selected from the group consisting of hydrogen and $C_1$-$C_4$-alkyl;

or a mixture thereof, a stereoisomer thereof or a mixture of stereoisomers thereof;

or a mixture of at least one compound of the formula (I) with one or both of the compounds of the formula (II.1) and/or (II.2)

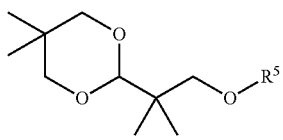

wherein $R^5$ is as defined above.

2. The compound as claimed in claim 1, where in the compound of the formula (I) one of $R^2$, $R^3$ or $R^4$ together with $R^1$ represents a double bond; and the others of $R^2$, $R^3$ or $R^4$ are hydrogen.

3. The compound as claimed in claim 2, which is a mixture containing at least two of compounds (I-1), (1-2) and (1-3), where the compound (I-1) is a compound of the formula (I) in which $R^2$ together with $R^1$ represents a double bond and $R^3$ and $R^4$ are hydrogen; the compound (I-2) is a compound of the formula (I) in which $R^3$ together with $R^1$ represents a double bond and $R^2$ and $R^4$ are hydrogen; and the compound (I-3) is a compound of the formula (I) in which $R^4$ together with $R^1$ represents a double bond and $R^2$ and $R^3$ are hydrogen.

4. The compound as claimed in claim 3, which is a mixture containing the compound (I-1), the compound (1-3) and optionally also the compound (1-2); and which is in particular a mixture containing all three compounds (I-1), (I-2) and (I-3).

5. The compound as claimed in claim 1, which is a mixture containing at least one of compounds (I-1), (1-2) and/or (1-3) where the compound (I-1) is a compound of the formula (I) in which $R^2$ together with $R^1$ represents a double bond and $R^3$ and $R^4$ are hydrogen; the compound (1-2) is a compound of the formula (I) in which $R^3$ together with $R^1$ represents a double bond and $R^2$ and $R^4$ are hydrogen; and the compound (1-3) is a compound of the formula (I) in which $R^4$ together with $R^1$ represents a double bond and $R^2$ and $R^3$ are hydrogen; and further containing one or both of the compounds of the formula (II.1) and/or (II.2).

6. The compound as claimed in claim 1, where $R^5$ is $C_1$-$C_4$-alkyl, preferably methyl or ethyl, in particular methyl.

7. The compound as claimed in claim 1, where $R^5$ is hydrogen.

8. The compound as claimed in claim 1, where $R^5$ is —C(=O)—$R^6$; where $R^6$ is hydrogen or $C_1$-$C_4$-alkyl.

9. Composition comprising a compound of formula (I), a mixture thereof, a stereoisomer thereof, a mixture of stereoisomers thereof or a mixture of at least one compound of the formula (I) with one or both of the compounds of the formula (II.1) and/or (II.2) as defined in claim 1, and at least one further component selected from the group consisting of aroma chemicals different from compounds (I), (II.1) and (II.2), non-aroma chemical carriers, anti-oxidants and deodorant-active agents; and in particular from the group consisting of aroma chemicals different from compounds (I), (II.1) and (II.2), surfactants, oil components, solvents, anti-oxidants and deodorant-active agents.

10. The composition according to claim 9, which is selected from the group consisting of perfume compositions, body care compositions, products for oral or dental hygiene, hygiene articles, cleaning compositions, textile detergent compositions, compositions for scent dispensers, foods, food supplements, pharmaceutical compositions and crop protection compositions.

11. A method for modifying and/or enhancing the aroma of a composition comprising incorporating into the composition a compound of the formula (I), a mixture thereof, a stereoisomer thereof, a mixture of stereoisomers thereof or a mixture of at least one compound of the formula (I) with one or both of the compounds of the formula (II.1) and/or (II.2) as defined in claim 1.

12. The method according to claim 11, wherein the composition is selected from perfume compositions, body care compositions, products for oral or dental hygiene, hygiene articles, cleaning compositions, textile detergent compositions, compositions for scent dispensers, foods, food supplements, pharmaceutical compositions and crop protection compositions.

13. A method for preparing a compound of the formula (I), a mixture thereof, a stereoisomer thereof, a mixture of stereoisomers thereof or a mixture of at least one compound of the formula (I) with one or both of the compounds of the formula (II.1) and/or (II.2) as defined in claim 1, which method comprises (a) reacting 3-methylbut-3-en-1-ol (isoprenol) with 3-hydroxy-2,2-dimethyl-propanal (hydroxypivalinaldehyde) in acidic medium to obtain a reaction mixture containing a compound of the formula (I') and optionally also one or both of the compounds of the formula (II'.1) and/or (II'.2)

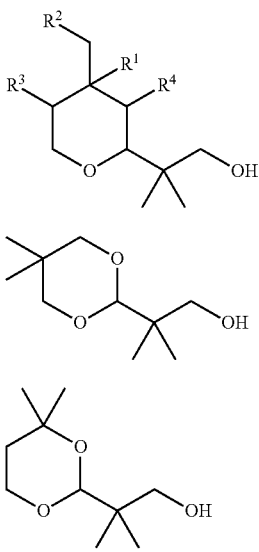

wherein one of $R^2$, $R^3$ or $R^4$ together with $R^1$ represents a double bond and the others of $R^2$, $R^3$ or $R^4$ are hydrogen;

(b) optionally isolating the compound of the formula (I') and, if present, the compounds (II'-1) and (II'-2) from the reaction mixture obtained in step (a) or enriching it in the reaction mixture obtained in step (a);

(c) if a compound of the formula (I) or a compound of the formula (I'), wherein $R^1$, $R^2$, $R^3$ and $R^4$ are hydrogen, is to be prepared: subjecting the reaction mixture obtained in step (a) or the product obtained in step (b) to a hydrogenation reaction to obtain a compound of the formula (I') wherein $R^1$, $R^2$, $R^3$ and $R^4$ are hydrogen;

(d) if a compound of the formula (I) is to be prepared in which $R^5$ is not hydrogen:
subjecting the reaction mixture obtained in step (a) or the product obtained in step (b) or the product obtained in step (c) to an etherification or esterification reaction;

(e) if a compound of the formula (I), wherein $R^1$, $R^2$, $R^3$ and $R^4$ are hydrogen and $R^5$ is not hydrogen, is to be prepared and step (c) has not been carried out: subjecting the product obtained in step (d) to a hydrogenation reaction; and (f) optionally subjecting the product obtained in step (b) or step (c) or step (d) or step (e) to a purification step.

14. A method for preparing a compound of the formula (I) wherein $R^5$ is selected from the group consisting of $C_1$-$C_4$-alkyl and —C(=O)—$R^6$; a mixture thereof, a stereoisomer thereof or a mixture of stereoisomers thereof as defined in claim 1, which method comprises (i) subjecting 3-hydroxy-2,2-dimethyl-propanal (hydroxypivalinaldehyde) to an etherification or esterification reaction to obtain a reaction mixture containing a compound of the formula 3

wherein $R^{5a}$ is selected from the group consisting of $C_1$-$C_4$-alkyl and —C(=O)—$R^6$;

(ii) optionally isolating the compound of the formula 3 from the reaction mixture obtained in step (i) or enriching it in the reaction mixture obtained in step (i);

(iii) reacting the reaction mixture obtained in step (i) or the product obtained in step (ii) with 3-methylbut-3-en-1-ol (isoprenol) in the presence of a $BF_3$ source to obtain a reaction mixture containing a compound of the formula (I) wherein one of $R^2$, $R^3$ or $R^4$ together with $R^1$ represents a double bond and the others of $R^2$, $R^3$ or $R^4$ are hydrogen and wherein $R^5$ is selected from the group consisting of $C_1$-$C_4$-alkyl and —C(=O)—$R^6$;

(iv) if a compound of the formula (I), wherein $R^1$, $R^2$, $R^3$ and $R^4$ are hydrogen and $R^5$ is selected from the group consisting of $C_1$-$C_4$-alkyl and —C(=O)—$R^6$, is to be prepared: subjecting the product obtained in step (iii) to a hydrogenation reaction; and (v) optionally subjecting the product obtained in step (iii) or step (iv) to a purification step.

* * * * *